US012778647B2

(12) United States Patent
Niver

(10) Patent No.: US 12,778,647 B2
(45) Date of Patent: Nov. 3, 2026

(54) COMPRESSION DEVICE, BONE PLATE, BONE PLATE ASSEMBLY, KIT, AND METHOD

(71) Applicant: Medline Industries, LP, Northfield, IL (US)

(72) Inventor: Ryan Niver, Glenview, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 19/204,740

(22) Filed: May 12, 2025

(65) Prior Publication Data

US 2025/0268631 A1 Aug. 28, 2025

Related U.S. Application Data

(63) Continuation of application No. 18/640,049, filed on Apr. 19, 2024, now Pat. No. 12,343,052, which is a continuation of application No. 17/353,250, filed on Jun. 21, 2021, now Pat. No. 11,974,789.

(51) Int. Cl.
*A61B 17/80* (2006.01)
*A61B 17/86* (2006.01)
*A61B 17/68* (2006.01)

(52) U.S. Cl.
CPC ...... *A61B 17/8033* (2013.01); *A61B 17/8028* (2013.01); *A61B 17/8052* (2013.01); *A61B 17/8061* (2013.01); *A61B 17/863* (2013.01); *A61B 17/866* (2013.01); *A61B 17/8695* (2013.01); *A61B 2017/681* (2013.01)

(58) Field of Classification Search
CPC ................ A61B 17/80; A61B 17/8033; A61B 17/8047; A61B 17/8052; A61B 17/8685; A61B 17/8695
See application file for complete search history.

(56) References Cited

U.S. PATENT DOCUMENTS 9,101,423 B2 * 8/2015 Hulliger ............. A61B 17/8052
10,390,866 B2 * 8/2019 Baker ................ A61B 17/8052
2016/0081722 A1 * 3/2016 Josse .................. A61B 17/7059
606/246

* cited by examiner

*Primary Examiner* — Larry E Waggle, Jr.
(74) *Attorney, Agent, or Firm* — Fitch, Even, Tabin & Flannery LLP

(57) ABSTRACT

A compression device made of a superelastic material having a peripheral portion with an upper surface, a lower surface, and a central opening extending therethrough is provided. Tips of one or more resilient structures of the compression device project inward of the peripheral portion and form an opening. The one or more resilient structures are configured to exert a biasing force in a direction when deformed in an opposite direction. Also provided is a bone plate assembly comprising a captively retained compression device and a bone plate comprising one or more integrally formed resilient structures.

7 Claims, 54 Drawing Sheets

1701
1703
1702

1714
1710
1701
1716
1714
1712

1714
1716
1702
1714
1710
1712

1714
1710
1714
1703
1716
1712

COMPRESSION DEVICE, BONE PLATE, BONE PLATE ASSEMBLY, KIT, AND METHOD

RELATED APPLICATIONS

This application is a continuation of U.S. application Ser. No. 18/640,049, filed Apr. 19, 2024, which is a continuation of U.S. application Ser. No. 17/353,250, filed Jun. 21, 2021 now issued as U.S. Pat. No. 11,974,789, the contents of each of which are incorporated herein by their entireties.

FIELD

The disclosure relates generally to orthopedic implants, and more specifically, to a compression device, bone plate, bone plate assembly, kit, and method useful in orthopedic applications.

BACKGROUND

Washers and bone plates are typically employed to help distribute load on an underlying structure upon insertion of a fastener, such as a screw. It is known to use washers and plates in connection with threaded fasteners for orthopedic applications. For example, a washer or plate may be used in connection with a bone screw to reduce the stress and load applied against the surface of a bone.

Lag screws are commonly used to repair bone fractures to compress joints or fracture sites in orthopedic applications. In use, an unthreaded proximal portion of the lag screw slides freely in a hole drilled through the bone on a proximal side of the joint or fracture site while a threaded distal end is screwed into an opposite side of the joint or fracture. As the screw is tightened, the threaded portion biases a distal region of the joint or fracture towards the proximal region to compress the joint or fracture site. Washers or bone plates may be used in connection with such lag screws to reduce the stress on the proximal cortical bone due to such compression. Bone plates can also be used to tie together multiple bones or bone fragments As a patient ambulates or as a fracture or joint heals, the compression provided by the lag screw may deteriorate. As a result of cyclic loading, gaps may form between the fractured bone segments thus interfering with the healing process. Maintaining compression in orthopedics across joints or fracture sites is desirable for healing.

Also, surgery involving numerous separate implantable parts such as washers, and plates and fasteners can increase complexity of surgical procedures. Reducing the number of independent small parts to be implanted is desirable from the standpoint of simplifying surgical procedures.

It has now been found that a compression device composed at least in part of a superelastic material positioned between the head of fastener, such as a lag screw, and a bone surface may exert a biasing force in a direction along the axis of the fastener when the compression device is deformed in an opposite direction, as described in more detail hereinbelow. This biasing force can assist in maintenance of compression at a bone fracture.

It has further been found that a bone plate assembly can comprise a compression device captively retained within a bone plate. In other constructions, a bone plate can include an integral compression structure wherein a plate body and the compression structure of the bone plate comprise a superelastic material. With devices such a bone plate assembly or a bone plate that include an integral compression structure, the number of items to be implanted during orthopedic surgery can be reduced.

DETAILED DESCRIPTION

Figure 1:
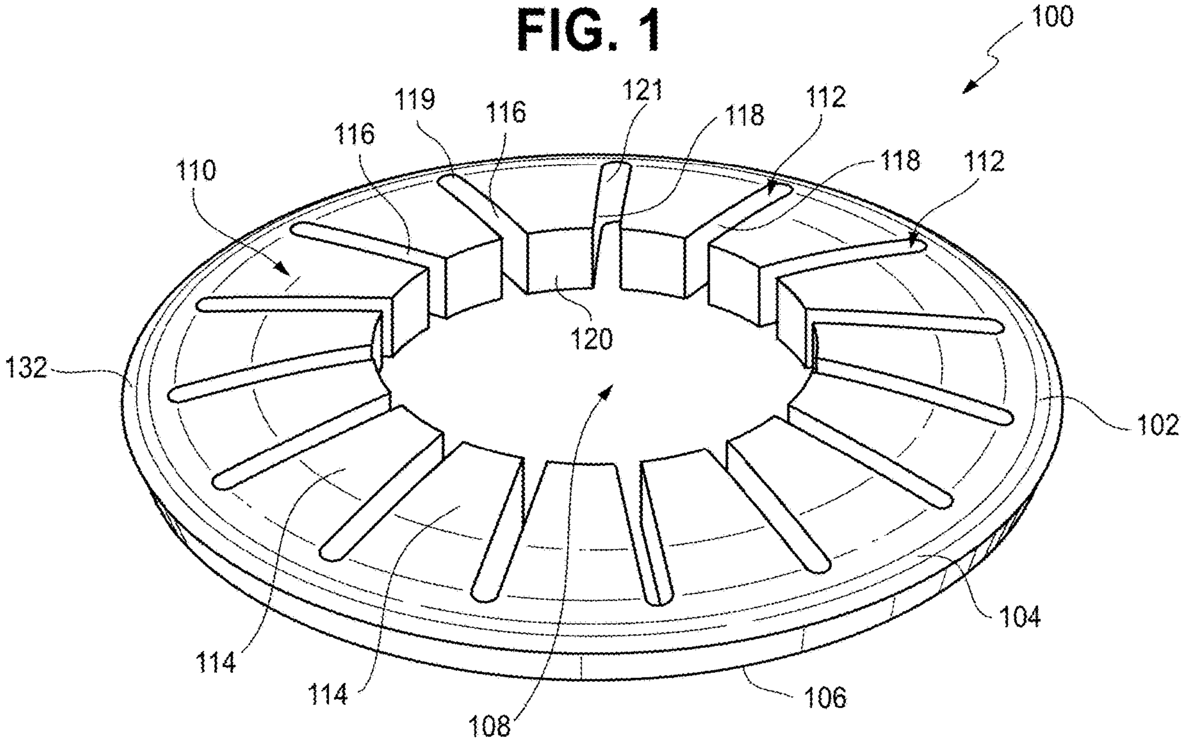
FIG. 1 is a perspective view of an exemplary compression device.

Generally, a compression device comprising a superelastic material is provided. The compression device has a peripheral portion with an upper surface, and a lower surface. The peripheral portion of a compression device may be in the form of a generally annular ring and in some cases the ring may be a generally circular ring. In other forms the peripheral portion may have a generally square or triangular configuration. One or more resilient structures, such as a plurality of resilient teeth, project inwardly from the peripheral portion. In some forms, tips of one or more resilient structures of a compression device form an opening through the compression device. The opening can generally be disposed at a center of the compression device or at an off-center position. In some embodiments, a plurality of resilient teeth are spaced radially along the peripheral portion of the compression device and tips of the teeth form an opening. The resilient structures and are configured to exert a biasing force in a direction when deformed in an opposing direction. The one or more resilient structures, such as teeth and adjoining portions of the compression device, may be formed of superelastic material. In other forms, an entire compression device is formed of superelastic material.

The resilient structures of a compression device are also configured to continue to exert biasing force in one direction when the resilient structures of the compression device are decompressed in an opposite direction. This continued exertion of compressive force upon decompression of a compression device can aid in maintaining compression between bone fragments upon healing. As noted above, compression would normally decrease upon healing when fixed together using just a bone screw and washer. The maintained application compressive force during the healing process can aid in the realization of Wolff's law (e.g., applying compressive force to healing bone to effect bone restructuring that supports the applied force). In some forms, a compression device can generally have a property of producing at least about 10 N, 20 N, 40 N, or 90 N of compressive force upon decompression of the compression device by an axial distance of 1.5 mm. In some forms, a compression device can have a property of producing at least about 2 N, 3 N, 5 N, 25 N, or 65 N of compressive force upon decompression of the compression device by an axial distance of 2.0 mm.

A compression device can generally be sized to provide a desired opposing biasing force when a resilient structure of the compression device is impinged upon and deformed by the head of a fastener passing through the opening of the compression device. The superelastic resilient teeth exert a biasing force against the head portion of the fastener upon being deformed. A compression device can generally have any useful thickness such as thicknesses ranging from about 0.25 mm to about 1.25 mm, from about 0.5 mm to about 1 mm, from about 0.6 mm to about 0.9 mm, and from about 0.7 mm to about 0.8 mm. Similarly, a compression device can have any useful outer diameter such as outer diameters ranging from about 5 mm to about 14 mm, from about 5.75 mm to about 12.75 mm, from about 6 mm to about 11 mm, from about 6.6 mm to about 10.2 mm, from about 7 mm to about 9 mm, and from about 7.65 mm to about 8.5 mm.

A fastener typically includes a head and a shaft. A shaft is generally sized to pass through an opening of a compression device, an opening formed by tips of one or more integrally formed structures, and an aperture through a bone plate, as discussed in more detail hereinbelow. A fastener can generally have any useful length, shaft diameter, and head diameter configured to impinge upon one or more resilient structures included in a compression device or integrally formed with a bone plate as further discussed below. A fastener can have a shaft diameter ranging from 4.5 to 8 mm, 5 to 7.5 mm, 5.5 to 7 mm, 3 to 5 mm, or 3.5 to 4.5 mm. A fastener may be a lag-type bone screw comprises a head, at least threaded distal portion and optionally an unthreaded proximal portion. Alternatively, a fastener can be a fully threaded screw comprising a head and a fully threaded shaft. Examples of fasteners suitable for use with a compression device include un-cannulated (solid core) or cannulated bone screws (such as cannulated screws marketed under Medline UNITE®), nails, etc. Un-cannulated and cannulated bone screws may be of lag-type or fully threaded. Preferred fasteners include those indicated for use in bone reconstruction, osteotomies, arthrodesis, joint fusion, fracture repair, and fracture fixation of bones.

The opening formed by one or more resilient structures, such as tips of a plurality of teeth, can be sized to allow a shaft of a fastener to pass therethrough such that the head of a fastener impinges upon and deforms, i.e. biases, the one or more resilient structures. Examples of useful head diameters of fasteners range from about 2.5 mm to about 7.5 mm, from about 3 mm to about 7 mm, from about 3.5 mm to about 6.5, from about 4 mm to about 6.0, and from about 4.5 mm to about 5.5. Examples of useful internal diameters of an opening formed by at least one resilient structure, such as tips of teeth, range from about 2.5 mm to about 6.8 mm, from about 2.85 mm to about 6.47 mm, from about 3 mm to about 6 mm, from about 3.5 mm to about 5.5 mm, from about 4 mm to about 5.5 mm, from about 3.3 mm to about 5.15 mm, from about 3.37 mm to about 4.25 mm, and from about 3.75 mm to about 4.15 mm. Generally, the relative dimensions of an internal diameter of an opening of a compression device and an outer diameter of a threaded portion of a screw can be sized such that the screw is advanced through the compression device by threading the screw through the opening. In other forms, the opening of a compression device and the threaded portion of the screw are sized such that the threaded portion of the screw can pass freely through the opening.

The size, shape and number of resilient structures, such as resilient teeth, can be adjusted to alter the force characteristics exerted by the resilient structures. For example, each tooth of a plurality of teeth can include a wedge-shaped projecting portion or projecting portion of any other appropriate shape such that an inferior portion of the tooth has a width greater than a superior portion thereof. In other forms, each tooth may include a cuboid-shaped projecting portion such that opposing sides of each tooth are substantially parallel one another. Likewise, the thickness of each tooth in a longitudinal direction may be consistent or may alternatively increase or decrease over a length thereof between the peripheral portion and a terminal end of each tooth.

In some forms of a compression device configured with resilient teeth, each tooth of the plurality of resilient teeth has a tip portion extending proximally beyond the upper surface of the peripheral portion such that the compression device is of a convex configuration in a resting and unbiased state (i.e., before the resilient teeth have been deformed). The depth of the tip portion extending proximally beyond the upper surface of the peripheral portion may be adjusted to alter the force characteristics of the compression device, as discussed in further detail hereinafter. In other forms, each tooth has a tip portion extending distally beyond the lower surface of the peripheral portion in an unbiased state such that the compression device is in a concave configuration. Similarly, the depth of the tip portion extending distally beyond the lower surface of the peripheral portion may be adjusted to alter the force characteristics of the compression device. In other aspects, each tooth of the plurality of teeth has a tip portion that extends medially in a resting and unbiased state (i.e., not extending proximally or distally of the peripheral portion), such that the compression device is in a flat configuration.

In some constructions, a compression device comprises a plurality of teeth tips of the teeth extend inwardly but separate tips of the teeth extend in different directions relative to the peripheral portion. Some of the teeth may extend proximally relative to the peripheral portion and other teeth extend distally relative to the peripheral portion. With this configuration, the head of a fastener can impinge upon and deform the proximally extending teeth. At the same time, the distally extending teeth on the opposite side of the compression device are deformed toward the plane of the peripheral portion by a bone surface or a bone plate. With the forces applied on opposite sides of the compression device in this manner, the compressed teeth exert biasing forces toward the top and the bottom sides of the compression device.

In other forms, a first set of teeth extend proximally relative to the peripheral portion and a second set of teeth extend medially relative to the peripheral portion. In yet other forms, a first set of teeth extend medially relative to the peripheral portion and a second set of teeth extend distally relative to the peripheral portion. With these constructions the first set of teeth can exert a first level of biasing force and the second set of teeth can exert a second level of biasing force as the head of a fastener impinges upon and is advanced against the teeth, such that the first level of biasing force is higher than the second level of biasing force.

The compression device described above may be installed and seated directly against the cortex of a bone, or in alternative forms, a bone plate may be employed. In still other embodiments, the compression device may be at least partially countersunk in a bone segment. For example, a countersink tool (e.g., a drill) may be used to drill a countersunk bore in the bone segment sized to at least partially receive and seat the compression device therein. In some forms, peripheral edges of the compression device may contact and abut the surface of the bone segment, and the resilient teeth may be compressed inwards within the countersunk bore. A fastener may thereafter be advanced through the opening of the compression device in the countersunk bore such that the head portion of the fastener compresses the resilient teeth and remains flush with the cortex of the bone to reduce surrounding tissue irritation.

In some forms, a bone plate comprises a plate body including an upper plate surface, a lower plate surface, an aperture through the plate body, and a countersunk region formed about the aperture and open to the upper plate surface. An aperture is generally sized to receive a shaft of a fastener therethrough. A countersunk region of a bone plate can be generally sized to receive a compression device therein. In some aspects, a bone plate assembly comprises a compression device captively retained within the countersunk region of a bone plate.

In some forms, a countersunk region of a bone plate comprises an intermediate seat region sized to seat the compression device. The countersunk region can further include an inner intermediate surface including a mating structure to captively retain a compression device. Any compression device described herein can generally be captively retained in a bone plate of a bone plate assembly. In some embodiments, an inner intermediate surface of the countersunk region comprises a mating structure including an intermediate annular recessed region that mates with the peripheral portion of the compression device to captively retain the compression device in the bone plate. In other forms, an inner intermediate surface of the countersunk region comprises a mating structure that includes one or more lobes that protrude inwardly from the inner intermediate surface of the countersunk region. The lobes can mate with the peripheral portion of the compression device so that the compression device is captively retained in the bone plate.

In some forms, a compression device is retained in the bone plate such that a tip portion of at least one resilient tooth projects in an unbiased state beyond the upper surface of the peripheral portion of the compression device. In this configuration, the tip portion of at least one tooth can extend toward or beyond an upper plate surface of the bone plate. In other forms, a compression device is retained in a bone plate such that a tip portion of at least one tooth of a compression device extends medially in an unbiased state, such that the tip of the tooth does not extend toward the upper or lower plate surfaces of the bone plate. In yet other forms, a compression device is retained in the bone plate such that a tip portion of at least one tooth extends distally, in an unbiased state, beyond the lower surface of the peripheral portion of the compression device, such that the tip of the tooth extends toward the bottom plate surface of the bone plate. In this respect, the "bottom" surface is the surface that faces the bone when in use.

The bottom surface of a countersunk region can generally have any structure. In some forms, a bottom surface of a countersunk region is concave relative to the upper plate surface of the bone plate. The aperture of the plate body can generally be disposed at the center or off-center from the concave structure of the countersunk region. A concave bottom surface of a countersunk region can receive one or more teeth of a compression device that have been deformed toward the bottom surface of the countersunk region by the head of a fastener. In other forms, the bottom surface of a countersunk region is generally planar.

In other constructions, a bone plate generally comprises a plate body including an upper plate surface, a lower plate surface, an aperture through the plate body, and at least one inwardly projecting resilient structure, such as at least one resilient tooth, that is integrally formed with the plate body. The at least one integrally formed resilient structure extends toward an axis of the aperture. An aperture is generally sized to receive a shaft of a fastener therethrough. The plate body and at least one integrally formed resilient structure can comprise a material that is superelastic at human body temperatures, as described herein, such that the at least one resilient structure exerts a biasing force in a direction when deformed in an opposing direction. In some embodiments, the bone plate and the at least one integral formed resilient structure are both composed entirely of superelastic material.

Tips of one or more integrally formed resilient structures, such as tips of a plurality of integrally formed resilient teeth, can form an opening at least substantially aligned with the aperture through the plate body of the bone plate. In this configuration, the shaft of a fastener can pass through both the opening and the aperture. The opening formed by the at least one integrally formed resilient structure has any useful internal diameter as discussed herein in connection with an opening formed by at least one resilient structure of a compression device. The one or more integrally formed resilient structures can generally have any size, shape, and number as discussed herein in connection with resilient structures of a compression device. Generally, resilient structures (e.g., teeth) can have any useful thickness measured in a direction from an upper surface toward a lower surface of a compression device. In some forms, resilient structures can have thicknesses ranging from 0.2 to 1.1 mm, 0.3 to 0.9 mm, 0.4 to 0.8 mm, 0.5 to 1.5 mm, 0.6 to 1.4 mm, 0.7 to 1.3 mm, 0.8 to 1.0 mm, 0.9 to 1.2 mm, 4.5 to 8 mm, 5 to 7.5 mm, 5.5 to 7 mm, or 6 to 6.5 mm. Thickness of resilient structures can also be dictated by the surgical application of the compression device and the diameter of a fastener to pass through the opening of the compression device. For example, a compression device utilized for general foot plating can include resilient structures having thicknesses ranging from 0.4 to 0.8 mm and an opening sized to receive a fastener having a shaft diameter of 3.5 mm. In other forms, a compression device utilized for ankle fusion can have resilient structures having thicknesses ranging from 0.8 to 1.0 mm or greater and be used with a fastener having a shaft diameter ranging from 5.5 to 7 mm.

In some forms, an unbiased tip portion of at least one integrally formed resilient structure extends proximally toward and/or beyond the upper plate surface from the point of integration of the resilient structure with the plate body. In other forms, an unbiased tip portion of at least one integrally formed resilient structure extends medially from the point of integration of the resilient structure with the plate body. In yet other forms, an unbiased tip portion of at least one integrally formed resilient structure extends distally toward the lower plate surface from the point of integration of the resilient structure with the plate body.

In some embodiments, tip portions of a plurality of integrally formed teeth collectively extend toward or from the upper plate surface and form a structure that is convex relative to the upper plate surface. In other embodiments, tip portions of a plurality of integrally formed teeth collectively extend toward the lower plate surface and form a structure that is concave relative to the upper plate surface. In yet other forms, tip portions of a plurality of integrally formed teeth extend medially and collectively form a structure that is flat or generally parallel to both the upper and lower plate surfaces.

In other embodiments, some of the integrally formed teeth extend proximally in an unbiased state toward the upper plate surface and some of the integrally formed teeth extend medially in an unbiased state relative to the bone plate. In other forms, some of the integrally formed teeth extend medially in an unbiased state relative to the bone plate and some of the integrally formed teeth extend distally in an unbiased state toward the lower plate surface of the bone plate. In these configurations, the integrally formed teeth oriented in different unbiased directions provide different biasing forces as the head of a fastener progressively deforms the teeth.

A bone plate including at least one integral inwardly projecting resilient tooth can also generally include one or more countersunk regions formed about the aperture through the plate body such that aperture is disposed at an axis of the countersunk regions or a position offset from the axis. Countersunk regions can be open to an upper or lower plate surface of the plate body. In some forms, a tip of at least one integral tooth extends toward the aperture from an inner intermediate surface of the countersunk region.

Some constructions of a bone plate comprise both upper and lower countersunk regions disposed on either side of at least one integrally formed tooth. The two countersunk regions are formed about the same aperture and the at least one integrally formed resilient tooth forms a boundary between the two countersunk regions. In this configuration, deformation of the at least one tooth can occur within the upper and/or lower countersunk region by advancement of the head of the fastener against the tooth. In some forms, the head of the fastener can be received substantially below the upper plate surface of a bone plate.

In other forms, a bone plate includes a countersunk region open to a lower plate surface of a bone plate such that at least one integral tooth is formed along the upper plate surface of the bone plate. With this construction, the tooth can be deformed within the countersunk region by impingement of the head of a fastener against the tooth. Deformation of the tooth permits the head of the fastener to be received substantially below the upper plate surface.

In yet other constructions, a countersunk region is open to an upper plate surface of a bone plate and least one integral tooth is formed proximal to or along the bottom plate surface of the bone plate with the tip of the at least one tooth extending proximally toward the upper plate surface. The at least one tooth can be deformed within the countersunk region and toward a plane of the bottom plate surface by advancement of a head of fastener against the tooth.

Alternatively, a bone plate assembly including a compression device, or a bone plate comprising at least one integrally formed resilient tooth formed, can comprise an off-angle structure configured to dispose an axis of a fastener at a non-perpendicular angle through the bone plate. For example, such a structure can be useful for compressing together separate pieces of fractured bone in a manner such that the fastener can pass through portions of the fractured bone pieces having optimal thicknesses.

In some embodiments, an off-angle structure is configured to retain a compression device above a plane of an upper surface of a bone plate. In other embodiments, an off-angle structure is configured to retain a portion of compression device above a plane of the upper surface of the bone plate and another portion of the compression device below the plane of the upper surface. In yet other embodiments, an off-angle structure is formed such that a plurality of integrally formed teeth is disposed above a plane of an upper surface of a bone plate. In other constructions, an off-angle structure is formed such that a portion of a plurality of integrally formed teeth is disposed above a plane of an upper surface of a bone plate and another portion of the teeth are disposed below the plane of the upper surface.

In yet other forms, any of a compression device, a bone plate assembly including a compression device, and a bone plate comprising at least one integrally formed resilient tooth can be disposed on opposite ends of a fastener passing through bone. The same or different devices can be attached to the opposite ends of the fastener. For example, a fastener can pass through a device such as compression device, a bone plate assembly, or a bone plate with at least one integrally formed resilient structure, as described herein, such that the head of the fastener impinges upon and biases one or more resilient structures of the device. With the shaft of the fastener passing through bone, the opposite end of the fastener can pass through an additional one of these devices positioned against an opposite side of the bone. A nut on the fastener can impinge upon and bias one or more resilient structures of the additional device such that compression can be provided from both ends of a fastener.

In some forms, a kit including a compression device as described above and a countersink tool may be provided. The countersink tool may include a drill or drill bit to be used to drill a countersunk bore to install the compression device in a segment of bone, the bore sized to at least partially seat the compression device therein. In other forms, a kit comprises a bone plate assembly including a captive compression device, as described herein. In other forms, a kit includes a bone plate and a separate compression device, where the compression device can later be inserted into the bone plate to be captively retained in the bone plate for surgical application. In some embodiments, a kit can include a bone plate comprising at least one integrally formed resilient tooth, as described herein. Optionally, a kit may further include one or more fasteners as described herein.

The present disclosure further provides methods for installing a compression device into a bone segment, methods for installing a bone plate assembly on a bone segment, and methods for installing a bone plate including one or more integrally formed resilient structures on a bone segment. Indications treatable by these methods include, but or not limited to, lateral malleolar fractures, medial malleolar fractures, metatarsal osteotomies (Chevron, Austin, Akin, Ludloff, etc. to address bunions), arthrodesis of the first metatarsal cuneiform joint (lapidus fusion), arthrodesis of the first metatarsophalangeal joint (MTP), medial displacement calcaneal osteotomy (MDCO), LisFranc arthrodesis and/or stabilization, 1st (lapidus), 2nd, 3rd, 4th, and 5th tarsometatarsal (TMT) fusions, intercuneiform fusions, navicular-cuneiform (NC) fusion, talo-navicular (TN) fusion, calcaneo-cuboid (CC) fusion, medial column fusions (NC and 1st TMT), ankle fusion, subtalar joint fusion, Jones and avulsion fractures of the 5th metatarsal, humeral head fractures, distal humerus fractures, proximal femoral fractures, femoral neck and head fractures, tibial plateau fracture, distal femur fracture, femoral condyle fracture, proximal tibia fracture, calcaneal fracture, and general metaphyseal fractures.

For example, a bone segment of a patient may be surgically exposed and a guide wire may be advanced therein. A pilot hole may be cut into the bone segment to receive the shaft of a fastener therein, and thereafter, a countersunk bore may be cut into the bone segment. In some forms, the compression device may be placed around the shaft of a cannulated bone screw such that the bone screw and compression device may be advanced over the guide wire to insert the bone screw into the pilot hole. In other forms, the compression device provided herein may be placed in the countersink, and a bone screw may be advanced through the opening of the compression device and into the pilot hole. As the bone screw is advanced, the head portion of the bone screw impinges upon, and compresses, at least one tooth of the superelastic compression device into the countersunk bore such that the teeth exert a biasing force against the head portion of the bone screw. In other methods, the compression device may be positioned immediately adjacent the cortex of the bone.

A method for installing bone plate assembly may include providing a bone plate assembly and fastener as disclosed herein and surgically exposing a bone segment of a patient. A pilot hole can be cut into the bone segment to receive a shaft of a fastener. A surgical guide wire can optionally be advanced within the bone segment. In some forms, the guide wire is disposed through the opening of a compression device captively retained in a bone plate and the aperture of the bone plate. Optionally, the shaft of a cannulated bone screw can also be inserted through the opening of the captive compression device and the aperture through the bone plate before advancing the assembly to the surface of the exposed bone segment. The bone plate assembly can be advanced over the guide wire to dispose the assembly against the bone segment. The screw can be advanced into the bone segment via the opening in the compression device and the aperture of the bone plate. In other embodiments, a bone plate assembly provided herein is placed against a surface of the bone segment and the bone screw is inserted through opening and aperture of the bone plate assembly and advanced into the bone segment.

In yet other embodiments, methods for installing bone plate including one or more integrally formed resilient structures, such as the teeth described herein, against a bone segment are provided. A fastener and a bone plate including or more integrally formed resilient structures can be provided and a bone segment of a patient can be surgically exposed. The exposed bone segment can be cut to provide a pilot hole into the bone to receive a shaft of the fastener. Optionally, a surgical guide wire can be advanced within the bone segment. In some forms, the guide wire is disposed through the aperture in the bone plate. Optionally, the shaft of a cannulated bone screw can also be inserted through the aperture through the bone plate before advancing the bone plate to the surface of the exposed bone segment. The bone plate can be advanced over the guide wire and positioned against the bone segment. The screw can be advanced into the bone segment via the aperture of the bone plate. In other forms, a bone plate including at least one integrally formed resilient structure is placed against a surface of the bone segment and the bone screw is inserted through aperture of the bone plate assembly and advanced into the bone segment.

Figure 2:
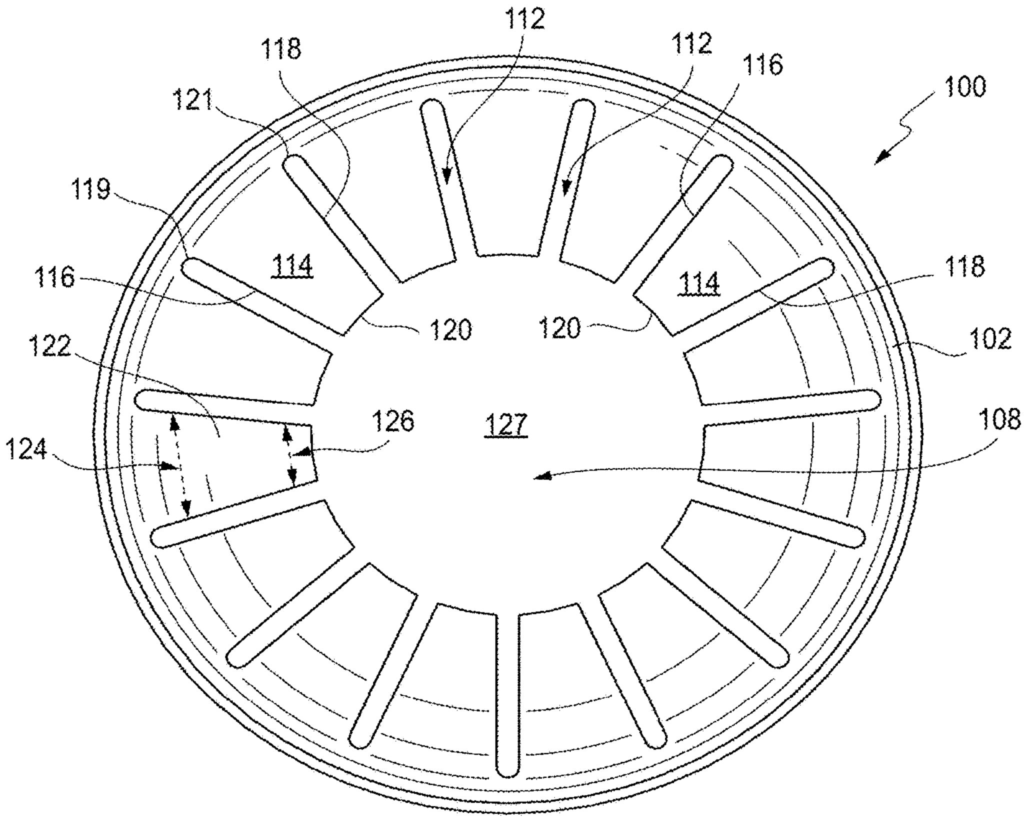
FIG. 2 is a top plan view of the compression device shown in FIG. 1.
Figure 3:
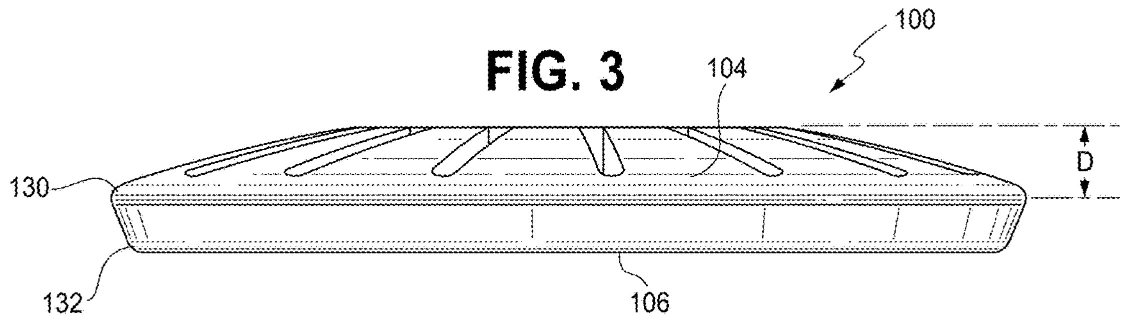
FIG. 3 is a side elevational view of the compression device shown in FIG. 1.

Referring now to the drawings, and more particularly FIGS. 1-3, an embodiment of compression device 100 is provided including a peripheral portion 102 in the form of a generally annular ring having an upper surface 104, a lower surface 106, and a central opening 108 extending therethrough. As illustrated, a plurality of resilient teeth 110 project radially inwardly from the peripheral portion 102 into the central opening 108. The teeth 110 are spaced such that they define gaps 112 therebetween. By way of example, and for simplicity of reference to the drawings, the illustrated peripheral portion 102 is shown as a generally circular ring but the peripheral portion may, in other forms, be circular, oblong, square, triangular, or obround.

Each tooth 114 of the plurality of teeth 110 may include a first side edge 116, a second side edge 118, and a terminal edge 120. As illustrated in FIG. 2, each tooth 114 of the compression device 100 has a generally wedge-shaped portion 122 such that an inferior portion 124 of the tooth 114 has a width wider than a superior portion 126 of the tooth 114. So configured, the major part of the first side edge 116 of each tooth 114 is substantially parallel the major part of the second side edge 118 of an adjacent tooth 114 and, together with the cusps 119, 121, define a U-shaped gap 112 therebetween. In other forms, the teeth and gaps can have a variety of different shapes. For example, the teeth may have a substantially triangular profile such that the first and second side edges 116, 118 terminate at a single point as opposed to terminal edge 120, among other forms.

In addition, the peripheral portion 102 and plurality of teeth 110 may have a variety of different thicknesses. Depending on the shape of the teeth 110 and the thickness of the peripheral portion 102 and the teeth 110, different force characteristics may be imparted to the compression device. For example, in some forms, each tooth may reduce in thickness along a length thereof between the inferior portion and the superior portion. In other forms, the thickness of each tooth may remain consistent along the length thereof between the inferior portion and superior portion. The configuration of the teeth will affect the axial force exerted upon compression of the teeth by the head of a bone screw or other fastener.

As illustrated in FIGS. 1-3, the terminal edge 120 of each tooth 114 of the compression device 100 is contoured such that the terminal edges 120 of the teeth 110 define a major opening 127 within the central opening 108. The major opening as illustrated is generally defined by the rounded terminal edges 120 of each of the teeth, and in other forms, could be defined by terminal edges formed in other shapes. In one example form, the opening 127 defined by the terminal edges 120 of the teeth 110 has a diameter of about 7.5 mm (as measured based on a completed circle defined by completing the terminal edges 120 of the teeth), and the peripheral portion 102 has a diameter of about 15 mm. In other forms, the diameters of the opening 127 and the peripheral portion 102 may vary for different surgical procedures, or when the compression device 100 is used in connection with a bone plate as described in further detail below.

Additionally, the peripheral portion 102 of the compression device 100 may include chamfered or filleted edges (e.g., filleted edges 130, 132), as shown most clearly in FIG. 3, to inhibit or reduce irritation to surrounding tissue when the compression device 100 is installed adjacent a bone segment.

As described above, at least the resilient teeth are, and preferably the entire the compression device 100 is, formed of a superelastic material, generally a metal alloy such as a nitinol alloy, which is a family of nickel-titanium alloys. A compression device can optionally comprise other superelastic materials such as polyether ether ketone (PEEK) and beta-titanium alloys such as TiNbZrHfSn. The plurality of resilient teeth 110 will thereby exert a biasing force in an axial direction when deformed in an opposing axial direction, by which is contemplated a biasing force having an axial component. Superelasticity is a well-recognized phenomenon of certain alloys in which the material deforms reversibly in response to an applied stress. In some forms, the compression device material should be superelastic at both ambient temperatures (e.g., about 25° C.) and the normal body temperature of the intended patient, which, in the case of human patient, is in the range of about 36° to 38° C. In other embodiments, alloys that are not superelastic at ambient temperature but that become superelastic at body temperatures may be employed.

As illustrated, the compression device 100 is in a generally convex or dome-shaped configuration in its resting state before any force has been applied thereto. As seen most clearly in FIG. 3, the resilient teeth 110 extend radially inwards about the peripheral portion 102 in an arcuate configuration superior the upper surface 104 thereof at a depth D. In other words, a tip portion 123 of the teeth 110 extends proximally beyond the upper surface 104 of the peripheral portion 102. The depth D can be any suitable depth depending on the selected application and the desired force characteristics of the compression device 100. An exemplary range for depth D is from about 0.25 mm to about 1.0 mm. The selected depth can depend on a variety of factors, including the geometry of the teeth 110, the shape of the teeth 110, and the desired force characteristics of the compression device 100. In other forms, the depth D may be equal to about 0 mm such that the compression device 100 is substantially flat in the resting state, and a tip portion of the teeth 110 does not extend proximally beyond the upper surface 104 or distally beyond the lower surface 106, as discussed below with respect to FIG. 17. In still other forms, the resilient teeth 110 may extend radially inwards about the peripheral portion 102 in an arcuate configuration distal of the lower surface 106 thereof such that the compression device 100 is of a concave or bowl-shaped configuration, as discussed below with respect to FIG. 18. In further forms, a tip portion of a first number of teeth 110 may extend proximally beyond the upper surface 104 and a second number of teeth 110 may extend distally beyond the lower surface 106.

As shown, the plurality of teeth 110 of compression device 100 includes 15 teeth. However, the plurality of teeth 110 may include any number of teeth extending radially inward from the peripheral portion 102 of the compression device 100, including a single tooth in some forms. Although the teeth 110 shown in FIG. 2 are spaced equally about the peripheral portion 102 of the compression device 100, the teeth 110 may be arranged in different configurations with different spacing. Such different configurations and different numbers of teeth 110 may impart different force characteristics to the compression device 100 such that the resilient teeth may exert a stronger or weaker biasing force upon depression thereof.

The compression device 100 provided herein is configured to be used in connection with a variety of different fasteners, including threaded fasteners such as cannulated bone screw 128 illustrated in FIGS. 4-7. In other forms, nails for use in orthopedic applications or other suitable fasteners may be employed. The illustrated bone screw 128 is a lag-type bone screw commonly used for fixation or stabilization of one or more bone segments and includes a head portion 134, a shaft 138 having a proximal portion 140 configured to slide freely in a hole drilled through bone on a near side of the joint or fracture site, and a threaded distal end 142 configured to be screwed into an opposite side of the joint or fracture. In other forms, the bone screw 128 may be a fully threaded screw.

The shaft 138 is sized to fit within the major opening 127 of the compression device such that it is not impeded by the teeth. As the screw 128 is advanced into a bone segment, the head portion 134 of the screw 128 may contact the resilient teeth 110 of the compression device 100 proximate the near side of the bone while the threaded distal end 142 pulls the opposite side of the joint or fracture towards the near side to compress the fracture site. In some forms, the fastener such as bone screw 128 may be osseointegrating and may be formed of titanium or an alloy thereof, or may be formed of other biocompatible osseointegrating materials. In other forms, the fastener could be formed of bioresorbable materials such as poly-L-lactic acid (PLLA), polyether ether ketone (PEEK), among others.

Figure 4:
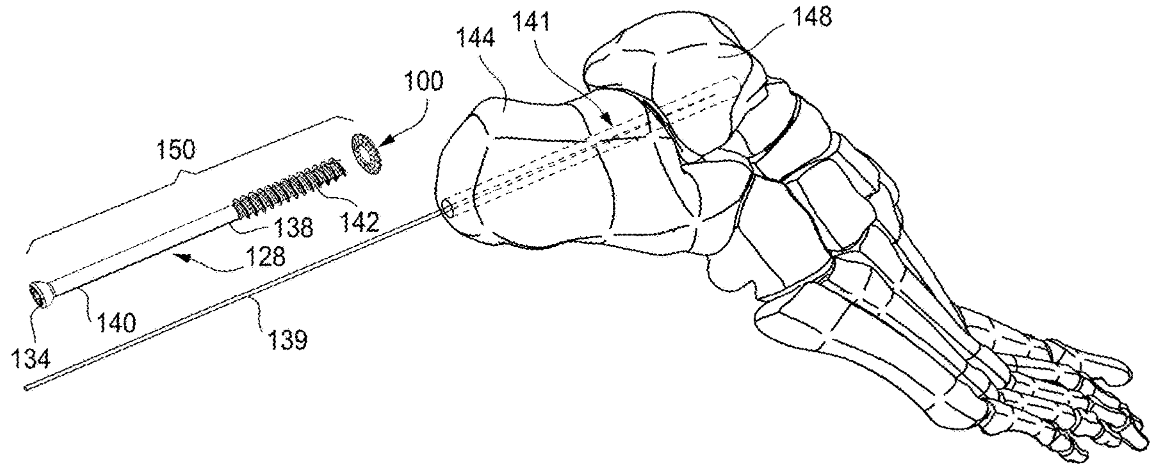
FIG. 4 is a view illustrating a cannulated lag-type bone screw, the compression device of FIG. 1, and a surgical region of a patient's calcaneus showing a guide wire inserted into the calcaneus with a pilot bore drilled therein.
Figure 5:
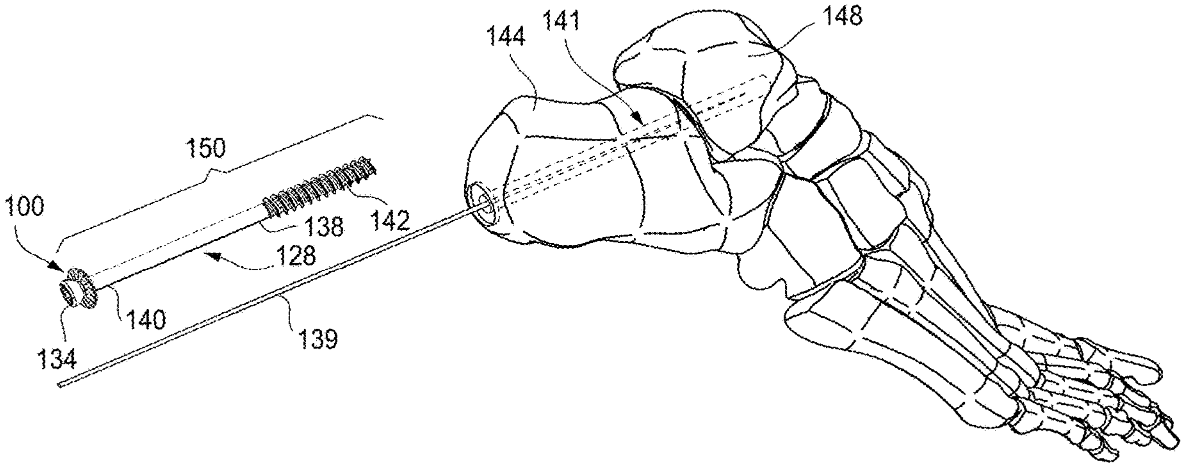
FIG. 5 is a perspective view of the surgical region of the patient's calcaneus as shown in FIG. 4 with a countersunk bore therein.

FIG. 4 illustrates an exemplary initial step for installation of cannulated bone screw 128 and compression device 100 in a patient's calcaneus 144. As shown a guide wire 139 is inserted into the calcaneus 144 and through a portion of the talus 148. A cannulated drill bit may advance along the guide wire to drill a pilot hole 141 for receiving the shaft 138 of the screw 128. As shown in FIG. 5, while the guide wire 139 is still inserted, a countersink tool having a drill bit (e.g., countersink tool shown in FIG. 23) may be used to drill the countersunk bore 146 that is sized to at least partially receive the compression device 100 and the head portion 134 of the bone screw 128 therein once installed. In addition, the compression device 100 may be positioned to surround the shaft 138 of the cannulated bone screw 128 proximate the head portion 134 such that both may be received over the guide wire 139 for installation as described below.

Figure 6:
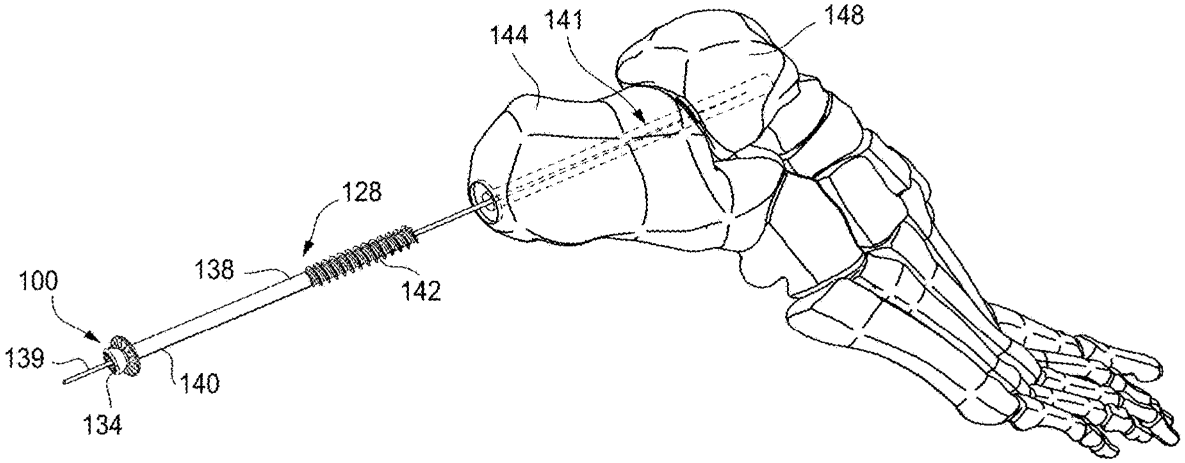
FIG. 6 is a perspective view of the surgical region of the patient's calcaneus as shown in FIG. 4 showing the cannulated bone screw and compression device received over the guide wire and aligned with the countersunk bore.
Figure 7:
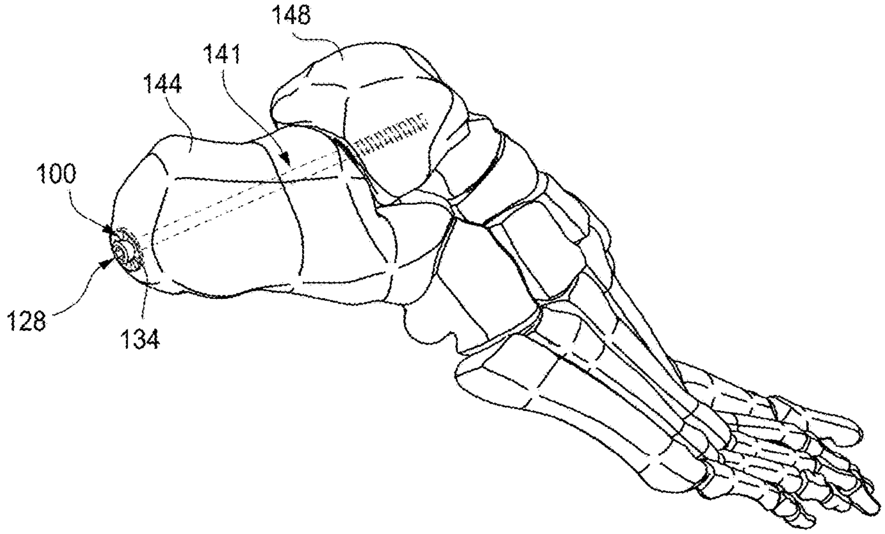
FIG. 7 is a perspective view depicting the surgical region of FIG. 6 after installation of the bone screw into the calcaneus and deformation of the compression device, and after the guide wire has been removed.

With respect to FIG. 6, the cannulated screw 128 and compression device 100 are shown aligned with the patient's calcaneus 144 and received along the guide wire 139 such that the compression device may be seated at least partially in the bore 146 and the screw may be advanced into the pilot hole 141. Thereafter, as shown in FIG. 7, the guide wire 139 is removed and the bone screw 128 is advanced into the calcaneus 144 such that the threaded distal end 142 of the screw 128 is advanced into the talus bone 148. The head portion 134 of the screw 128 impinges upon the teeth 110 of the compression device 100 and deforms the teeth 110 while the superelastic, resilient teeth 110 exert a biasing force in an opposite direction against the head portion 134 of the screw 128 to maintain compression between the calcaneus and the talus bones 144, 148. As illustrated, the teeth 110 of the compression device 100 are compressed into a flat configuration, and may further be compressed such that the compression device 100 is of a concave configuration with the teeth 110 deformed inwardly within the countersunk bore 146 due to impingement of the head portion 134 of the screw 128. The countersunk bore 146 may be sized such that upon compression of the compression device 100, the head portion 134 of the bone screw 128 is flush with the surface of the bone segment. In other words, the compression device 100 creates a constant biasing force under the head portion 134 of the bone screw 128 such that the resilient teeth 110 generate sustained compression between the calcaneus 144 and the talus 148.

In use, the compression device 100 is typically provided in the form of a kit including one or more compression devices 100 and a countersink tool (shown in FIG. 23) for drilling a countersink in a segment of bone. Optionally, the kit may also include a guide wire (e.g., guide wire 139). In other forms, the compression device 100 may be provided with a fastener such as bone screw 128 (e.g., kit 150 shown in FIG. 4). In some forms, an implant manufacturer may provide several sizes or shapes of compression devices or fasteners to accommodate various patients and types of procedures.

Figure 8:
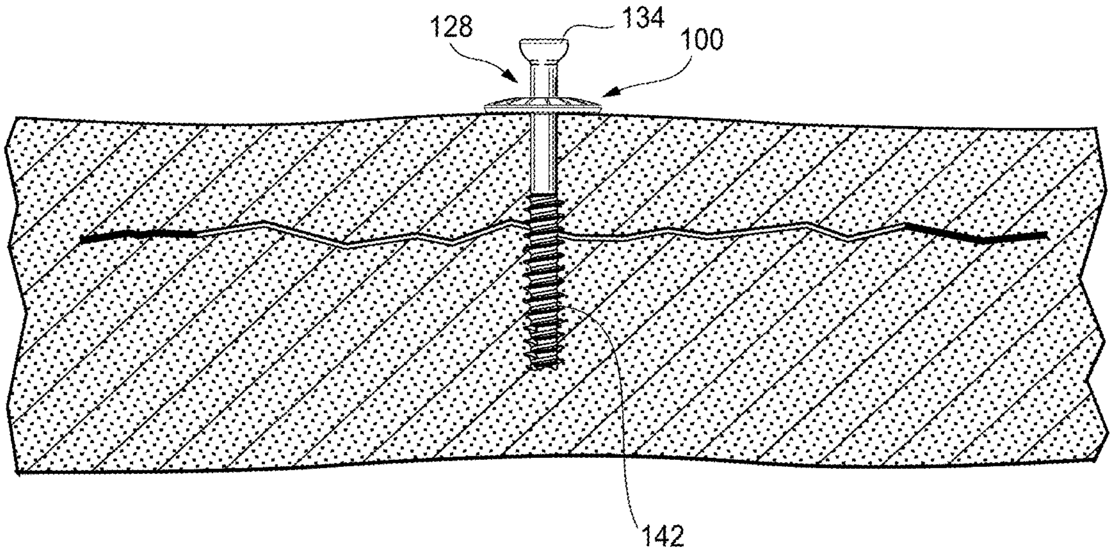
FIG. 8 is a cross-sectional view of a bone section of a patient into which a bone screw has been inserted during the process of advancing the bone screw but prior to impingement of the head of the bone screw on the compression device.
Figure 9:
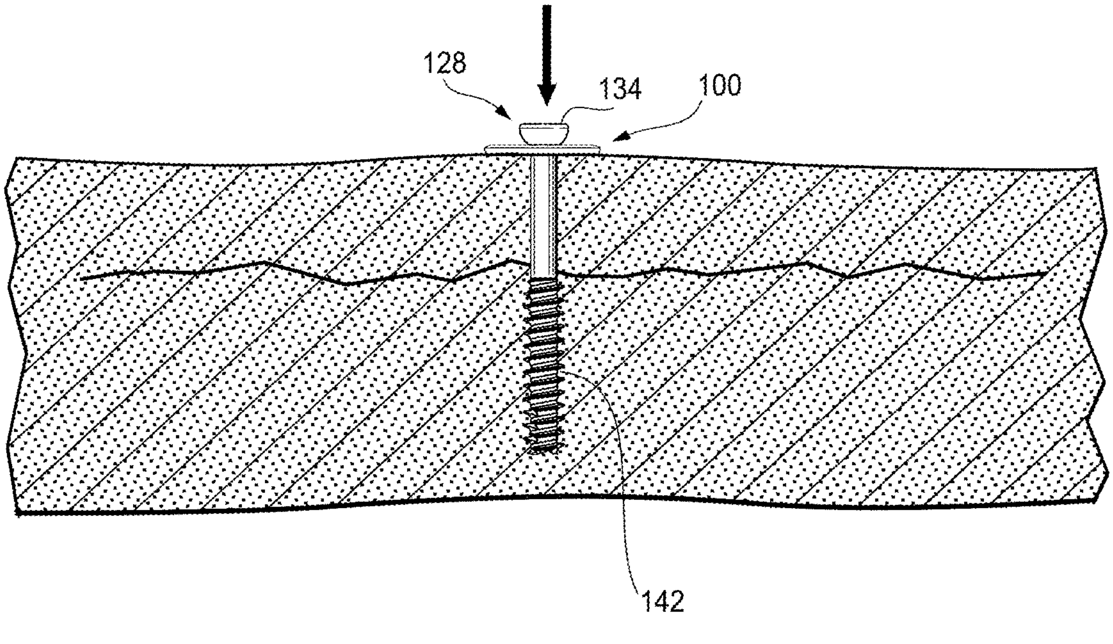
FIG. 9 is a cross-sectional view of the bone section shown in FIG. 8, at a further point during the process of advancing the bone screw and illustrating impingement of the head of the bone screw on the compression device.

With respect to the fractured bone segment depicted in FIGS. 8 and 9, an alternative use of the compression device 100 is shown. As illustrated in FIG. 8, compression device 100 has been positioned immediately adjacent the cortex of the bone segment and has not yet been compressed by the head portion 134 of the screw 128. The bone screw 128 is being advanced downwards through a pre-drilled bore into the bone segment such that the threaded distal portion 142 is inserted into the far portion of the fracture to compress the two fractured portions of bone.

FIG. 9 depicts a further point during the process of advancing the bone screw 128 and illustrating the impingement of the head portion 134 of the bone screw 128 on the resilient teeth 110 of the compression device 100. As shown, the threaded distal portion 142 of the screw 128 has been inserted into the far portion of the bone and the screw 128 is stabilizing the two fractured portions of bone. In addition, the resilient teeth 110 of the compression device 100 are now compressed and exert a biasing force upwards on the head portion 134 of the screw 128 to maintain such compressive force between the fractured bone segments. Even if patient ambulation or other factors disturb the compression of the bone segments imparted by the screw 128, the biasing force exerted by the resilient teeth 110 promotes continued compression. Although the bone screw 128 is shown advancing into the bone segment at an angle approximately transverse the surface of the bone, the bone screw 128 could also be advanced through the bone segment at an angle such that the resilient teeth 110 of the compression device 100 would still impart a biasing force having an axial component.

Figure 10:
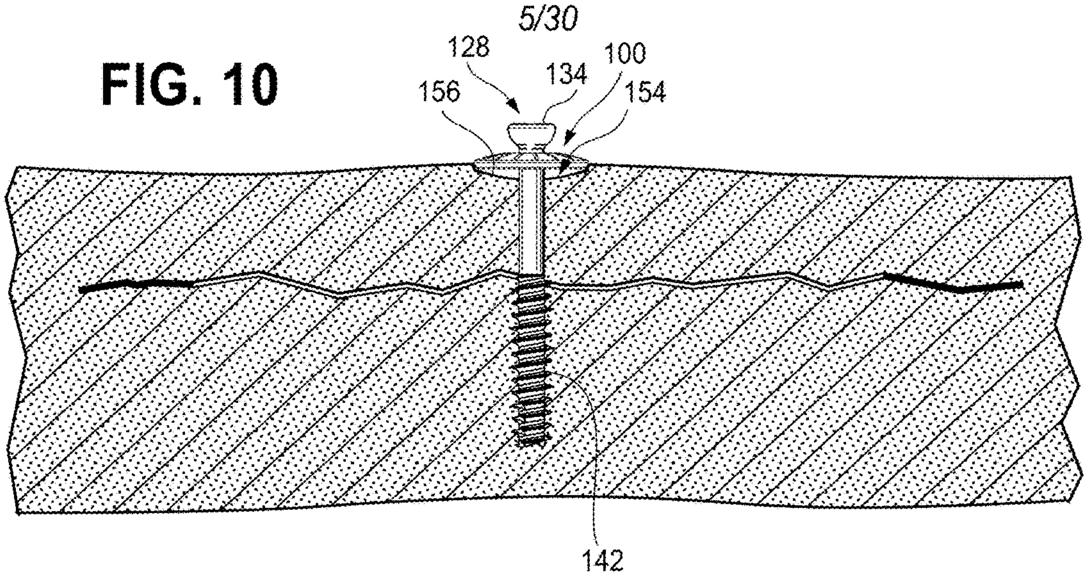
FIG. 10 is a cross-sectional view of a bone section of a patient with a compression device seated in a countersunk bore thereof during the process of advancing the bone screw but prior to impingement of the head of the bone screw on the compression device.
Figure 11:
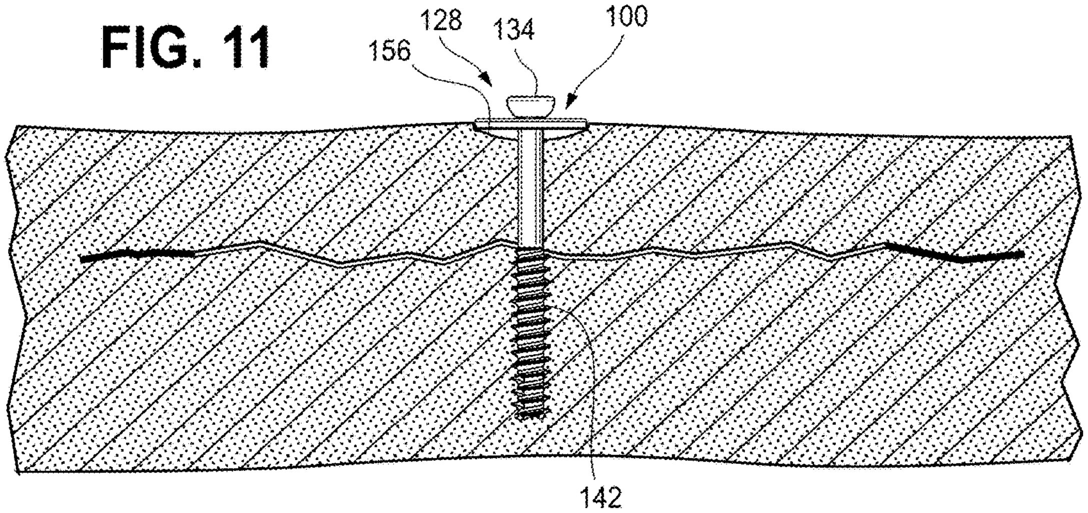
FIG. 11 is a cross-sectional view of the bone section shown in FIG. 10, at a further point during the process of advancing the bone screw and illustrating impingement of the head of the bone screw on the compression device.
Figure 12:
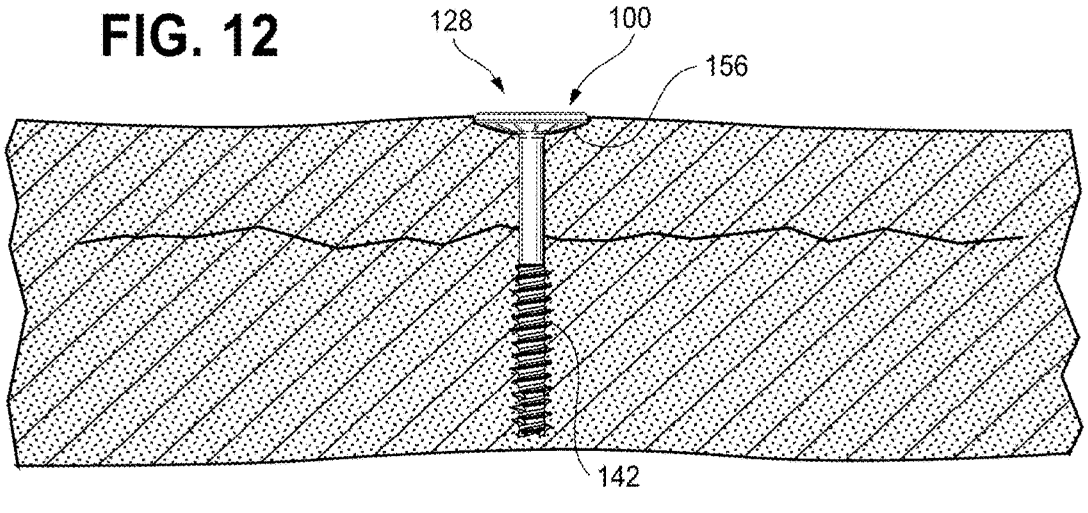
FIG. 12 is a cross-sectional view of the bone section shown in FIG. 10, at a final point during the process of advancing the bone screw and illustrating impingement of the head of the bone screw on the compression device.

Alternatively, the compression device 100 and screw may be countersunk as shown in FIGS. 10, 11 and 12. In these Figures a bone screw 128 is configured to be positioned adjacent a bore 152 sized to at least partially receive the compression device 100, or resilient teeth 110 thereof, within. As illustrated in FIG. 10, compression device 100 has been positioned proximate the countersunk bore 152 with edges thereof contacting the surface of the bone, and the device 100 and has not yet been compressed by the head portion 134 of the screw 128. The bone screw 128 is being advanced downwards through the bone segment such that the threaded distal portion 142 is inserted into the far portion of the fracture to compress the two fractured portions of bone. As illustrated, a distal portion 154 of the bore 152 includes a concave surface 156 (e.g., as drilled via the countersink tool shown in FIG. 23) such that the compression device 100 may be fully compressed thereon as shown more clearly in FIG. 12, and the head portion 134 of the screw 128 may be positioned substantially flush with the surface of the bone. In other forms, the distal portion 154 of the bore 152 is of a generally flat surface such that the teeth 110 of the compression device 100 may be compressed thereagainst.

FIG. 11 illustrates a further point during the process of advancing the bone screw 128 and illustrating the impingement of the head portion 134 of the bone screw 128 on the resilient teeth 110 of the compression device 100. At this point, the head portion 134 has compressed the resilient teeth 110 of the compression device 100 such that the device 100 is deformed into a flat configuration.

FIG. 12 illustrates a final point during the process of advancing the bone screw 128, showing the resilient teeth 110 of the compression device 100 fully compressed inwardly within the bore 152 by the head portion 134 of the bone screw 128 such that the compression device 100 is of a concave configuration and the teeth 110 are abutting concave surface 156. At this point, the head portion 134 is received within the bore 152 such that it is substantially flush with the surface of the bone and the threaded distal portion 142 has been inserted into the far portion of the bone such that the screw 128 compresses the two fractured portions of bone. In addition, the resilient teeth 110 of the compression device 100, now compressed into a concave configuration, exert an axial biasing force on the head portion 134 of the screw 128.

Figure 13:
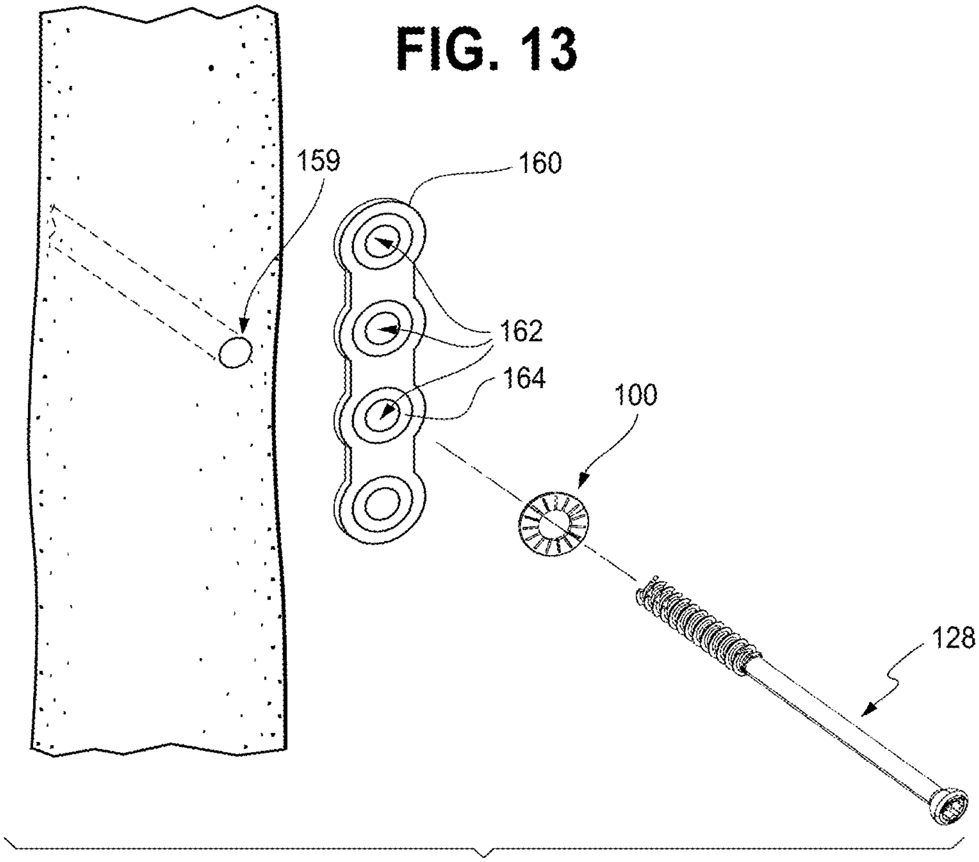
FIG. 13 is a view illustrating a lag-type bone screw, the compression device of FIG. 1, a bone plate, and a surgical region of a patient's bone, the Figure illustrating the relative positioning of the screw, bone plate, compression device, and bone prior to insertion of the screw into the bone.
Figure 14:
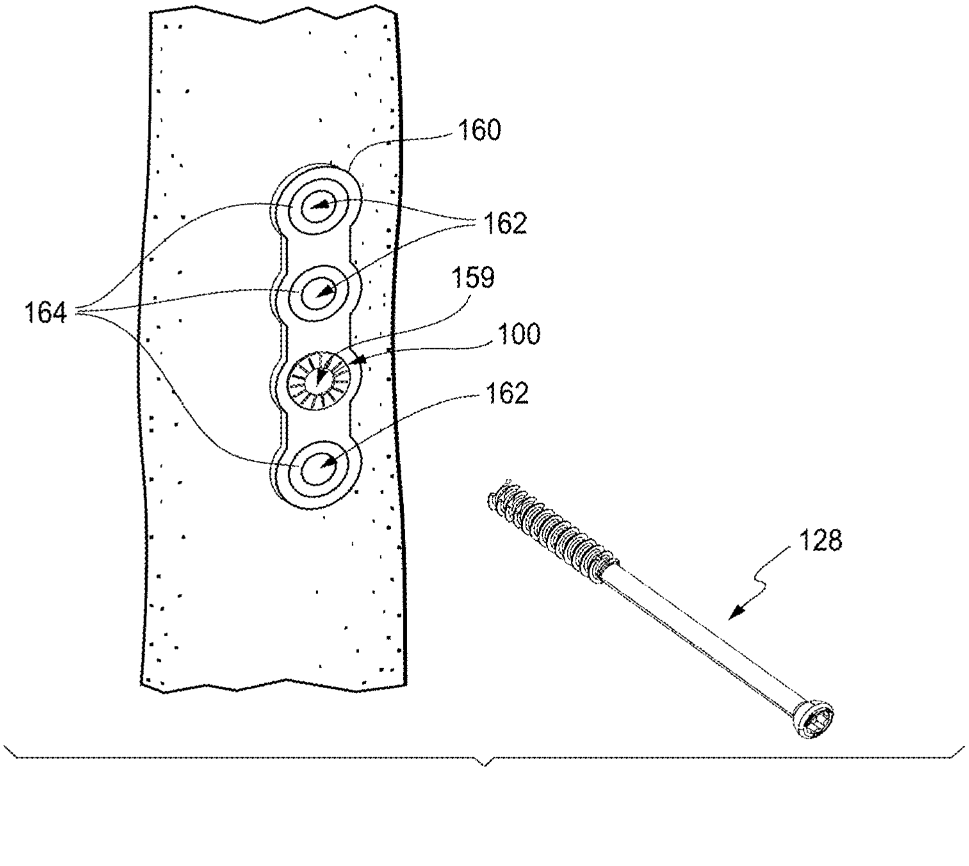
FIG. 14 is perspective view of the surgical region as shown in FIG. 13 illustrating the plate disposed on the bone and the compression device received in an opening of the bone plate.
Figure 15:
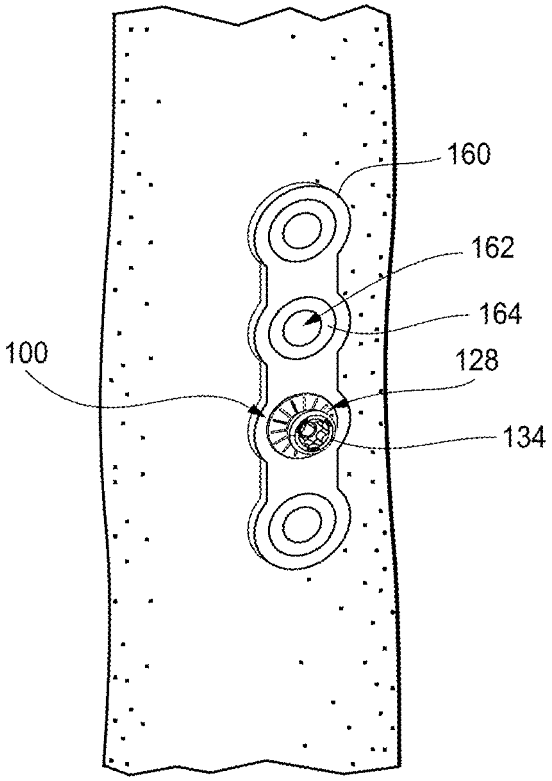
FIG. 15 is a perspective view depicting the surgical region as shown in FIGS. 13 and 14 after installation of the bone screw and compression of the compression device.

As indicated above, the compression device 100 provided herein may also be used in connection with a bone plate 160 as shown in FIGS. 13-15. Referring now to FIG. 13, the relative positioning of screw 128, the compression device 100, bone plate 160, and a bone segment are shown. A pilot hole 159 has been pre-drilled into the bone segment, and in some embodiments, may be drilled in connection with a guide wire and cannulated drill bit as described above. In some forms, the bone segment may have a fracture extending through a portion thereof. The bone plate 160 includes one or more openings 162 for receiving bone screws 128 therethrough to couple the bone plate 160 to the bone segment. In some forms, the compression device 100 may be sized to be at least partially received in a recessed portion 164 of the openings 162 of the bone plate 160. Additionally or alternatively, the compression device 100 and the openings 162 of the bone plate 160 may include mating structures to align and secure the compression device 100 therein.

In FIG. 14, the bone plate 160 has been positioned immediately adjacent the bone segment and the compression device 100 is shown seated in the recessed portion 164 of the opening 162. Thereafter, as shown in FIG. 15, the bone screw 128 may be advanced through the compression device 100 and into the pilot hole 159, through the opening 162 of the bone plate 160. The head portion 134 of the screw 128 is shown impinging upon, and compressing, the superelastic resilient teeth 110 of the compression device 100 while the teeth 110 exert an axial biasing force against the head portion 134. As illustrated, the compressed teeth 110 of the compression device 100 are in a flat configuration due to impingement of the head portion of the screw. In other forms, the teeth 110 of the compression device 100 may be compressed further into a concave configuration depending on the shape of the opening 162 and recessed portion 164 of the bone plate 160, as described in further detail above with respect to FIGS. 10-12.

Figure 16:
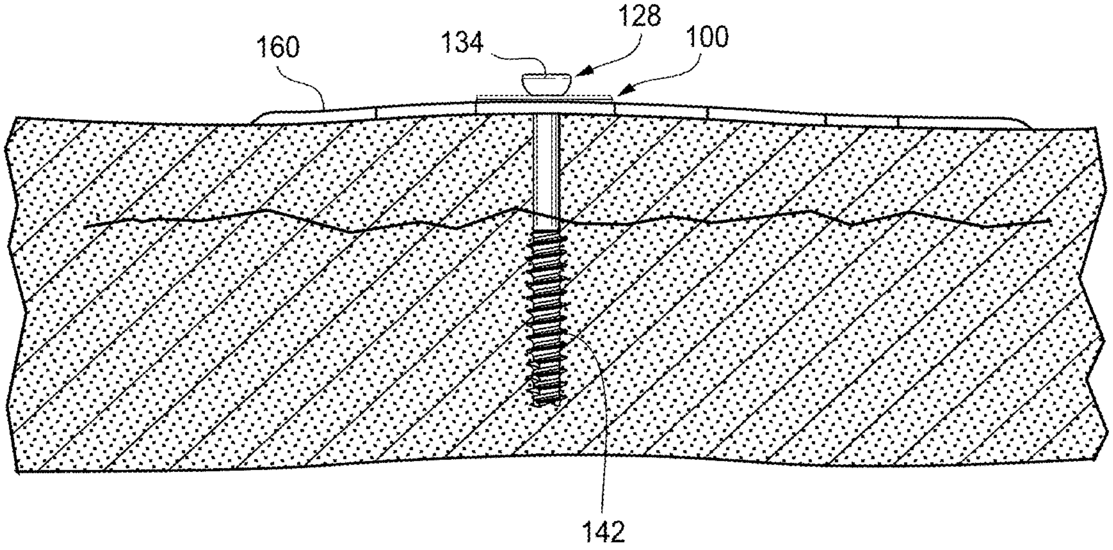
FIG. 16 is a cross-sectional view of a bone section of a patient with a bone plate, compression device, and bone screw illustrating deformation of the compression device via impingement of the head of the bone screw.

FIG. 16 depicts a bone plate 160 positioned between the compression device 100 and the surface of the bone. The threaded distal portion 142 of the screw 128 has been inserted through the opening 108 of the compression device 100 and opening 162 of the bone plate 160, and into the far portion of the bone. As shown, the screw 128 is compressing the two fractured portions of bone. In addition, the resilient teeth 110 of the compression device 100, compressed into the flat configuration, exert an axial biasing force on the head portion 134 of the screw 128.

Figure 17:
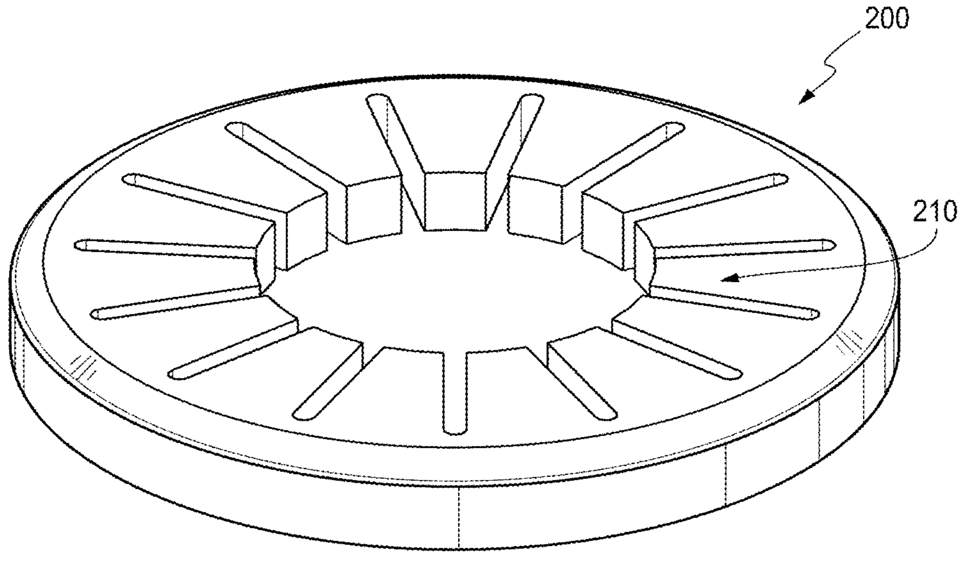
FIG. 17 is a perspective view of an alternative embodiment of a compression device.

Referring now to FIG. 17, an alternative compression device 200 having a substantially flat configuration in its resting state, unlike the convex compression device 100 illustrated in FIGS. 1-3. In other words, the compression device 200 is of a flat configuration when there is no force acting upon the superelastic, resilient teeth 210 thereof. As shown, the tip portion 223 of the teeth 210 does not extend proximally beyond the upper surface 204 of the peripheral portion 202 or distally beyond the lower surface of the peripheral portion 202. In such embodiments, the compression device 200 may be installed in a countersunk portion of bone, or a bone plate positioned adjacent the bone, such that the teeth 210 may be impinged upon and compressed by the head portion of a fastener such as bone screw 128.

Figure 18:
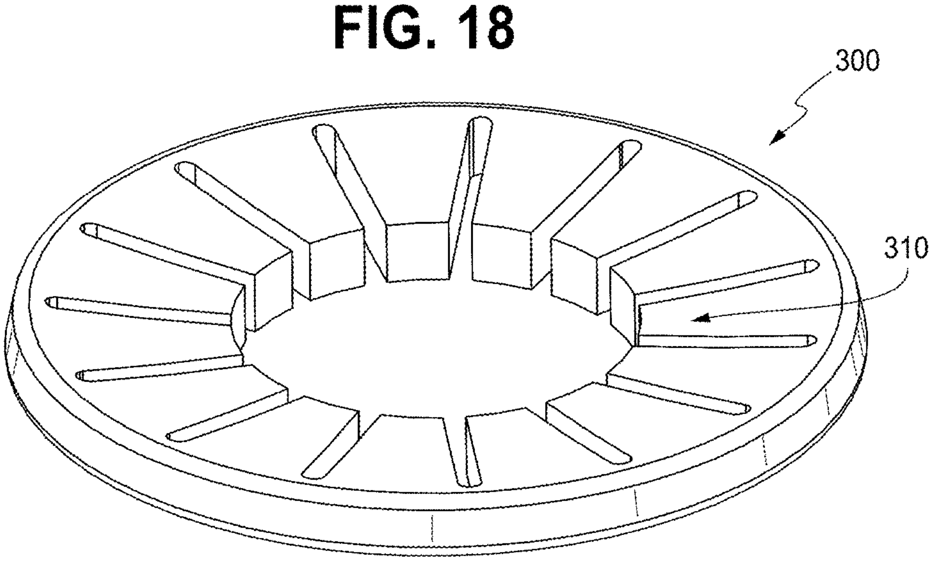
FIG. 18 is a perspective view of another alternative embodiment of a compression device.

FIG. 18 illustrates yet another embodiment of a compression device 300 having a substantially bowl-shaped or concave configuration in its resting state. So configured, the compression device 300 is in a concave configuration when there is no force acting upon the superelastic, resilient teeth 310 thereof. In other words, the tip portion 323 of the teeth 310 extends distally beyond the lower surface 306 of the peripheral portion 302. In such embodiments, the compression device 300 may be installed in a countersunk portion of bone, or a bone plate positioned adjacent the bone, such that the teeth 310 may be impinged upon and compressed by the head portion of a fastener such as bone screw 128.

Figure 19:
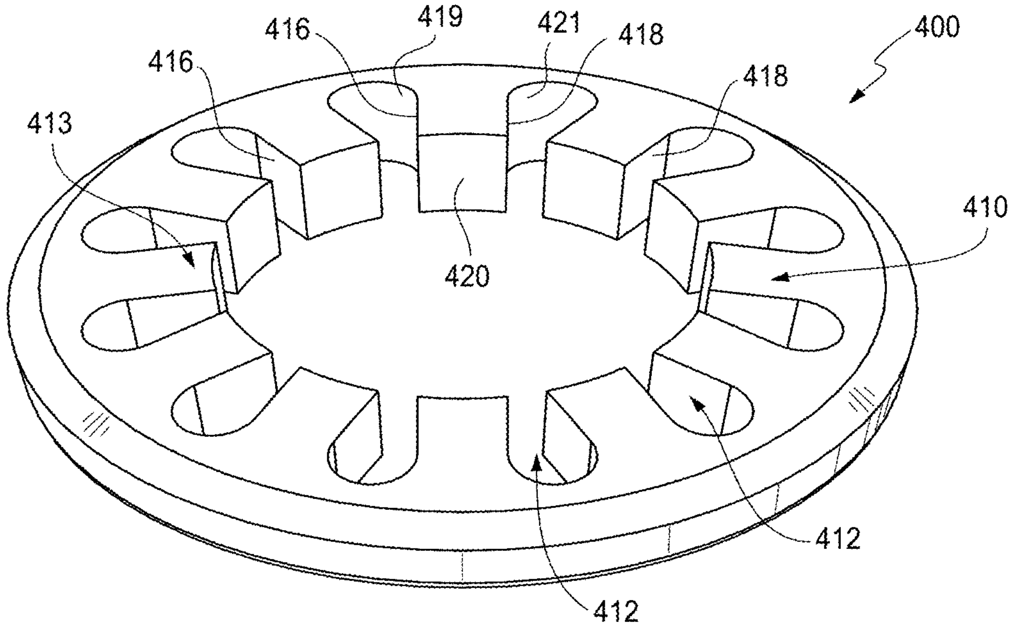
FIG. 19 is a perspective view of another alternative embodiment of a compression device.
Figure 20:
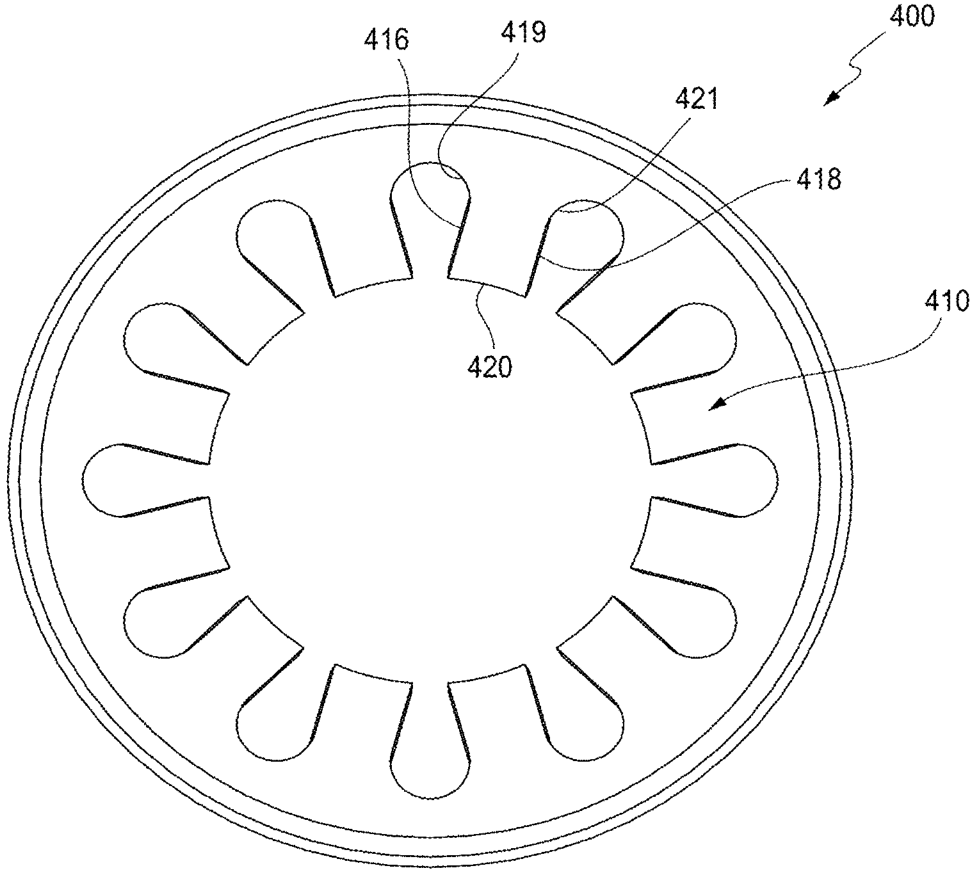
FIG. 20 is a top plan view of the compression device shown in FIG. 19.

As shown in FIGS. 19 and 20, alternatively a compression device 400 includes a plurality of teeth 410 that are shaped differently from the plurality of teeth 110, and therefore define gaps 412 having different shapes than the gaps 112. As shown, each tooth 412 has a cuboid projecting portion 413 with a first side edge 416, second side edge 418, and terminal side edge 420. Cusps 419, 421 are likewise of a different shape. As illustrated, teeth 410 define gaps 412 that have a curved surface 421. Compression device 400 is of a convex configuration and the teeth 410 are configured to exert a biasing force in an axial direction when deformed in an opposing axial direction. The compression device 400 can also be positioned in a countersunk hole in a portion of bone, or used in connection with a bone plate such as bone plate 160 or 702.

Figure 21:
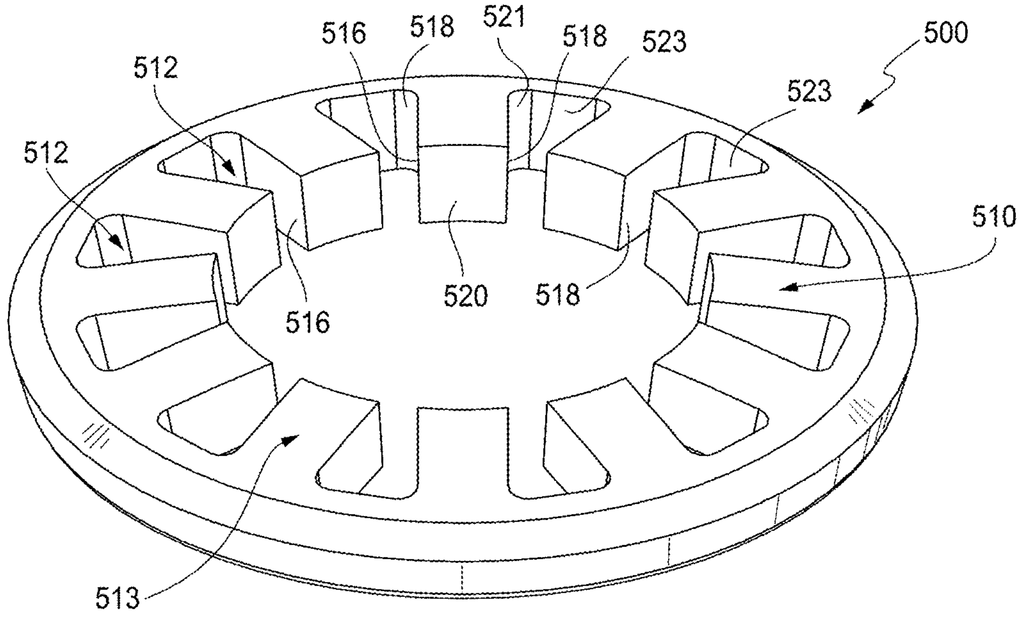
FIG. 21 is a perspective view of yet another alternative embodiment of a compression device.
Figure 22:
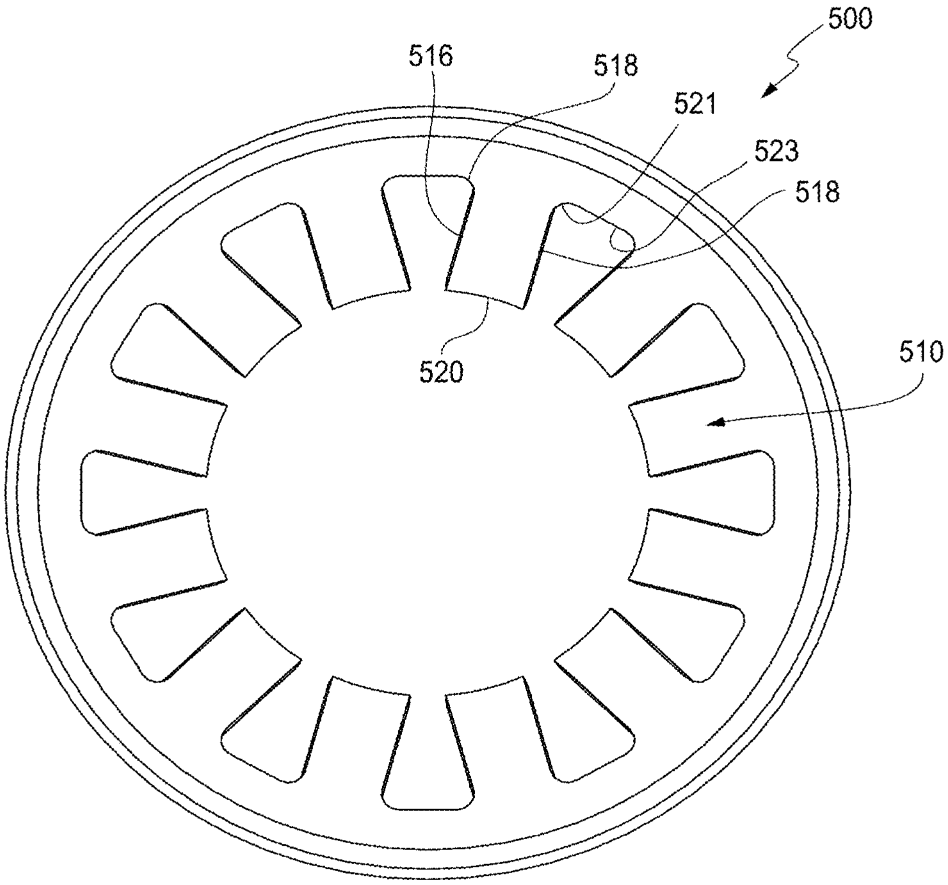
FIG. 22 is a top plan view of the compression device shown in FIG. 21.

As shown in FIGS. 21 and 22, compression device 500 includes teeth 510 that define gaps 512 having different shapes from the gaps 112. As shown, each tooth 512 has a cuboid projecting portion 513 with a first side edge 516, second side edge 518, and terminal side edge 520. As illustrated, the first and second side edges 516, 518 define gaps 512 terminate in a generally flat region 523. Cusps 519, 521 are likewise of a different shape. Compression device 500 is of a convex configuration and the teeth 510 are configured to exert a biasing force in an axial direction when deformed in an opposing axial direction.

Figure 23:
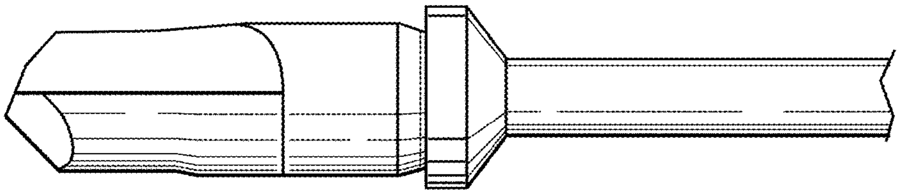
FIG. 23 illustrates a countersink tool in the form of a drill or drill bit.

FIG. 23 illustrates a countersink tool showing a drill bit that may be used to cut a countersunk bore in a surface of a bone segment. Such a countersink tool may be provided in connection with one or more compression devices within a kit, as described above. The size of the drill bit of the countersink tool may be selected such that the countersunk bore drilled thereby is sized to at least partially receive the compression device 100 (e.g., the resilient teeth 110) within. In some forms, different size drill bits or different countersink tools may be selected depending on the surgical indication or depending on the diameter of the compression device employed.

Although the illustrated example in FIGS. 4-7 depicts a subtalar fusion using a lag-type screw 128, the compression device 100 provided herein may be used in a variety of orthopedic applications. Such a compression device 100 could be provided for use in connection with other fasteners to stabilize any fracture or joint, and the usage is not limited to the example procedures described herein. For example, the compression device 100 may be used in connection with a cannulated screw for hip fracture repair, among other indications. The fastener in the form of threaded screw 128 may alternatively be a fully threaded bone screw, and the method of installation thereof may include drilling pilot hole having a larger diameter than the threads of the bone screw in a near bone segment, and a pilot hole having a narrower diameter than the threads of the bone screw in a far bone segment, such that compression may likewise be achieved therebetween.

FIGS. 24-28 illustrate an embodiment of a bone plate assembly 700 including a convex-shaped compression device 400 (as illustrated in FIGS. 19 and 20) and a bone plate 702. The bone plate includes a plate body 704 including an upper plate surface 706, a lower plate surface 708, an aperture 710 through the plate body. A countersunk region 712 is formed about the aperture and opens to the upper plate surface. In FIGS. 24 and 26-28, the compression device 400 is captively retained within the countersunk region.

Figure 25:
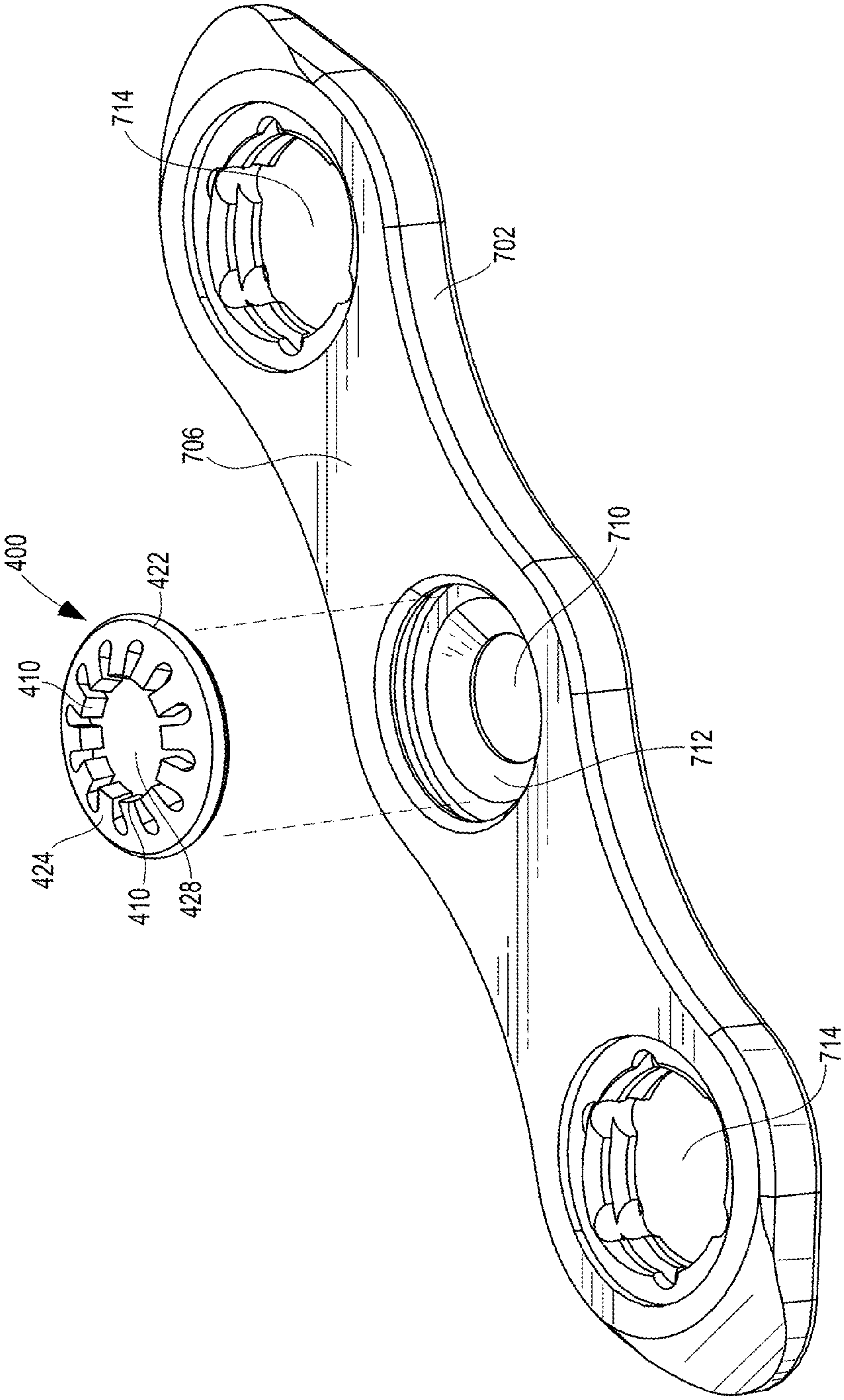
FIG. 25 is an exploded view of the bone plate assembly shown in FIG. 24.
Figure 26:
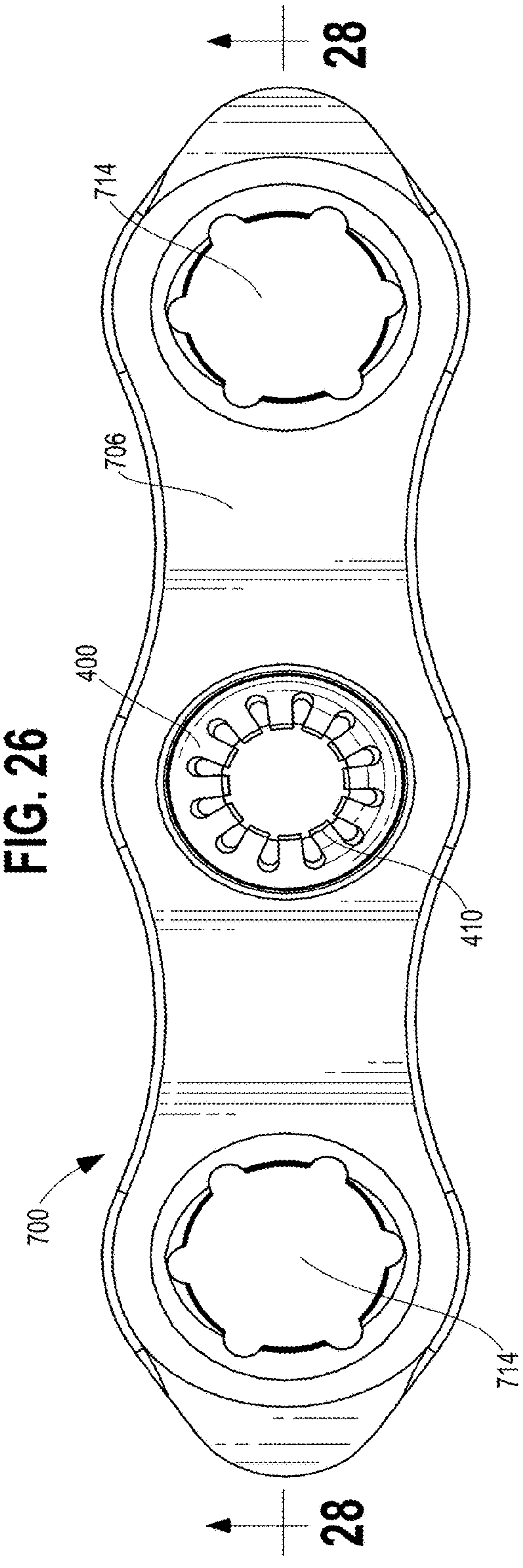
FIG. 26 is a top plan view of the bone plate assembly shown in FIG. 24.
Figure 27:
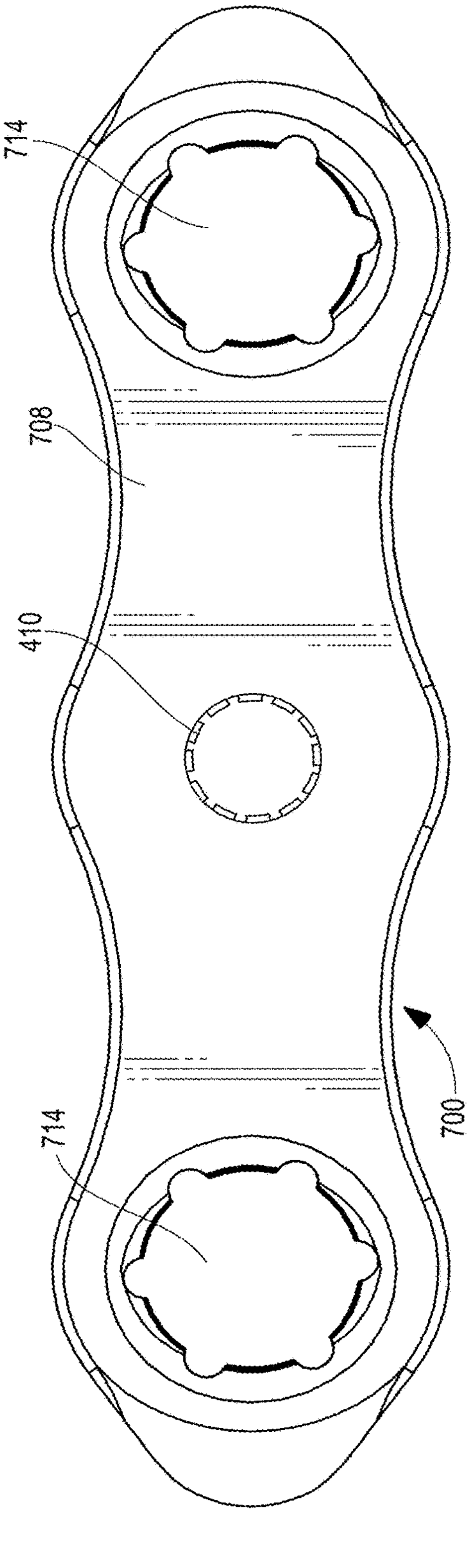
FIG. 27 is a bottom plan view of the bone plate shown in FIG. 26.

As shown in more detail in the exploded view of FIG. 25, the compression device 400 includes a plurality of teeth 410 and is provided with peripheral portion 422 in the form of a generally annular ring having an upper surface 424, and a central opening 428 extending therethrough. Tips of the teeth 410 form the central opening 428.

The bone plate further includes one or more fixation openings 714 for receiving fixation fasteners therethrough to couple the bone plate 702 to a bone segment and prevent rotation or other movement of the bone plate. Generally, a fixation fastener (e.g., screw, nail, etc.) can be of the same as or different from a fastener used to compress one or more resilient structures of a compression device, or compress one or more resilient structures integrally formed with a bone plate, as described herein. For example, a fixation fastener can be cannulated or un-cannulated (solid core), a fixation fastener can also be fully threaded or lag-type. Generally, any combination of the same or different fasteners and fixation fasteners can be utilized with a bone plate. The openings 714 can be configured in a number of forms. Generally, a bone plate can have any configuration (e.g., L-shaped, H-shaped, cross-shaped, etc.) and include any number (e.g., 1, 2, 3, 4, 5, etc.) of apertures 710 for screws (e.g., lag screws) and any number (e.g., 0, 1, 2, 3, 4, 5, etc.) of fixation openings 714 for fixation fasteners.

Figure 28:
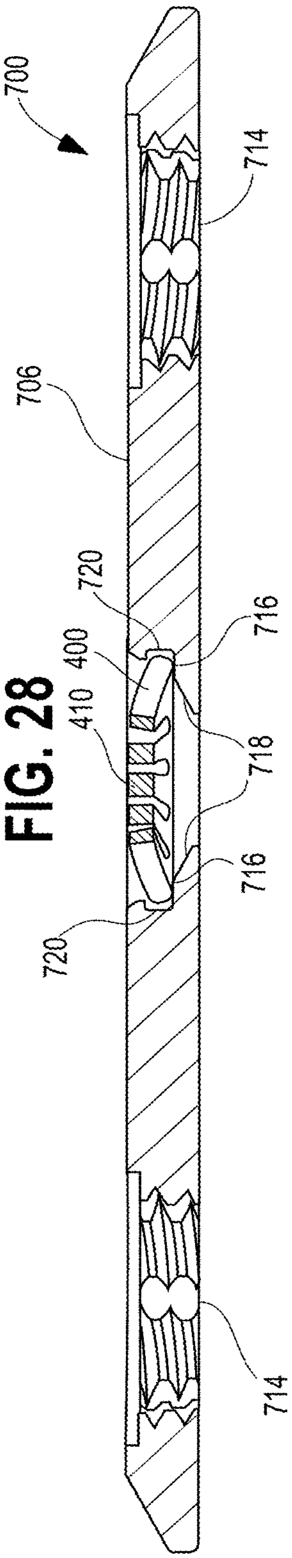
FIG. 28 is a cross-sectional view taken along line 28-28 in FIG. 26.

As shown in the cross-sectional view of FIG. 28, the countersunk region includes an intermediate seat region 716 sized to seat the compression device 400. The intermediate seat region has a continuous annular ledge formed along an inner intermediate surface of the countersunk region 712. However, other structures of the intermediate seat region (e.g., discrete tabs radially spaced around the inner intermediate surface) can provide surfaces to seat a compression device. A bottom portion 718 of the countersunk region 712 is concave relative to the upper plate surface 706. In other embodiments, the bottom portion of the countersunk region can have other forms such as a flat configuration spaced distally from the intermediate seat region.

The compression device 400 is captively retained within the countersunk region 712 by a mating structure that includes an intermediate annular recessed region 720, which is also formed on the inner intermediate surface of the countersunk region. The intermediate annular recessed region 720 is spaced from the intermediate seat region 716 to provide a gap that is sized to receive and retain the peripheral portion 422 of the compression device. In this configuration, tip portions of the teeth 410 of the compression device extend proximally beyond the upper surface 424 of the peripheral portion 422 in an unbiased state. The teeth 410 also extend toward the upper plate surface 706 of the bone plate (i.e., in a convex structure relative to the upper plate surface). In other embodiments disclosed hereinbelow, a bone plate assembly can include a compression device where tip portions of the teeth extend medially (i.e., having a flat structure) in an unbiased state, or extend distally beyond the lower surface of the peripheral portion of the compression device in an unbiased state (i.e., having a concave structure relative to the upper plate surface).

Figure 24:
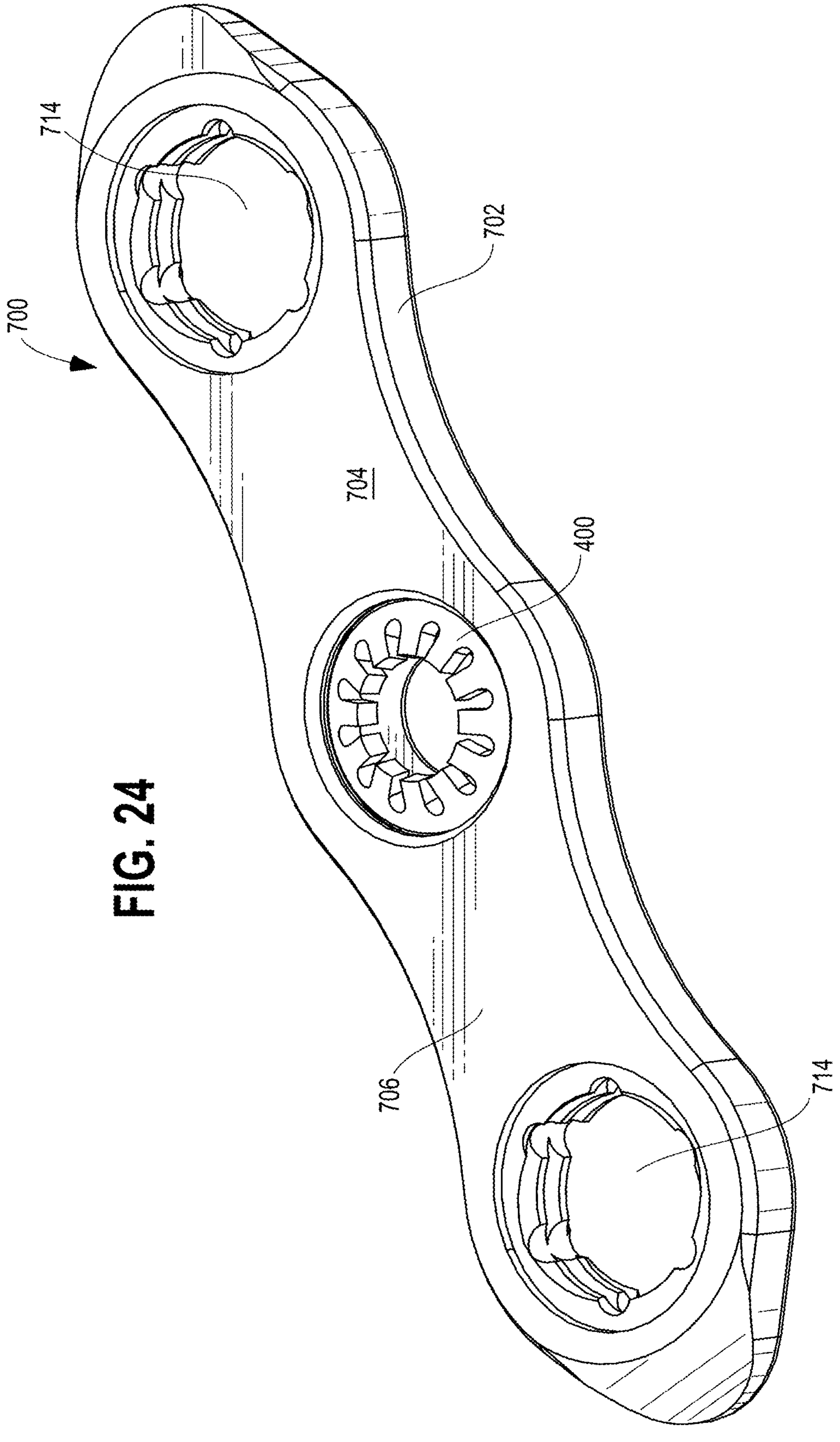
FIG. 24 is a perspective view of an embodiment of a bone plate assembly in accordance with an alternative plate embodiment.
Figure 29:
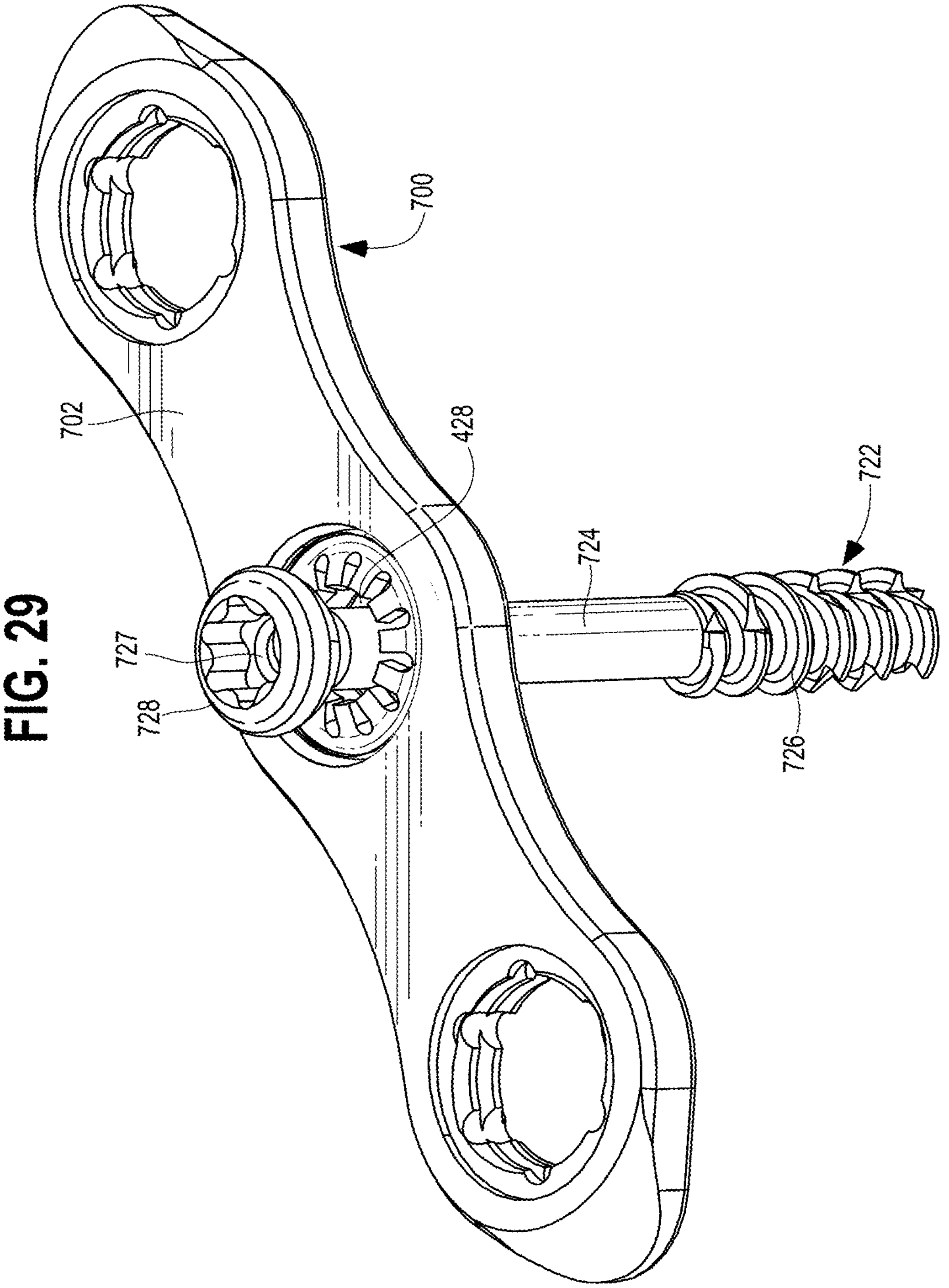
FIG. 29 is a perspective view of a kit that includes the bone plate assembly of FIG. 24 and a bone screw, the bone screw having been placed into the bone plate assembly.

FIG. 29 shows a kit including the bone plate assembly of FIG. 24 and a lag type bone screw 722. The bone screw 722 is positioned through the opening 728 of the compression device 400 and the aperture of the bone plate 702. The bone screw 722 includes an unthreaded proximal shaft portion 724, a threaded distal shaft portion 726, and a head portion 728. The head portion includes a socket 727 sized and shaped to accommodate an insertion tool (not shown).

Figure 30:
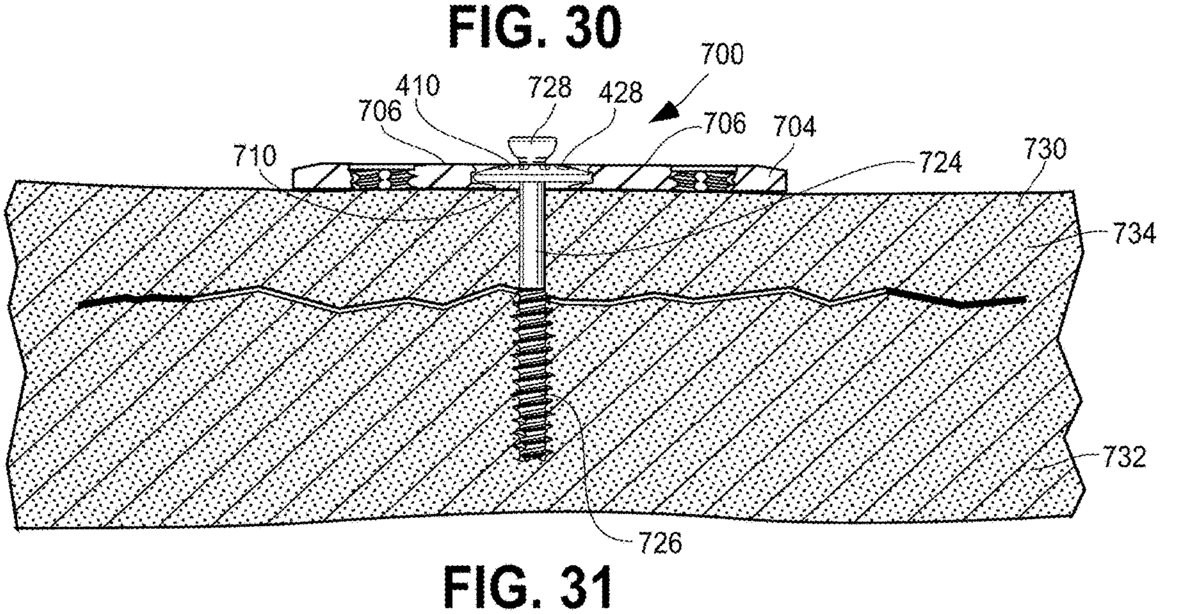
FIG. 30 is a cross-sectional view of an embodiment of a bone plate assembly disposed on a bone section of a patient with a compression device captively retained within the bone plate assembly during the process of advancing the bone screw but prior to impingement of the head of the bone screw on the compression device.
Figure 31:
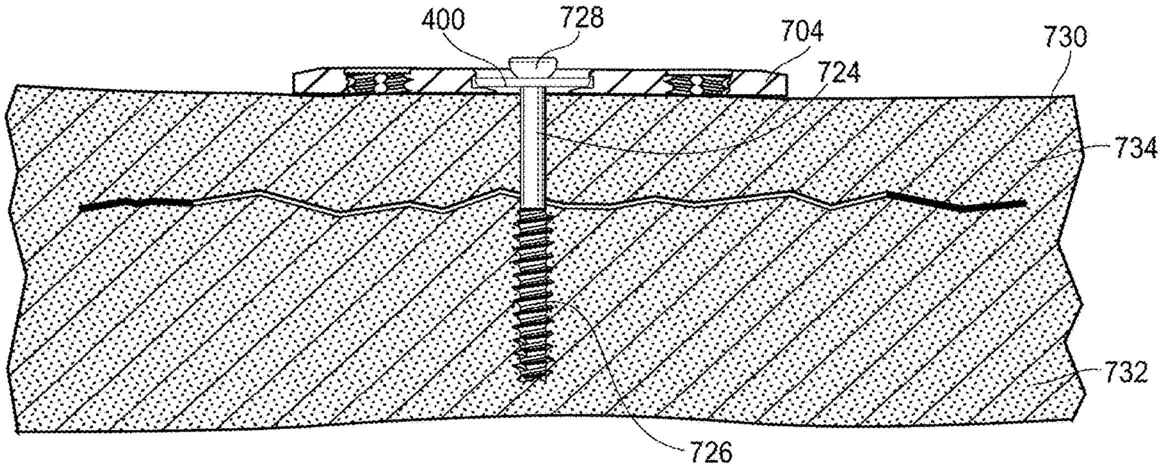
FIG. 31 is a cross-sectional view of the bone plate assembly and bone section shown in FIG. 30, at a further point during the process of advancing the bone screw and illustrating impingement of the head of the bone screw on the compression device.
Figure 32:
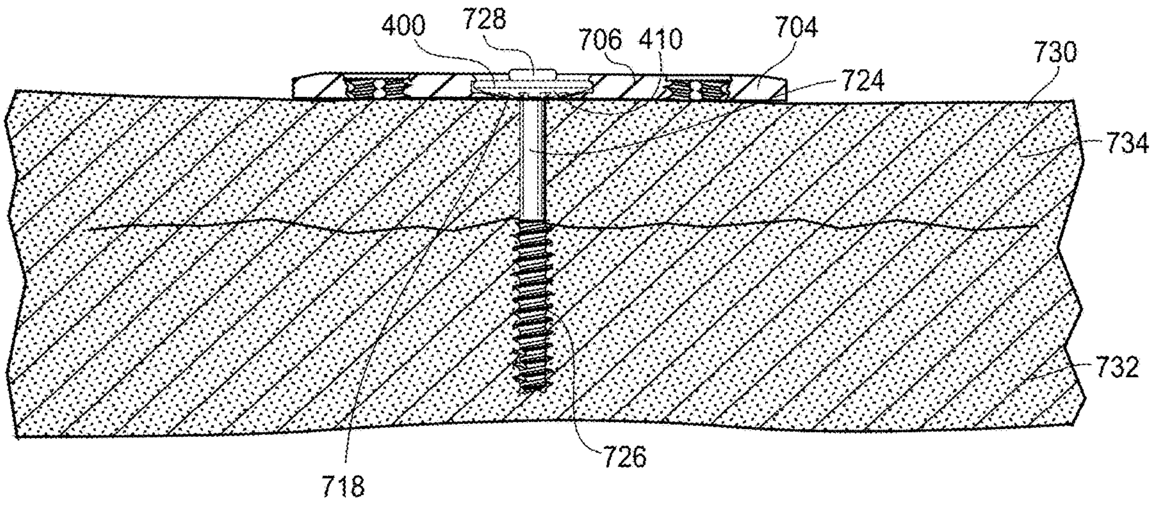
FIG. 32 is a cross-sectional view of the bone plate assembly and bone section shown in FIG. 30, at a final point during the process of advancing the bone screw and illustrating impingement of the head of the bone screw on the compression device.

FIGS. 30-32 illustrate cross-sectional views of the bone plate assembly 700 and lag type bone screw 722 at separate times during progressive advancement of the screw into a patient's surgically exposed bone segment 730. In FIG. 30, the threaded and unthreaded shaft portions 724 and 726 of the screw have been passed through the opening 428 of the compression device 400 (of generally convex structure) and the aperture 710 of the plate body 704. The threaded shaft portion 726 of the screw is sunken into a distal fragment 732 the bone segment 730, and the unthreaded shaft portion 724 passes through a proximal fragment 734 of the bone segment. The head portion 728 of the screw is positioned proximal to the upper plate surface 706 and adjacent to the unbiased teeth 410 of the compression device 400. Upon advancement of the screw as shown in FIG. 31, the shaft portions 724 and 726 of the screw travel further into the bone segment and the head portion 728 impinges onto the teeth 410 of the compression device. In this state, the teeth are deformed by the head portion and exert a biasing force against the head portion. FIG. 32 illustrates a stage of further advancement of the screw where the head portion 728 further compresses the teeth 410 to the bottom portion 718 of the countersunk region 712, such that the teeth are deformed into a concave configuration relative to the upper plate surface 706. In the configuration in FIG. 32, the teeth 410 continue to exert biasing forces against the head portion 728 of the screw and the distal fragment 732 is compressed against the proximal fragment 734 of the bone segment 730.

Figure 33:
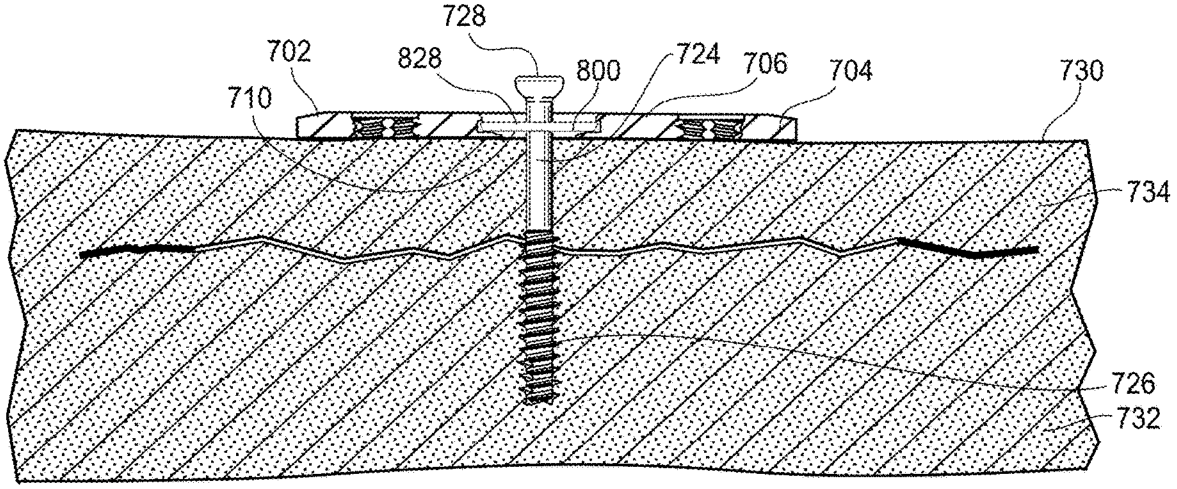
FIG. 33 is a cross-sectional view of an alternative embodiment of a bone plate assembly disposed on a bone section of a patient with a compression device captively retained within the bone plate assembly during the process of advancing the bone screw but prior to impingement of the head of the bone screw on the compression device.
Figure 34:
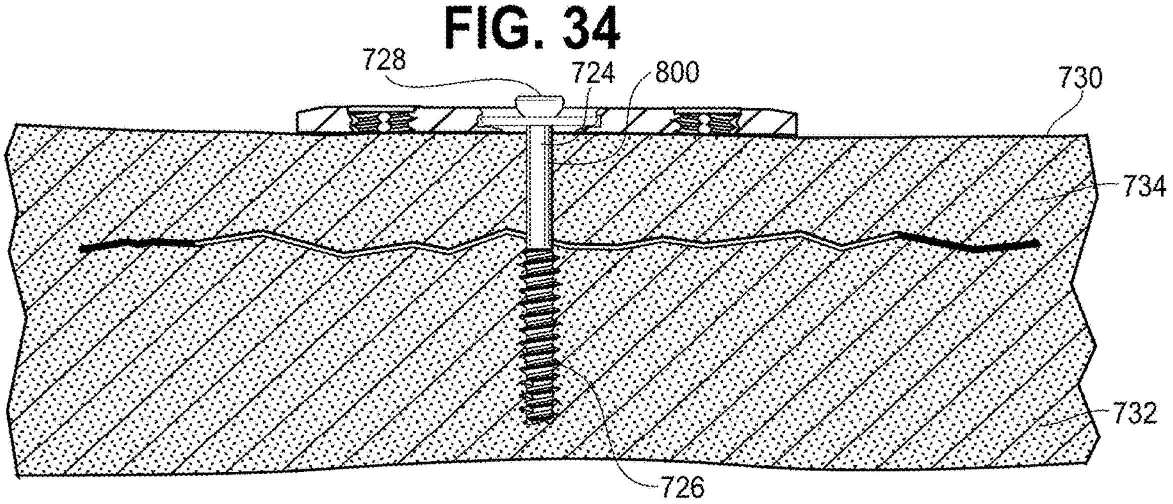
FIG. 34 is a cross-sectional view of the bone plate assembly and bone section shown in FIG. 33, at a further point during the process of advancing the bone screw and illustrating impingement of the head of the bone screw on the compression device.
Figure 35:
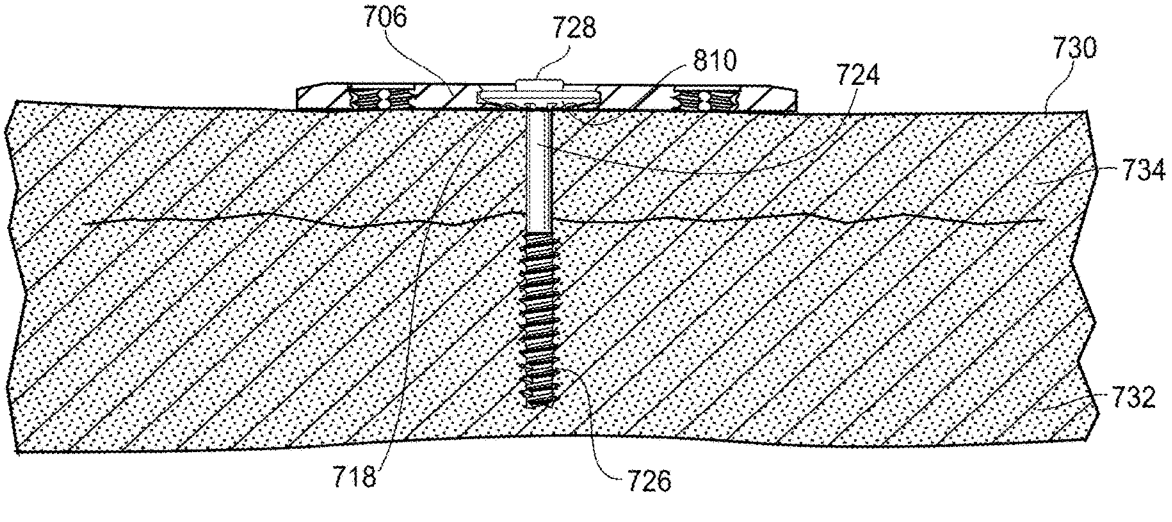
FIG. 35 is a cross-sectional view of the bone plate assembly and bone section shown in FIG. 33, at a final point during the process of advancing the bone screw and illustrating impingement of the head of the bone screw on the compression device.

FIGS. 33-35 illustrate cross-sectional views of another embodiment of a bone plate assembly and lag screw, again at sequential points during progressive advancement of the screw into patient bone. In this embodiment, the compression device is again held captively within the bone plate 702. Unlike the embodiment illustrated in FIGS. 24-32, the compression device 800 (of generally flat structure) includes a plurality of teeth 810 where tip portions of the teeth extend medially from the peripheral portion of the compression device in an unbiased state (much like tip portions of the teeth 223 of the compression device 200 illustrated in FIG. 17). FIG. 33 illustrates a state of advancement of the screw where the unthreaded 724 and threaded 726 shaft portions of the screw have been passed through the opening 828 of the compression device and the aperture 710 of the plate body. The threaded shaft portion 726 of the screw is sunken into a distal fragment 732 the bone segment 730, and the unthreaded shaft portion 724 passes through a proximal fragment 734 of the bone segment. FIG. 34 illustrates a state of further advancement of the screw into the bone, where the head portion 728 is partially within the countersunk region of the plate body and contacting the unbiased teeth (not shown) of the compression device. FIG. 35 illustrates a state of even further advancement of the screw into the bone segment where the head portion 728 compresses the teeth 810 into the bottom portion 718 of the countersunk region, such that the teeth are deformed into a concave configuration relative to the upper plate surface 706. The teeth 810 in FIG. 35 continue exert biasing forces against the head portion 728 of the screw and the distal fragment 732 is compressed against the proximal fragment 734 of the bone segment 730.

Figure 36:
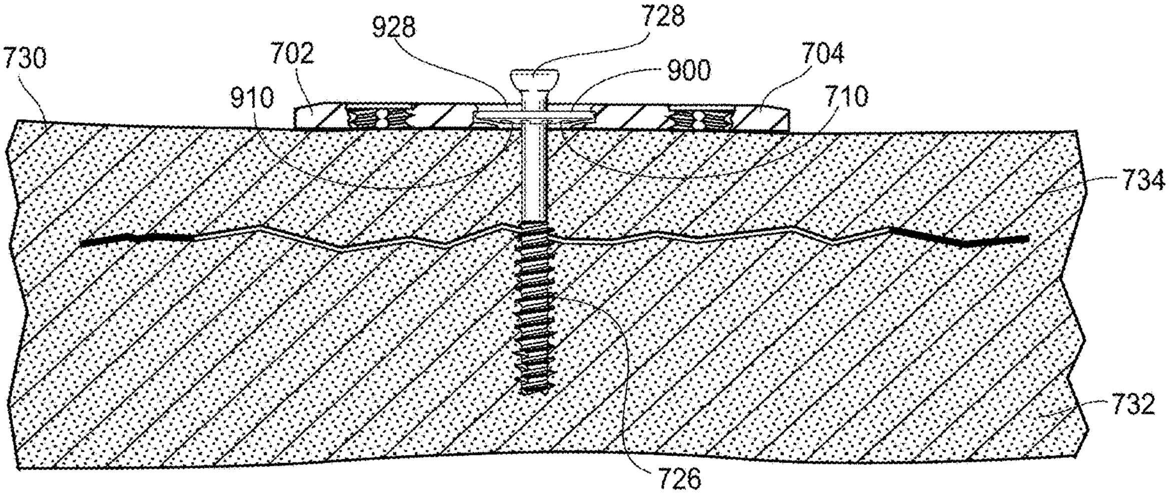
FIG. 36 is a cross-sectional view of yet another alternative embodiment of a bone plate assembly disposed on a bone section of a patient with a compression device captively retained within the bone plate assembly during the process of advancing the bone screw but prior to impingement of the head of the bone screw on the compression device.
Figure 37:
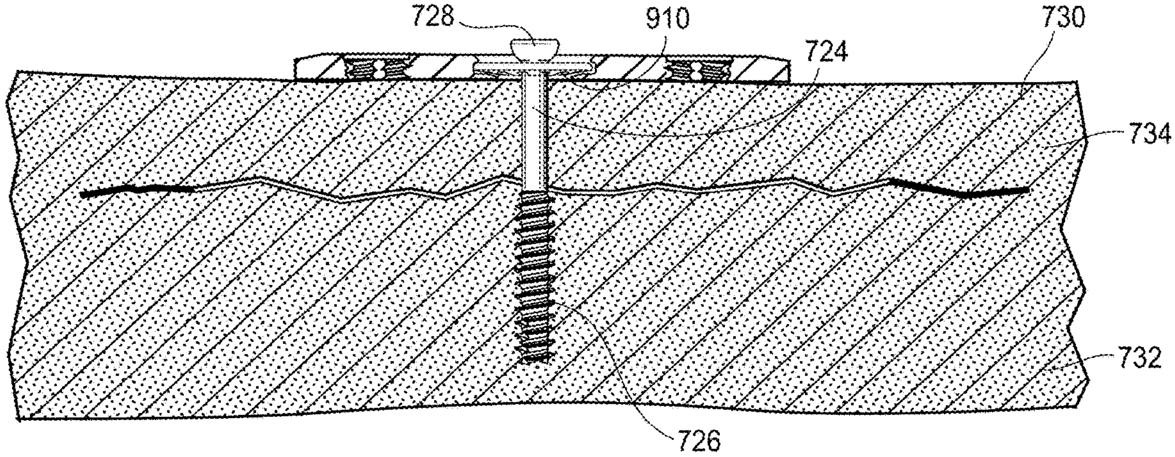
FIG. 37 is a cross-sectional view of the bone plate assembly and bone section shown in FIG. 36, at a further point during the process of advancing the bone screw.
Figure 38:
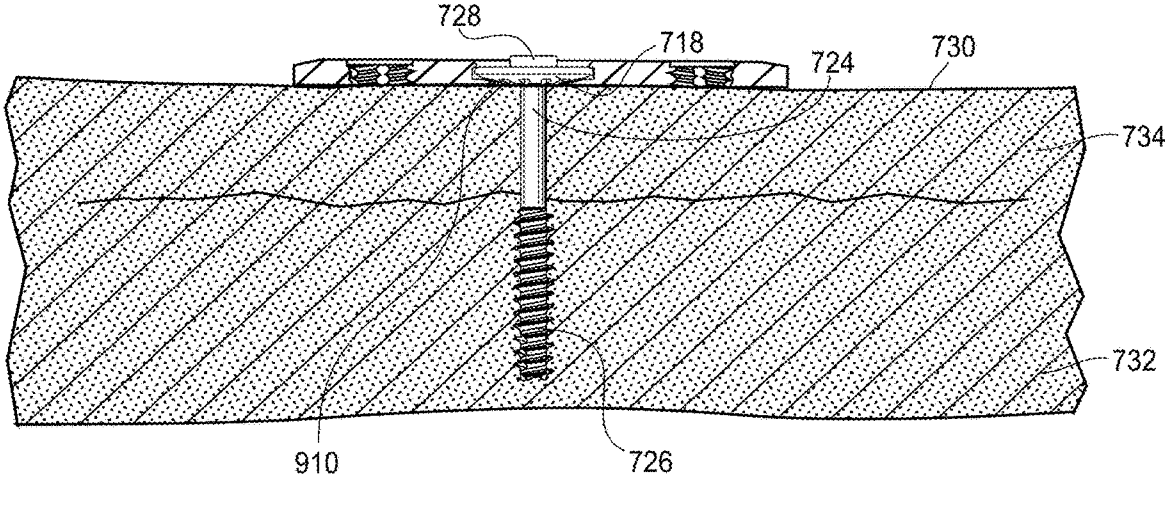
FIG. 38 is a cross-sectional view of the bone plate assembly and bone section shown in FIG. 36, at a final point during the process of advancing the bone screw and illustrating impingement of the head of the bone screw on the compression device.

FIGS. 36-38 illustrate yet another embodiment of a bone plate assembly and lag screw at various stages of advancement of the screw into patient bone. Again, the compression device 900 is held captively within the bone plate 702.

Unlike the embodiments illustrated in FIGS. 24-35, the compression device 900 (of generally concave structure) includes a plurality of teeth 910 where the tip portions of the teeth extend distally beyond the lower surface of the peripheral portion of the compression device in an unbiased state (much like tip portions of the teeth 323 of the compression device 300 illustrated in FIG. 18). FIG. 36 illustrates a state of advancement of the screw where the unthreaded 724 and threaded 726 shaft portions of the screw have been passed through the opening 928 of the compression device 900 and the aperture 710 of the plate body 704. The threaded shaft portion 726 of the screw is sunken into a distal fragment 732 the bone segment 730, and the unthreaded shaft portion 724 passes through a proximal fragment 734 of the bone segment. FIG. 37 illustrates a state of further advancement of the screw into the bone, where the head portion 728 of the screw is partially within the countersunk region of the plate body. FIG. 38 illustrates a state of even further advancement of the screw into the bone segment where the head portion 728 has impinged upon and compresses the teeth 910 to the bottom portion 718 of the countersunk region, such that the teeth are deformed into an even deeper concave configuration relative to the unbiased state of the teeth shown in FIGS. 36 and 37. The teeth 910 in FIG. 38 continue to exert biasing forces against the head portion 728 of the screw and the distal fragment 732 is compressed against the proximal fragment 734 of the bone segment 730.

Figure 39:
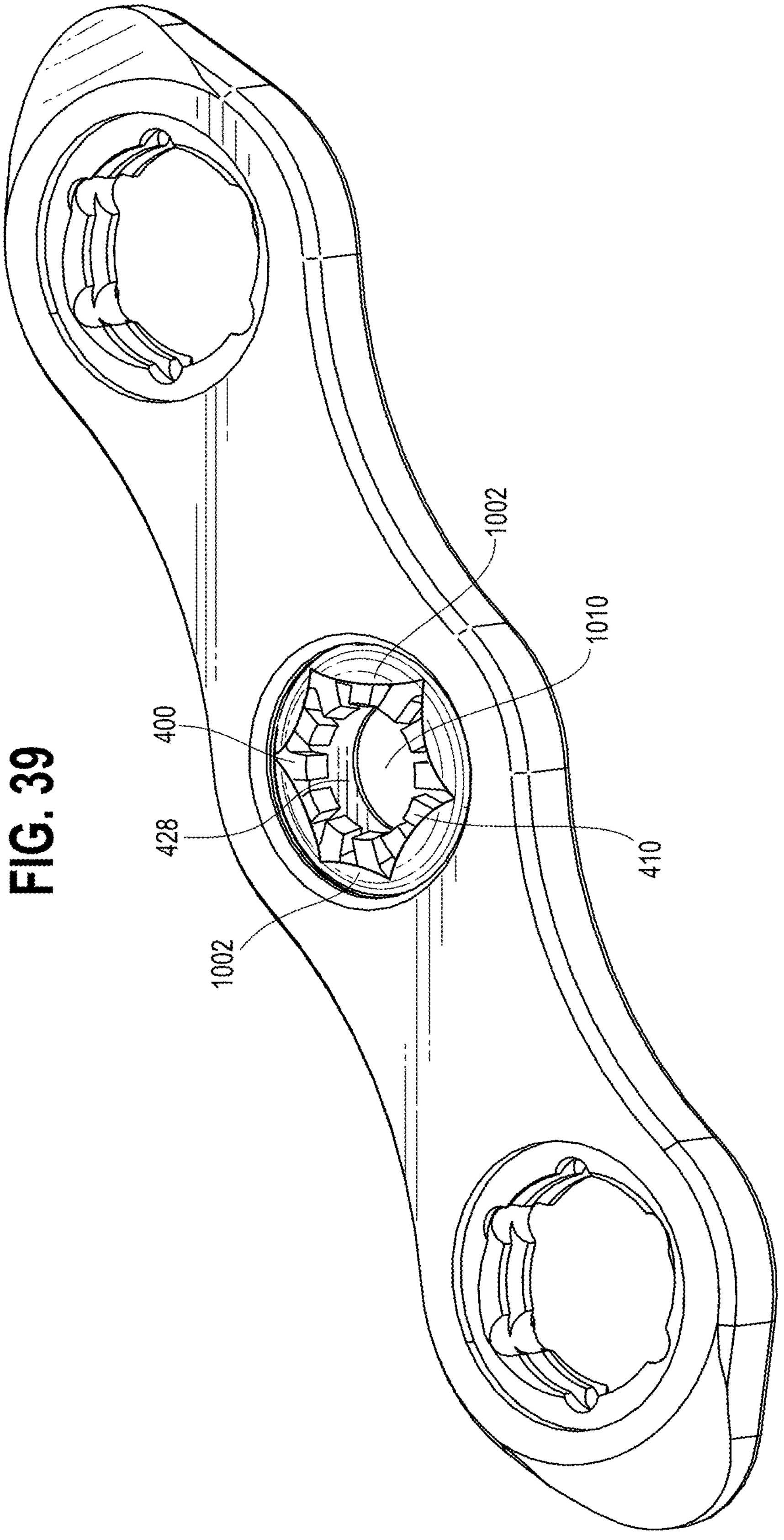
FIG. 39 is a perspective view of yet another alternative embodiment of a bone plate assembly comprising a mating structure including a plurality of lobes.

The alternative bone plate assembly 1000 of FIG. 39 comprises a mating structure that includes a plurality of lobes 1002 that protrude inwardly from the inner intermediate surface of the countersunk region. The lobes serve to captively retain the compression device 400 (of generally convex structure) while leaving exposed the opening 428 and teeth 410 of the compression device and the aperture 1010 of the bone plate assembly. The lobes can also be configured to mate with compression devices of generally concave and flat structures.

Figure 40:
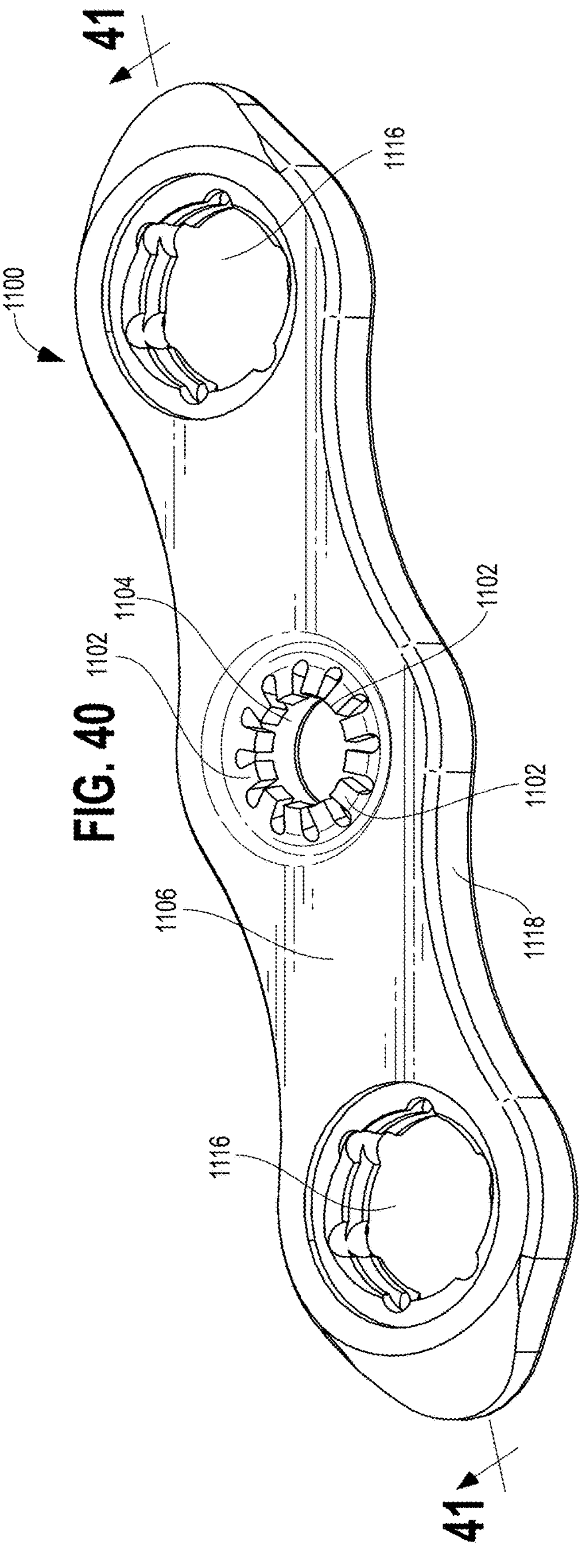
FIG. 40 is a perspective view of a first alternative embodiment of a bone plate having an integral compression structure.
Figure 41:
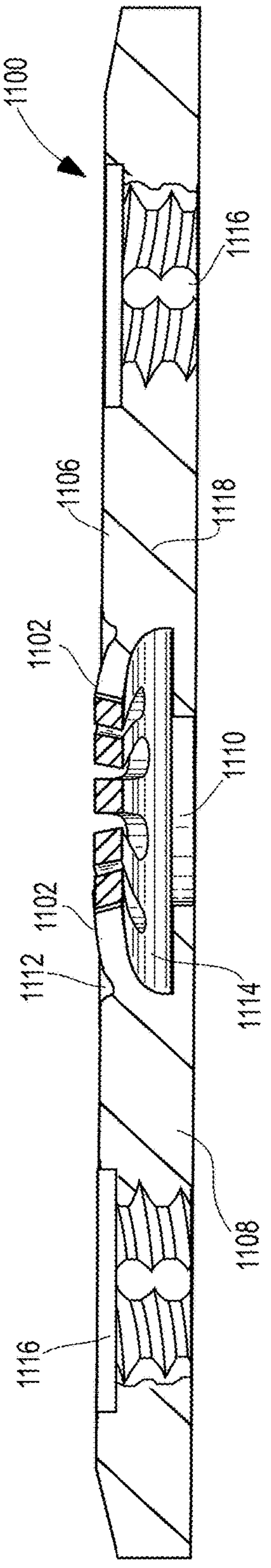
FIG. 41 is a cross-sectional view taken along line 41-41 in FIG. 40.

FIG. 40 is a perspective view, and FIG. 41 is a cross-sectional view (taken along line 41-41 in FIG. 40), of a first alternative embodiment of a bone plate 1100 having a plurality of inwardly projecting resilient teeth 1102. The teeth are integrally formed with the plate body 1118 at points of integration around an inner peripheral surface of an aperture 1110 through the plate body 1118. The teeth extend both toward an axis of the aperture 1110 and toward an upper plate surface 1106 of the plate body. In this configuration, the teeth 1102 generally form a convex structure relative to the upper plate surface 1106. Tips of the teeth 1102 converge to form an opening 1104 having a diameter through which the shaft of a fastener (e.g., a lag type bone screw) can pass. The diameter of the opening 1104 is also sized to permit the head of the fastener to impinge upon and deform the teeth 1102 from the upper plate surface 1106 side of the bone plate 1100 and toward the lower plate surface 1108, upon advancement of the fastener into a bone segment. Both an upper countersunk region 1112 and a lower countersunk region 1114 are formed about the aperture 1110. The bone plate further includes fixation openings 1116 configured to receive fixation fasteners (e.g., fixation screws) for securing the bone plate to a surface of a bone segment.

Figure 42:
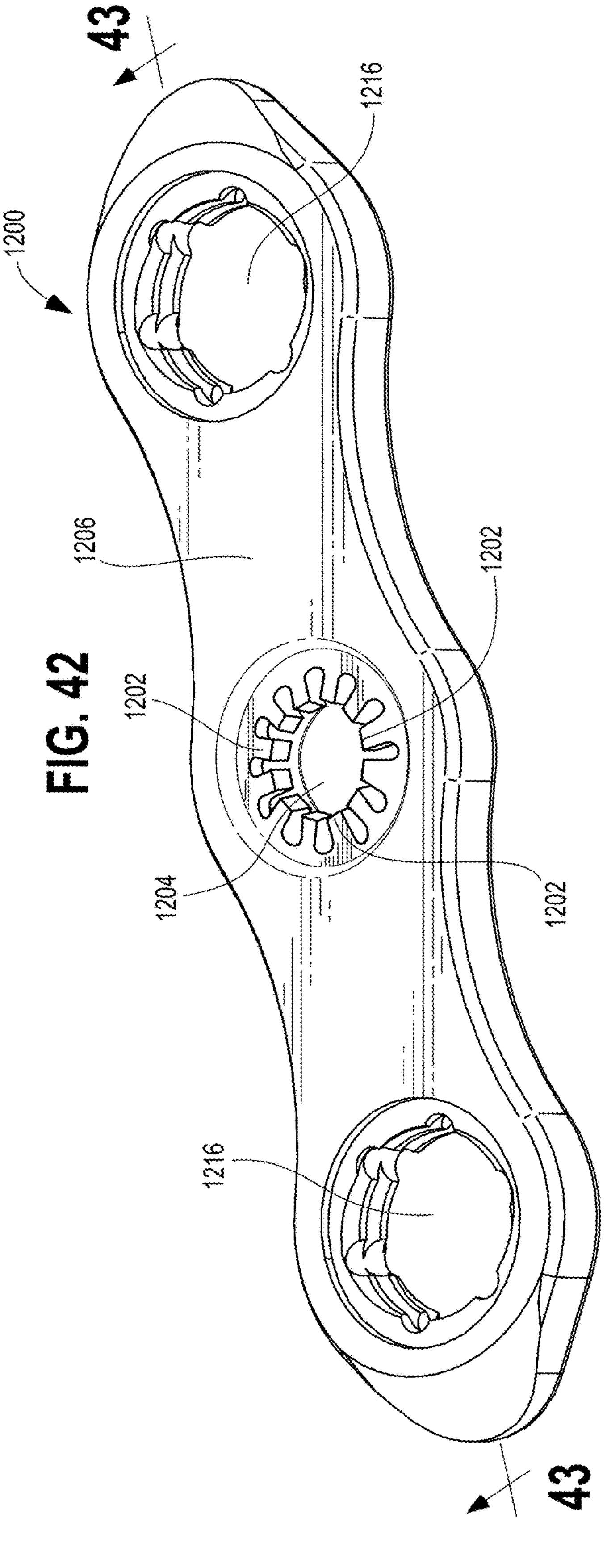
FIG. 42 is a view of a second alternative embodiment of a bone plate having an integral compression structure.
Figure 43:
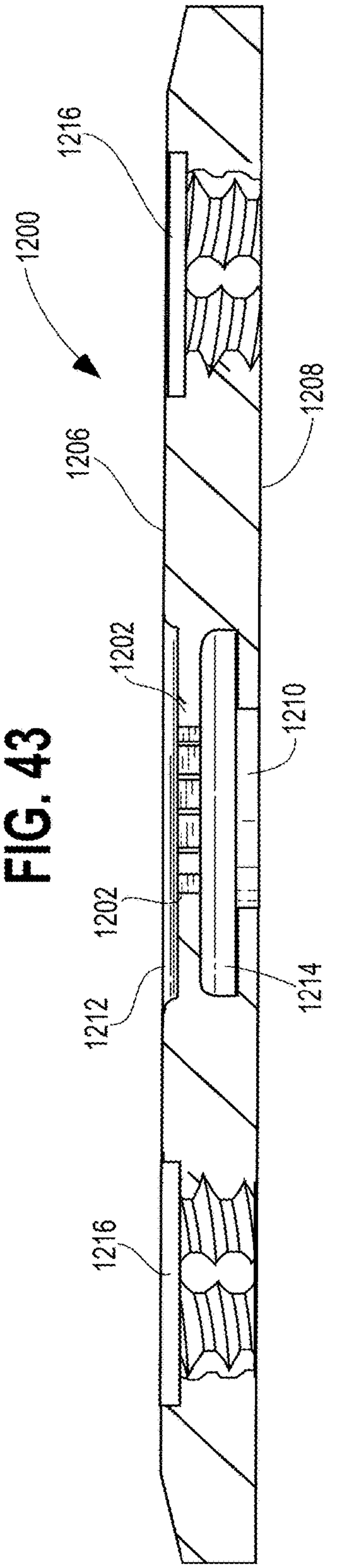
FIG. 43 is a cross-sectional view taken along line 43-43 in FIG. 42.

FIG. 42 is a perspective view, and FIG. 43 is a cross-sectional view (taken along line 43-43 in FIG. 42), of a second alternative embodiment of a bone plate 1200 having a plurality of inwardly projecting resilient teeth 1202. Like the first embodiment in FIGS. 40 and 41, the teeth are integrally formed with the plate body 1218 at points of integration around an inner peripheral surface of an aperture 1210. The teeth 1202 also extend toward an axis of the aperture 1210 and extend medially in a generally flat structure relative to the upper plate surface 1206. An opening 1204 is formed by tips of the teeth and has a diameter allowing a shaft of a fastener to pass therethrough. The opening 1204 also permits the head of the fastener to impinge upon and deform the teeth 1202 from the upper plate surface 1206 side of the bone plate 1200 and toward the lower plate surface 1208, upon advancement of the fastener into a bone segment. The plate 1200 further includes an upper countersunk region 1212 and a lower countersunk region 1214 formed about the aperture 1210. Fixation openings 1216 are provided to receive fixation fasteners for securing the bone plate to a surface of a bone segment.

Figure 44:
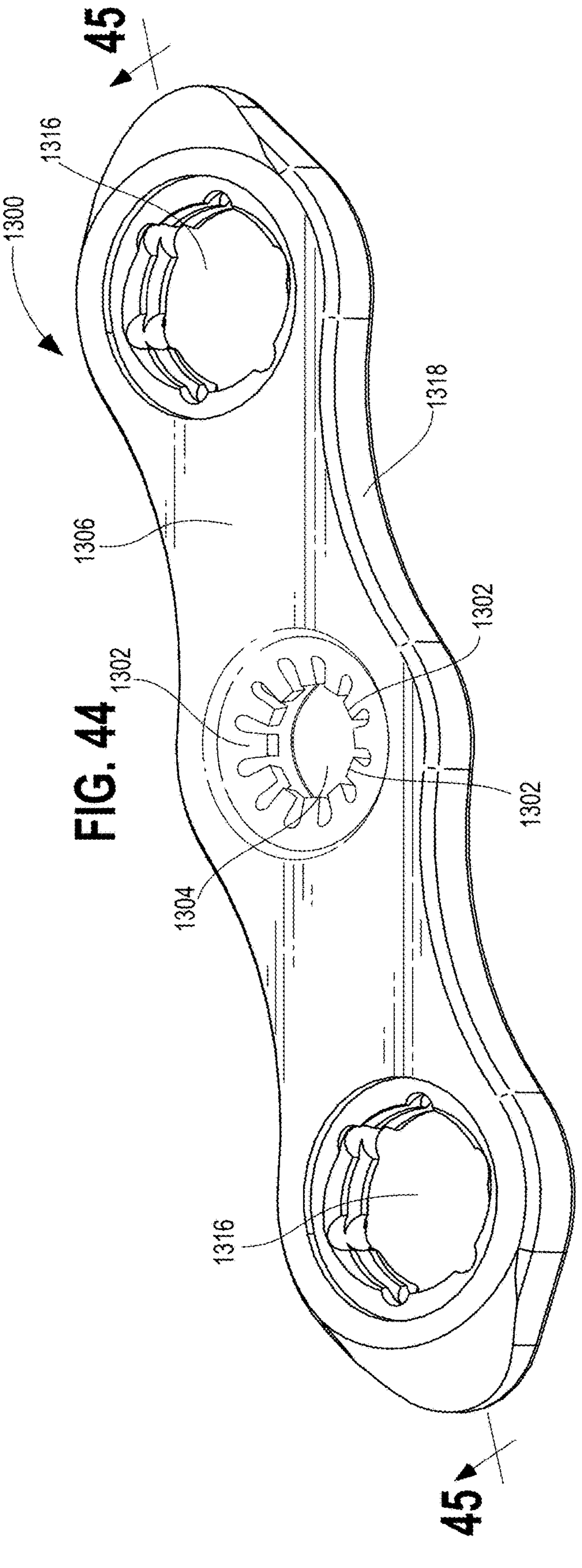
FIG. 44 is a view of a third alternative embodiment of a bone plate having an integral compression structure.
Figure 45:
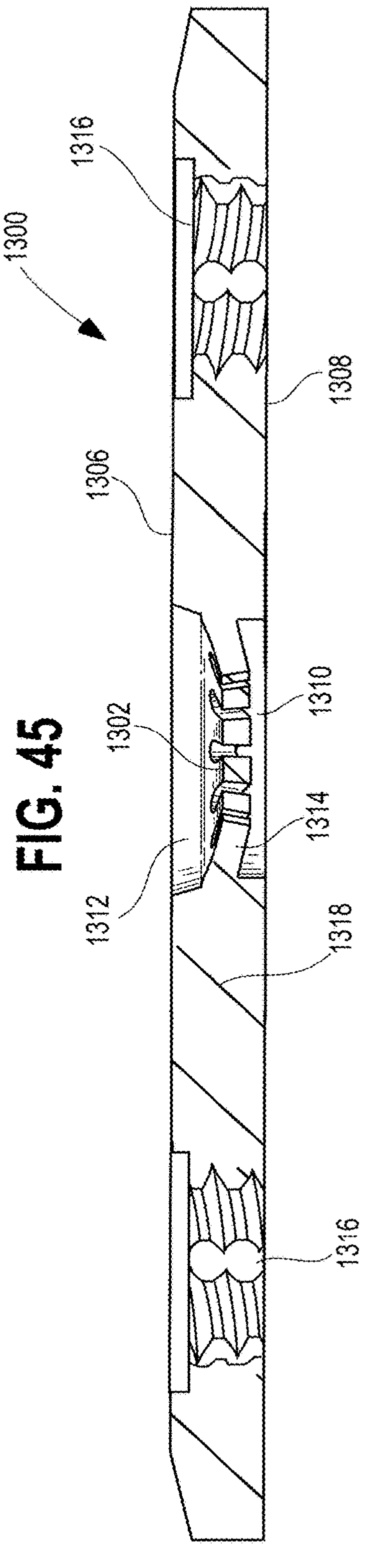
FIG. 45 is a cross-sectional view taken along line 45-45 in FIG. 44.

FIGS. 44 and FIG. 45 respectively illustrate a perspective view and a cross-sectional view (taken along line 45-45 in FIG. 44), of a third alternative embodiment of a bone plate 1300. The bone plate includes a plurality of inwardly projecting resilient teeth 1302. Like the first and second embodiments in FIGS. 40-43, the teeth are integrally formed with the plate body 1318 at points of integration around an inner peripheral surface of an aperture 1310. The teeth 1302 extend toward an axis of the aperture 1310 and extend distally, in an unbiased state, toward the lower plate surface 1308 in a generally concave structure relative to the upper plate surface 1306. An opening 1304 is formed by tips of the teeth and has a diameter configured to accommodate a shaft of a fastener. The opening 1304 also permits the head of the fastener to impinge upon and deform the teeth 1302 in a direction of travel of the screw from the upper plate surface 1306 side toward the lower plate surface 1308 side of the bone plate, upon advancement of the fastener into a bone segment. The plate 1300 further includes an upper countersunk region 1312 and a lower countersunk region 1314 formed about the aperture 1310. Fixation openings 1316 are provided to receive fixation fasteners for securing the bone plate to a surface of a bone segment.

Figure 46:
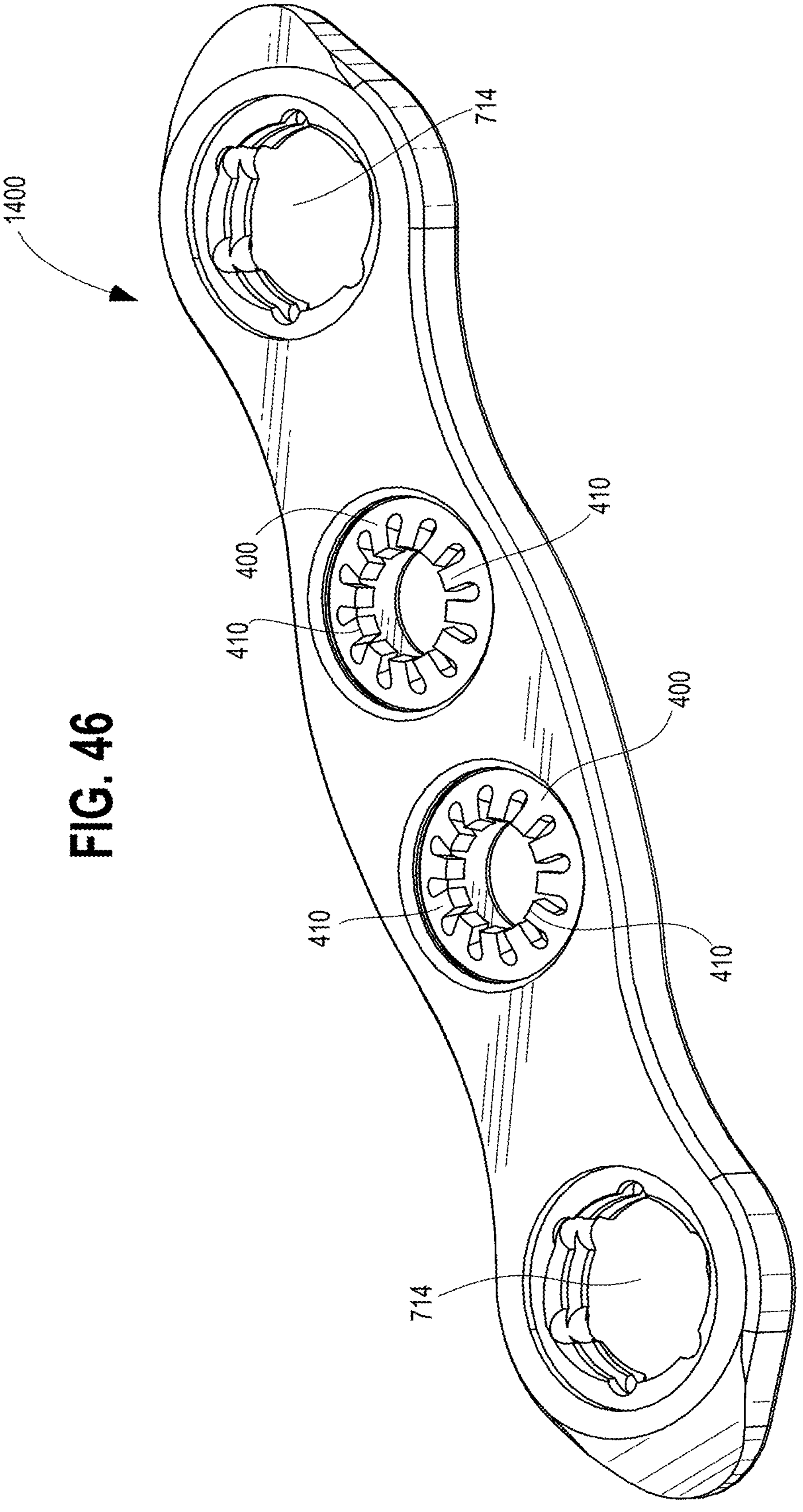
FIG. 46 is a perspective view of an alternative bone plate assembly.

FIG. 46 is a perspective view of an alternative bone plate assembly 1400 that includes two captively retained compression devices 400 and two fixation openings 714. The structures of the compression devices 400 and of the apertures, countersunk regions, intermediate seat regions, annular recessed regions of the bone plate are otherwise the same as described in connection with FIGS. 24-28. The unbiased teeth 410 of the compression devices 400 extend toward the upper plate surface 706 of the bone plate (i.e., in a convex structure relative to the upper plate surface). In other embodiments the bone plate assembly 1400, a compression device including unbiased medially extending teeth (i.e., having a flat structure) or compression device extending distally in an unbiased state (i.e., having a concave structure relative to the upper plate surface) can be used. Any combination of convex, flat, or concave structured compression devices can be combined in the bone plate assembly 1400. A bone plate assembly can generally captively retain any number of compression devices, as desired for the specific application.

Figures 47, 48, 49, 50:
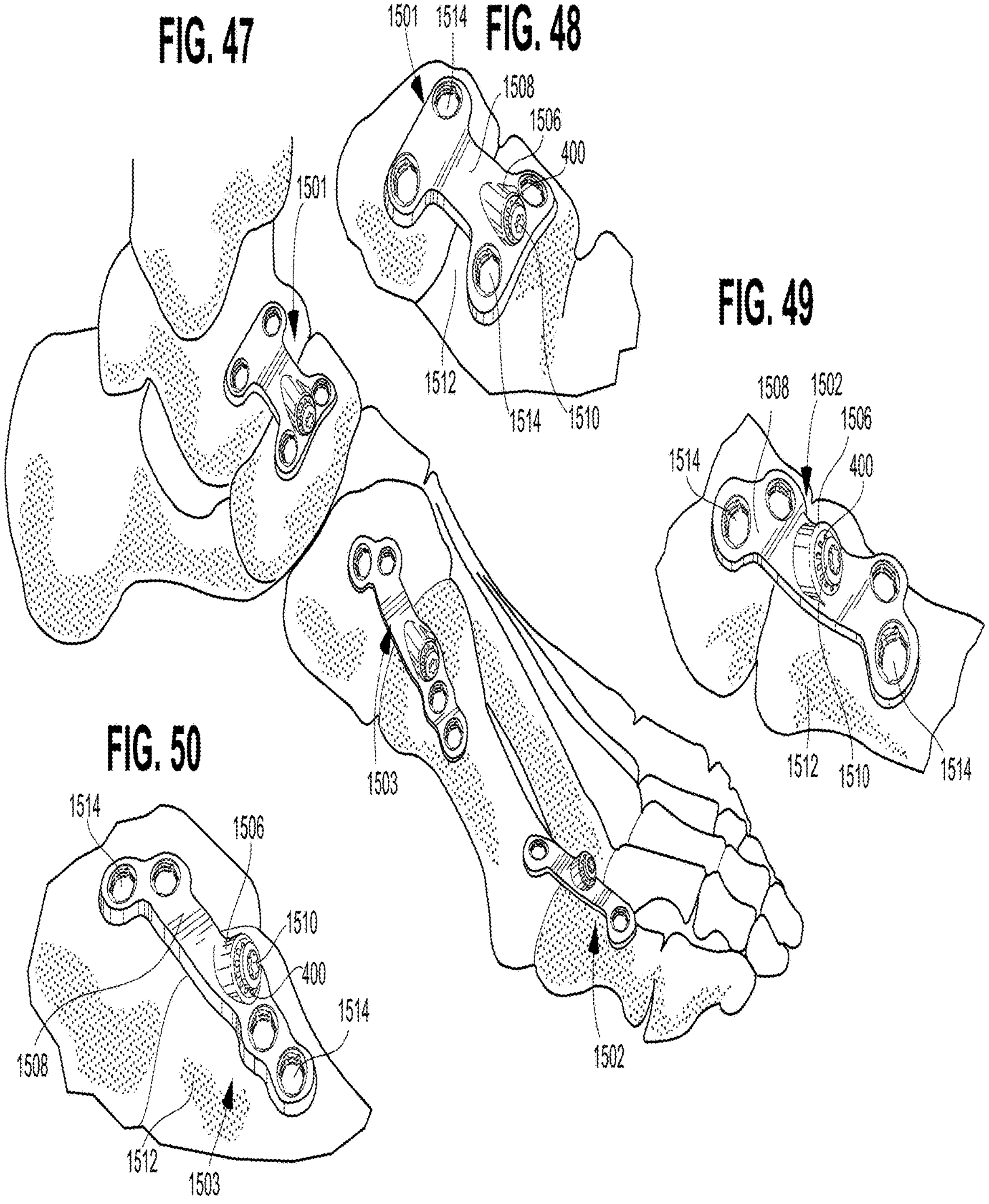
FIG. 47 is a perspective view illustrating bones of a patient's foot and first, second, and third embodiments of bone plate assemblies, each including a captively retained compression device, fixed to different positions on the foot with lag screws.
FIG. 48 is an enlarged perspective view of the first embodiment of the bone plate assembly and screw illustrated in FIG. 47.
FIG. 49 is an enlarged perspective view of the second embodiment of the bone plate assembly and screw illustrated in FIG. 47.
FIG. 50 is an enlarged perspective view of the third embodiment of the bone plate assembly and screw illustrated in FIG. 47.
Figures 51, 52:
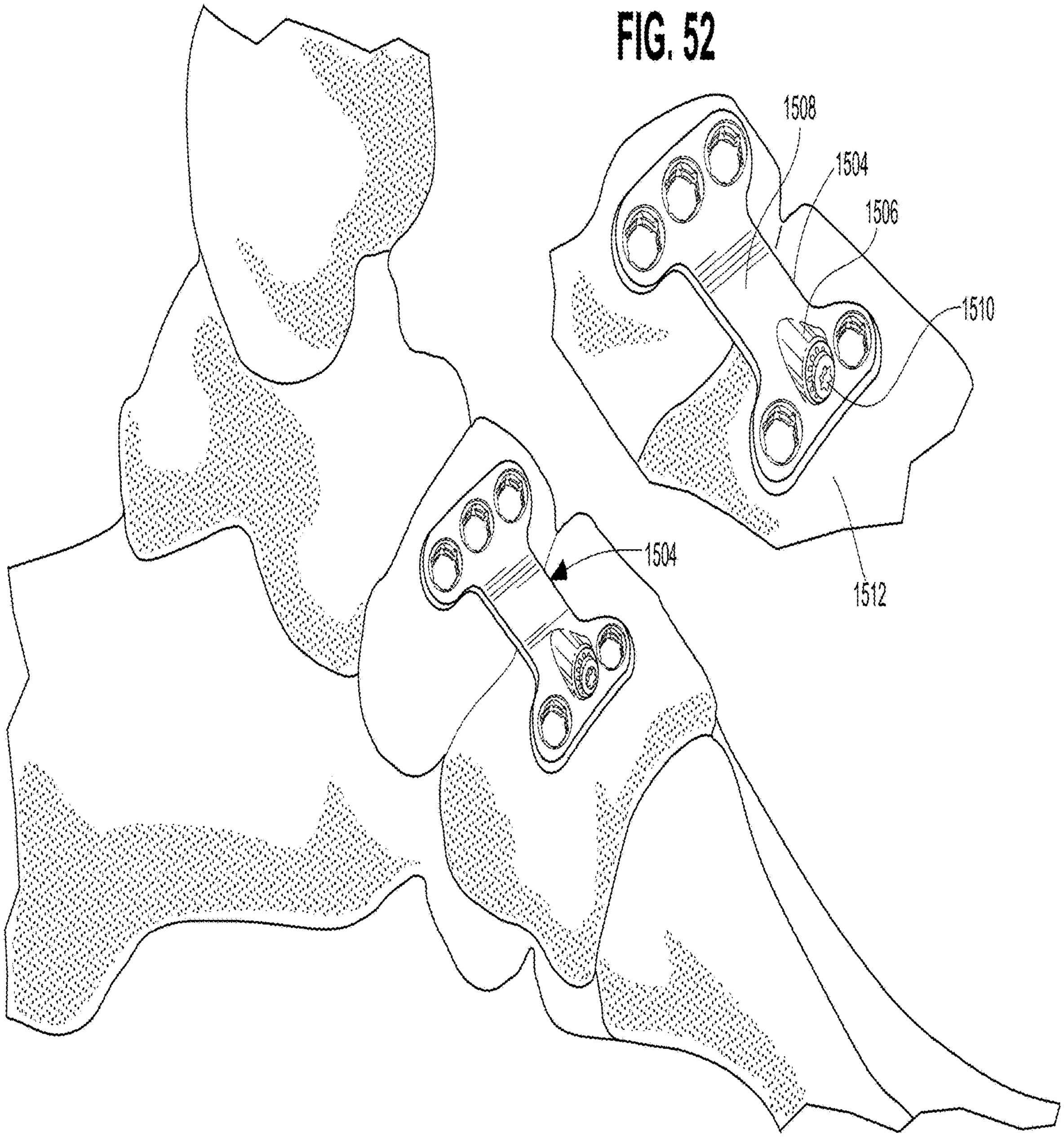
FIG. 51 is a perspective view illustrating bones of a patient's foot and a fourth embodiment of a bone plate assembly including a captively retained compression device fixed at the foot with a lag screw.
FIG. 52 is an enlarged perspective view of the fourth embodiment of the bone plate assembly and screw illustrated in FIG. 51.

FIG. 47 is a perspective view illustrating bones of a patient's foot and first, second, and third embodiments of bone plate assemblies, each including captively retained compression devices. FIG. 48-50 are enlarged perspective views, respectively, of the first embodiment of the bone plate assembly 1501 utilized in a Talonavicular fusion (TN Fusion), the second embodiment of the bone plate assembly 1502 utilized in a Metatarsal-phalangeal joint fusion (MTP Fusion), and the third embodiment of the bone plate assembly 1503 utilized in a "Lapidus" fusion (also referred to as 1st tarsometatarsal joint arthrodesis). FIGS. 51 and 52 are perspectives view illustrating bones of a patient's foot and a fourth embodiment of a bone plate assembly 1504 utilized in a Naciculocuneiform joint fusion (NC Fusion). Each of the bone plate assemblies 1501, 1502, 1503, 1504 include an off-angle structure 1506 formed in the bone plates 1508. The off-angle structures 1506 permit lag screws to pass through the bone plate at non-perpendicular angles. Compression devices 400 are captively retained within the off-angle structures 1506 so that lag screws pass through the openings of the compression devices, through the apertures of the bone plates 1508, and into bone segments 1512. Head portions 1510 of the screws deform the teeth of the compression devices toward the bone segments. In turn, the compression devices exert a biasing force against the head portions 1510 of the screws to maintain compression at a point of fracture in the bone segments. The bone plates 1508 also include fixation openings 1514 configured to receive fixation fasteners for securing the bone plates to bone.

Figures 53, 54, 55, 56:
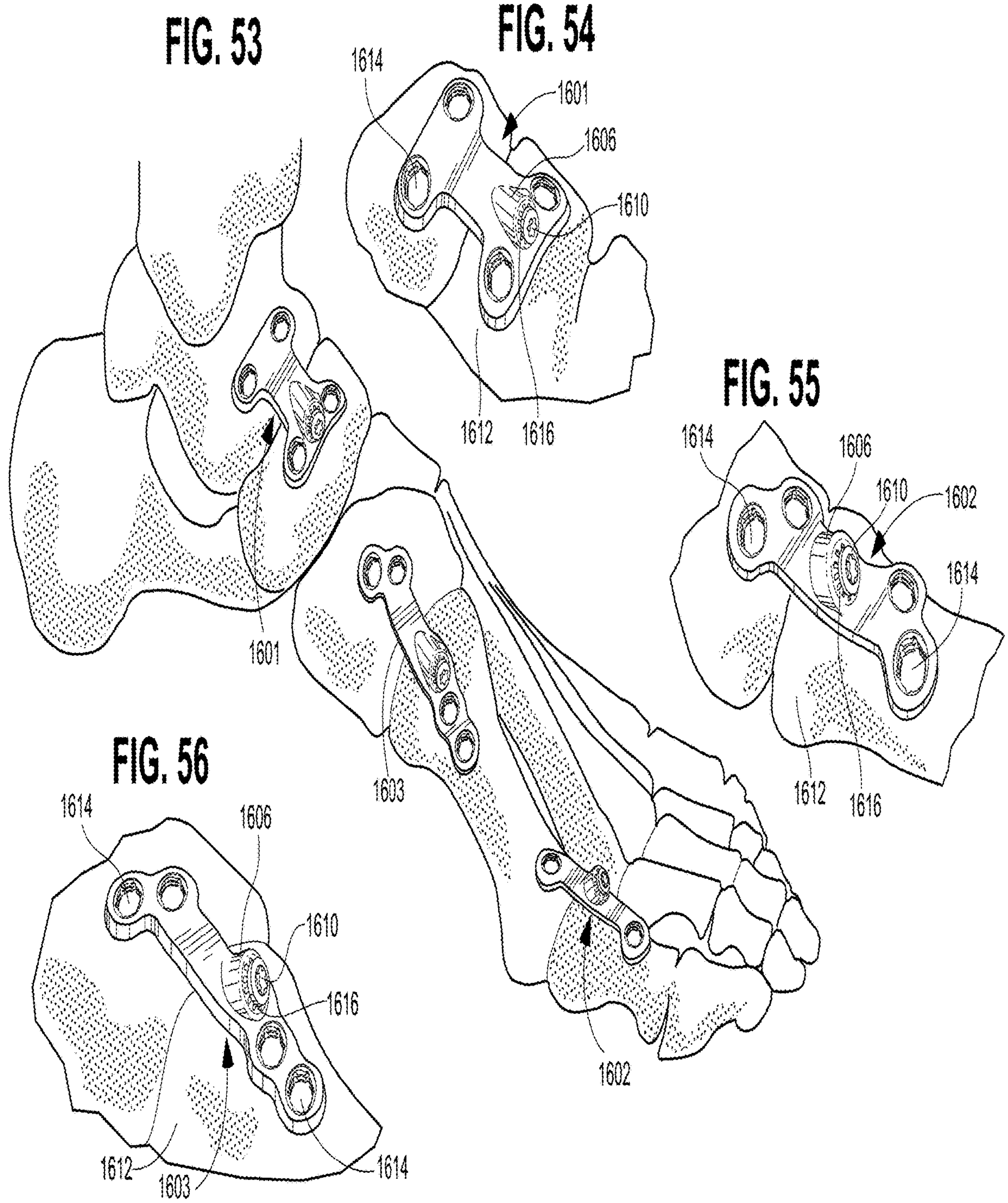
FIG. 53 is a perspective view illustrating bones of a patient's foot and first, second, and third embodiments of bone plates, each including integral compression structures, fixed at different positions on the foot with lag screws.
FIG. 54 is an enlarged perspective view of the first embodiment of the bone plate assembly and screw illustrated in FIG. 53.
FIG. 55 is an enlarged perspective view of the second embodiment of the bone plate assembly and screw illustrated in FIG. 53.
FIG. 56 is an enlarged perspective view of the third embodiment of the bone plate assembly and screw illustrated in FIG. 53.

FIG. 53 is a perspective view illustrating bones of a patient's foot and first, second, and third embodiments of bone plates. Each of the bone plates include integrally formed teeth. FIG. 54-56 are enlarged perspective views, respectively, of the first embodiment of the bone plate 1601 utilized in a TN Fusion, the second embodiment of the bone plate 1602 utilized in a MTP Fusion, and the third embodiment of the bone plate 1603 utilized in a Lapidus fusion. Each of the bone plates 1601, 1602, and 1603 include an off-angle structure 1606. The off-angle structures 1506 permit lag screws to pass through the bone plates at non-perpendicular angles. Integrally formed teeth 1616 are formed in the off-angle structures 1606 so that lag screws pass through the openings formed by the teeth. The screw also passes through apertures of the bone plates 1601, 1602, and 1603 and then into the bone segments 1612. Head portions 1610 of the screws deform the integrally formed teeth toward the bone segments. In turn, the integrally formed teeth exert a biasing force against the head portions 1610 of the screws to maintain compression at a point of fracture in the bone segments. The bone plates 1601, 1602, and 1603 also include fixation openings 1614 configured to receive fixation fasteners for securing the bone plates to bone.

Figures 57, 58, 59, 60:
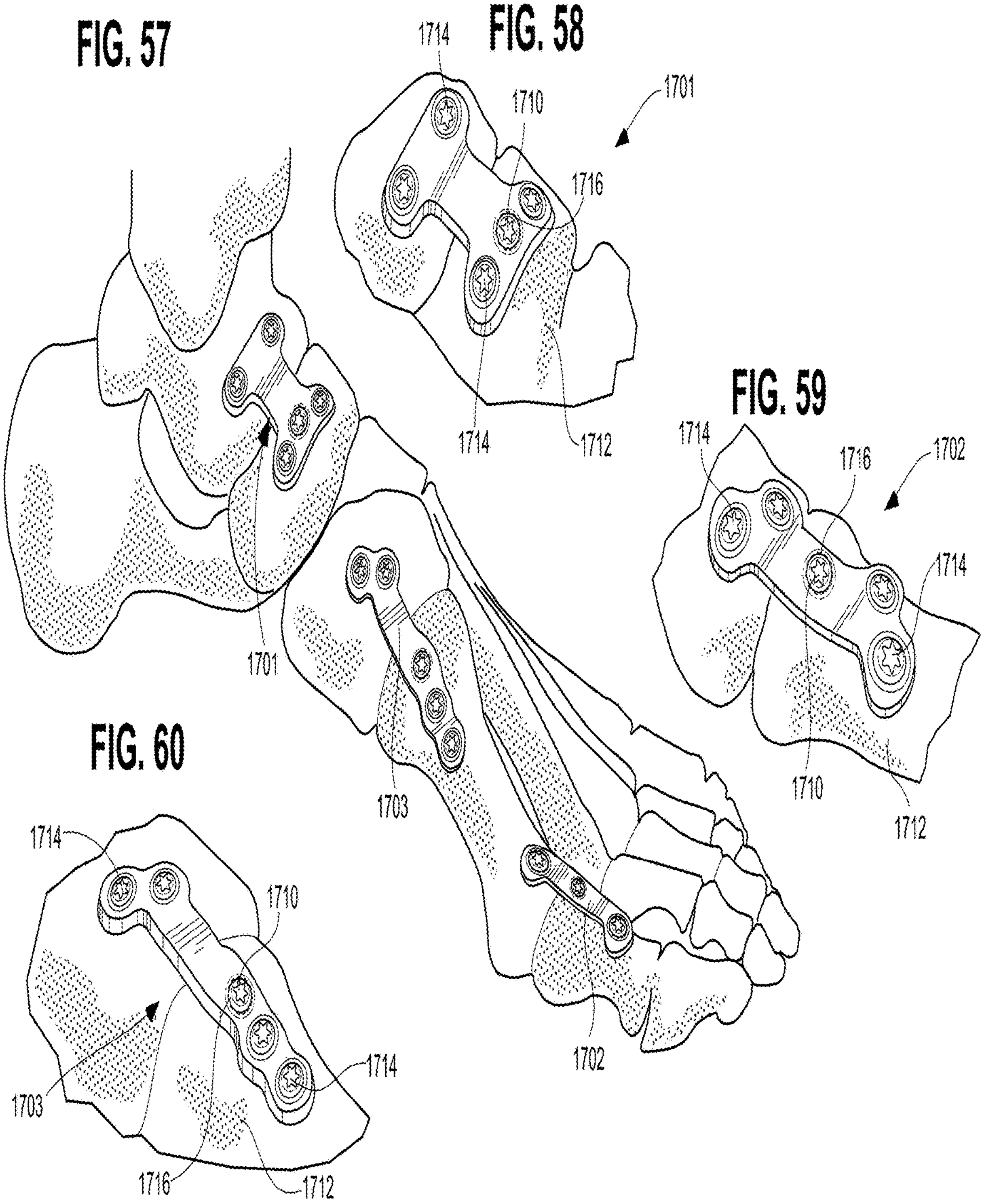
FIG. 57 is a perspective view illustrating bones of a patient's foot and first, second, and third embodiments of bone plates, each including integral compression structures, fixed at different positions on the foot with fixation screws and lag screws.
FIG. 58 is an enlarged perspective view of the first embodiment of the bone plate assembly and screws illustrated in FIG. 57.
FIG. 59 is an enlarged perspective view of the second embodiment of the bone plate assembly and screws illustrated in FIG. 57.
FIG. 60 is an enlarged perspective view of the third embodiment of the bone plate assembly and screws illustrated in FIG. 57, and FIGS. 61-63, 65-67, 69-71, 73-75, 77-79, and 81-83 show graphs of axial displacement between test jigs over test periods and axial force exerted between the test jigs and test specimens during the same periods.

FIG. 57 is a first perspective view illustrating bones of a patient's foot and first, second, and third embodiments of a bone plates. The bone plates each include integrally formed teeth. FIG. 58-60 are enlarged perspective views, respectively, of the first embodiment of the bone plate 1701 utilized in a TN Fusion, the second embodiment of the bone plate 1702 utilized in a MTP Fusion, and the third embodiment of the bone plate 1703 utilized in a Lapidus fusion. Each of the bone plates 1701, 1702, and 1703 include integrally formed teeth 1716 permitting lag screws to pass through the openings formed by the teeth. The screw also passes through apertures of the bone plates 1701, 1702, and 1703 and then into the bone segments 1712. Head portions 1710 of the lag screws deform the integrally formed teeth toward the bone segments. In turn, the integrally formed teeth exert a biasing force against the head portions 1710 of the screws to maintain compression at a point of fracture in the bone segments. The bone plates 1701, 1702, and 1703 also include fixation screws passing through fixation openings for securing the bone plates to bone. Head portions 1714 of the fixation screws are illustrated in FIGS. 57-60.

EXAMPLES

Example 1

Separate test examples 1.1, 1.2, and 1.3 were prepared, each including two 40 PCF foam blocks, a bone screw having a 4.0 mm thread diameter (major outer diameter), and a compression device (as shown in FIG. 19). Each compression device was formed of nitinol alloy and had a thickness of 0.7 mm, an internal diameter (central opening) of 3.37 mm, and an outer diameter of 7.65 mm.

For each of test examples 1.1, 1.2, and 1.3, the screw, the blocks, and the compression device were assembled as follows. A first of the two foam blocks included a countersink, and the compression device was disposed over the countersink such that the compression device extended in a domed configuration above the surface of the first foam block. The threaded portion of the screw was then advanced through the center opening of the compression device and through the first and second blocks. Spacing was maintained between the two blocks after insertion of the screw.

A testing apparatus including a load cell and an opposing crosshead was provided. During each test, the first block of a test example was secured in a test jig attached to the crosshead and the second block was secured in a test jig attached to the load cell such that the screw was spanned the spacing between the two blocks attached to the test jigs. The threaded portion of the screw was fully seated in the second foam block and the smooth shank of the screw exposed between the blocks to allow loading and unloading of forces between the test jigs. Output from the testing apparatus was recorded by a computer.

Figure 61:
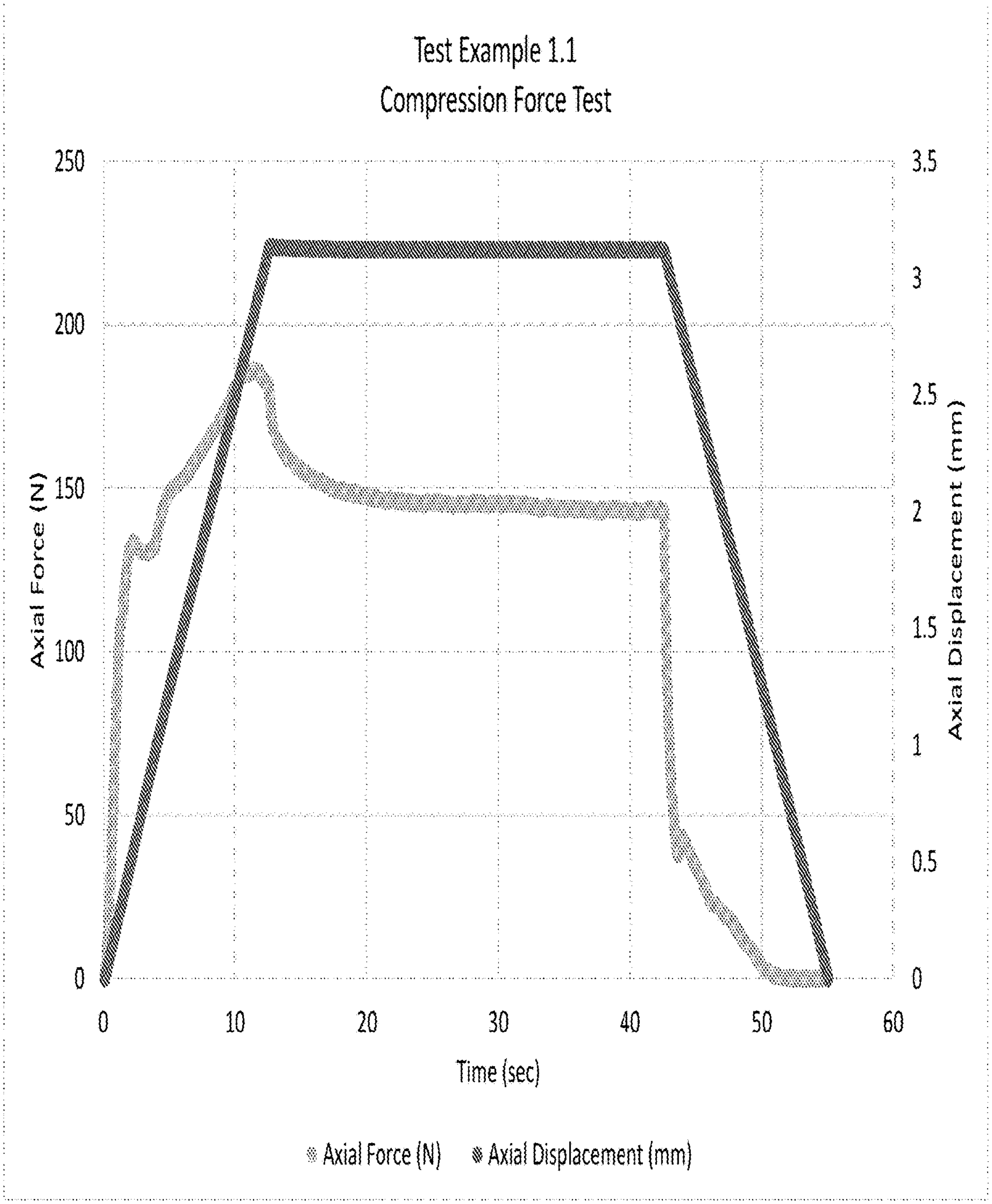
Figure 62:
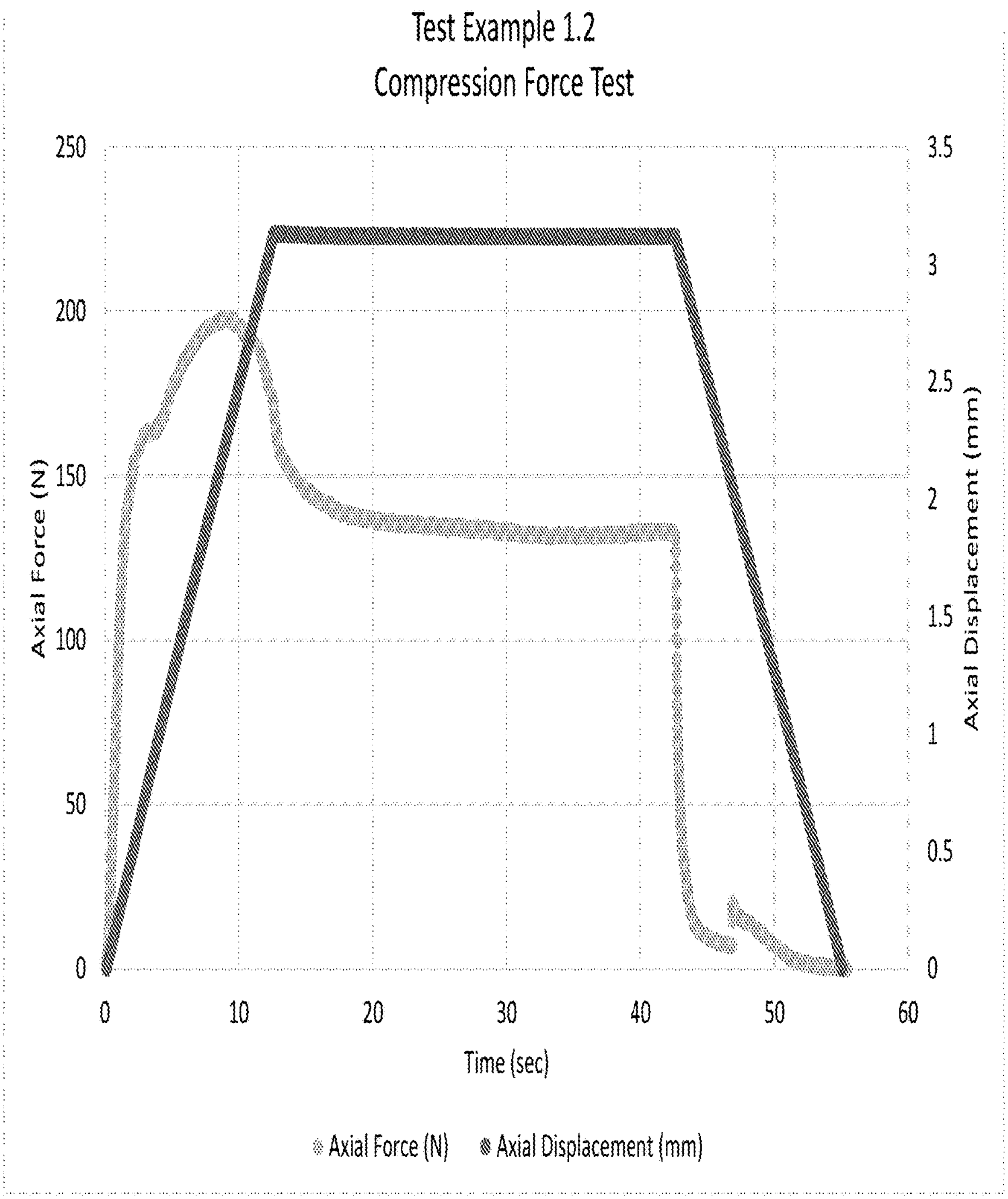
Figure 63:
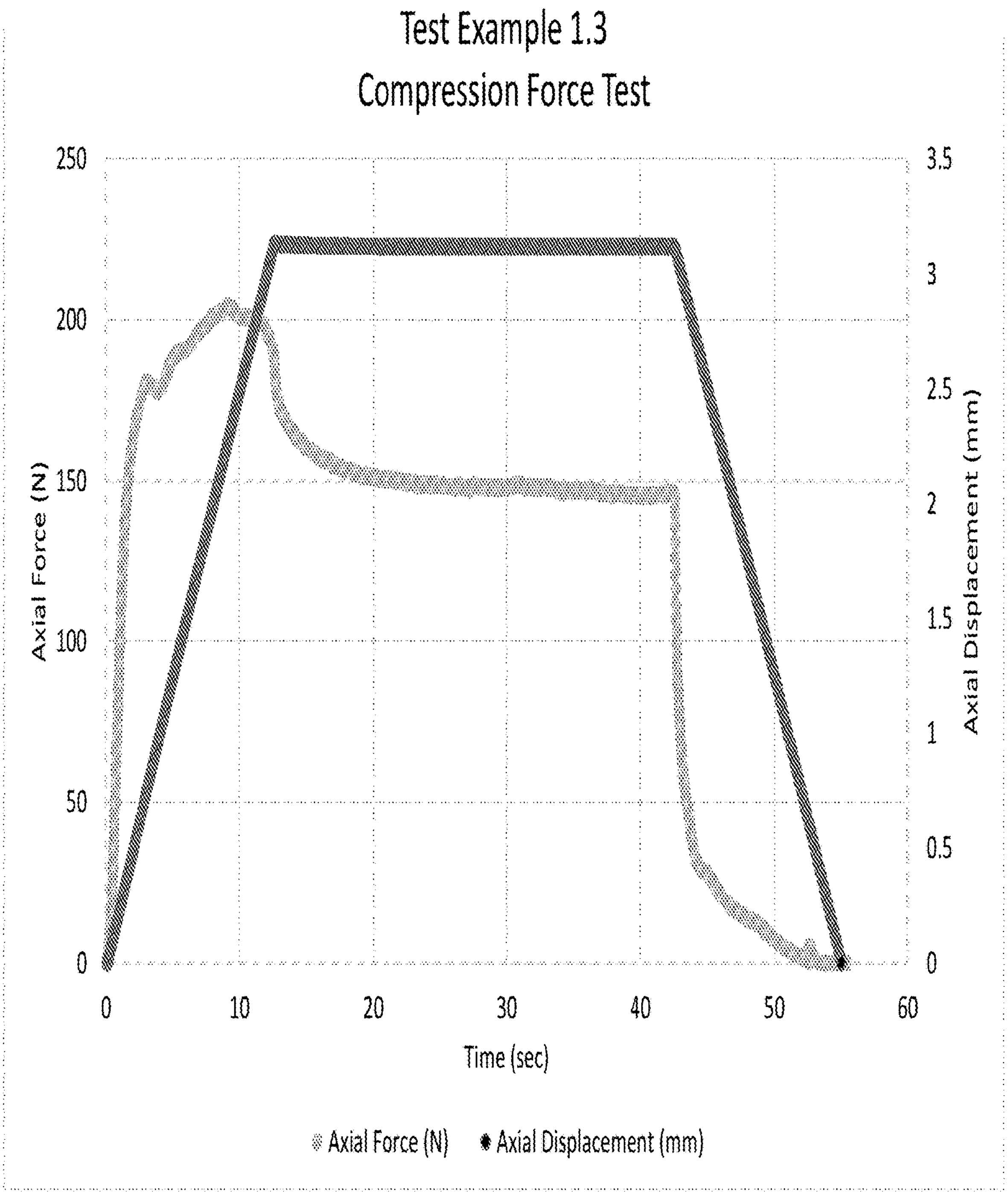

The graphs in FIGS. 61-63 show, for test examples 1.1, 1.2, and 1.3 respectfully, axial displacement between the test jigs over the test period and axial force exerted between the test jigs and the compression device during the same period. Starting at time 0 and an axial displacement 0, the testing apparatus drew the test jigs (and foam blocks) apart at a constant rate of displacement. This displacement resulted in the head of the screw progressively compressing the teeth of the compression device into the countersink of the first foam block. The testing apparatus stopped axial displacement of the test jigs at a maximum applied displacement where the head of the screw was below flush with the surface of the first block, such that the teeth of the compression device were inverted within the countersink of the first foam block. The testing apparatus held the test jigs at this maximum applied displacement for 30 seconds, as depicted in the horizontal portion of the axial displacement plot, and then initiated an unloading process by advancing the test jigs back together, again at the same constant rate of displacement at which the test jigs were initially drawn apart. The axial force plots in FIGS. 61-63 show that the compression devices of test examples 1.1, 1.2, and 1.3 continued to exert axial compressive force to the foam blocks as the testing apparatus moved the test jigs (and the two foam blocks) back together during the unloading process.

Table 1 shows, for test examples 1.1, 1.2, and 1.3, the maximum applied displacement (maximum separation) between the test jigs during the test, the peak force applied between the test jigs and the compression device during testing, and the force applied between the test jigs and the compression device after maintaining maximum applied displacement for 30 seconds.

TABLE 1

| Test Example | Maximum applied displacement (mm) | Peak force applied (N) | Force applied after 30 Secs (N) |
|---|---|---|---|
| 1.1 | 3.13 | 186 | 143 |
| 1.2 | | 198 | 132 |
| 1.3 | | 204 | 146 |
| Avg. | — | 196 | 141 |
| Std. Dev. | — | 9 | 7 |

Figure 64:
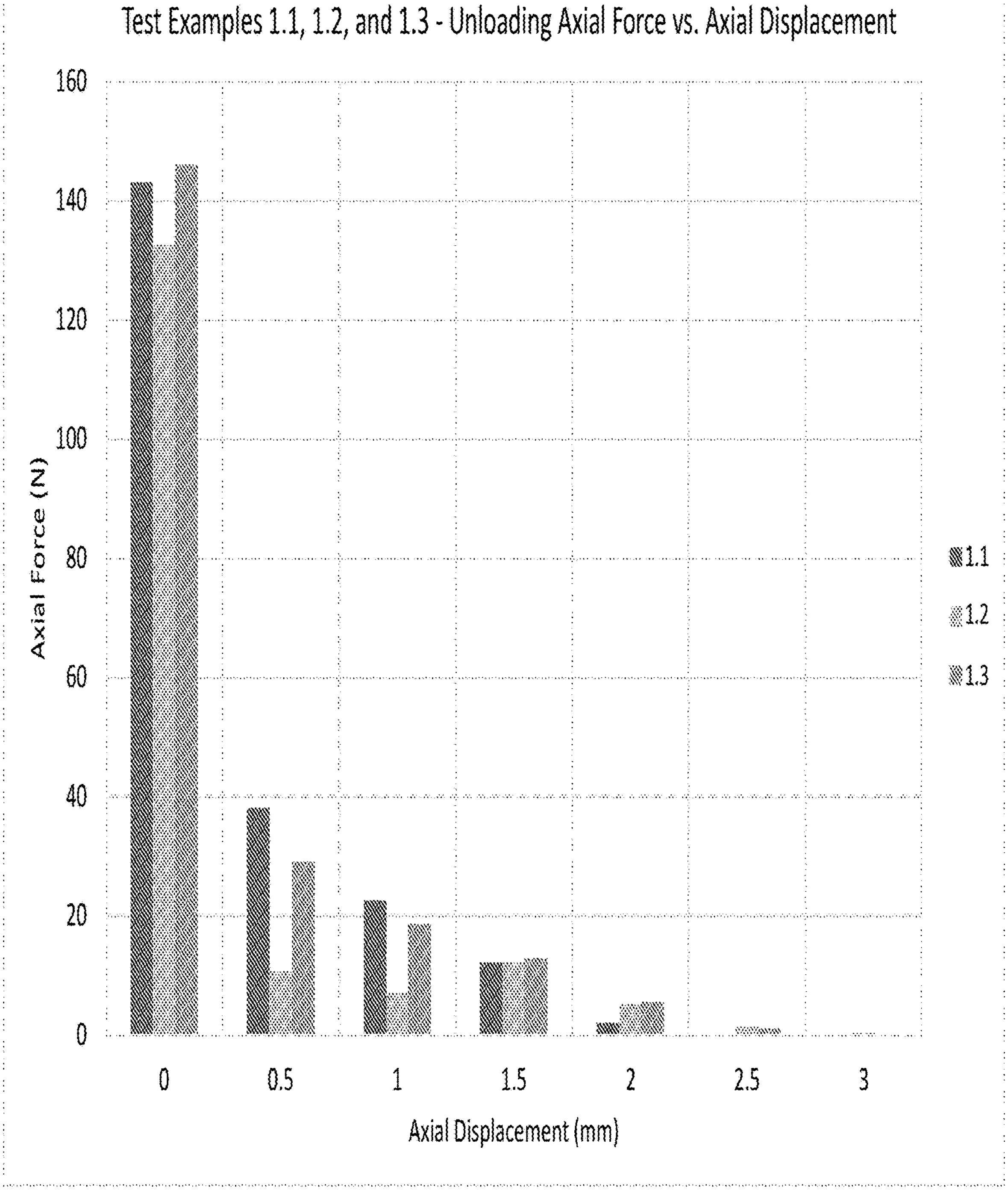
FIGS. 64, 68, 72, 76, 80 and 84 show charts of axial force exerted between test jigs and test specimens just before and during an unloading process.

FIG. 64 includes a bar chart showing the axial force exerted between the test jigs and the compression device of test examples 1.1, 1.2, and 1.3, just before and during the unloading process. The axial forces applied at an axial displacement of 0 mm represent the force applied between the compression device and test jigs at maximum applied displacement, i.e., just before the unloading process. The axial forces at axial displacements 0.5 mm, 1 mm, 1.5 mm, 2 mm, and 2.5 mm represent the axial forces applied between the compression device and test jigs as the testing apparatus decreased the distance between the foam blocks by these displacements. FIG. 64 shows that the compression devices of test examples 1.1, 1.2, and 1.3 continued to exert axial compressive force as the testing apparatus advanced the foam blocks together.

Example 2

Test examples 2.1, 2.2, and 2.3 were tested in the same manner as in Example 1, except that testing was conducted using bone screws having 4.5 mm thread diameters and compression devices having thicknesses of 0.8 mm, internal diameters of 4.25 mm, and outer diameters of 8.5 mm.

Figure 65:
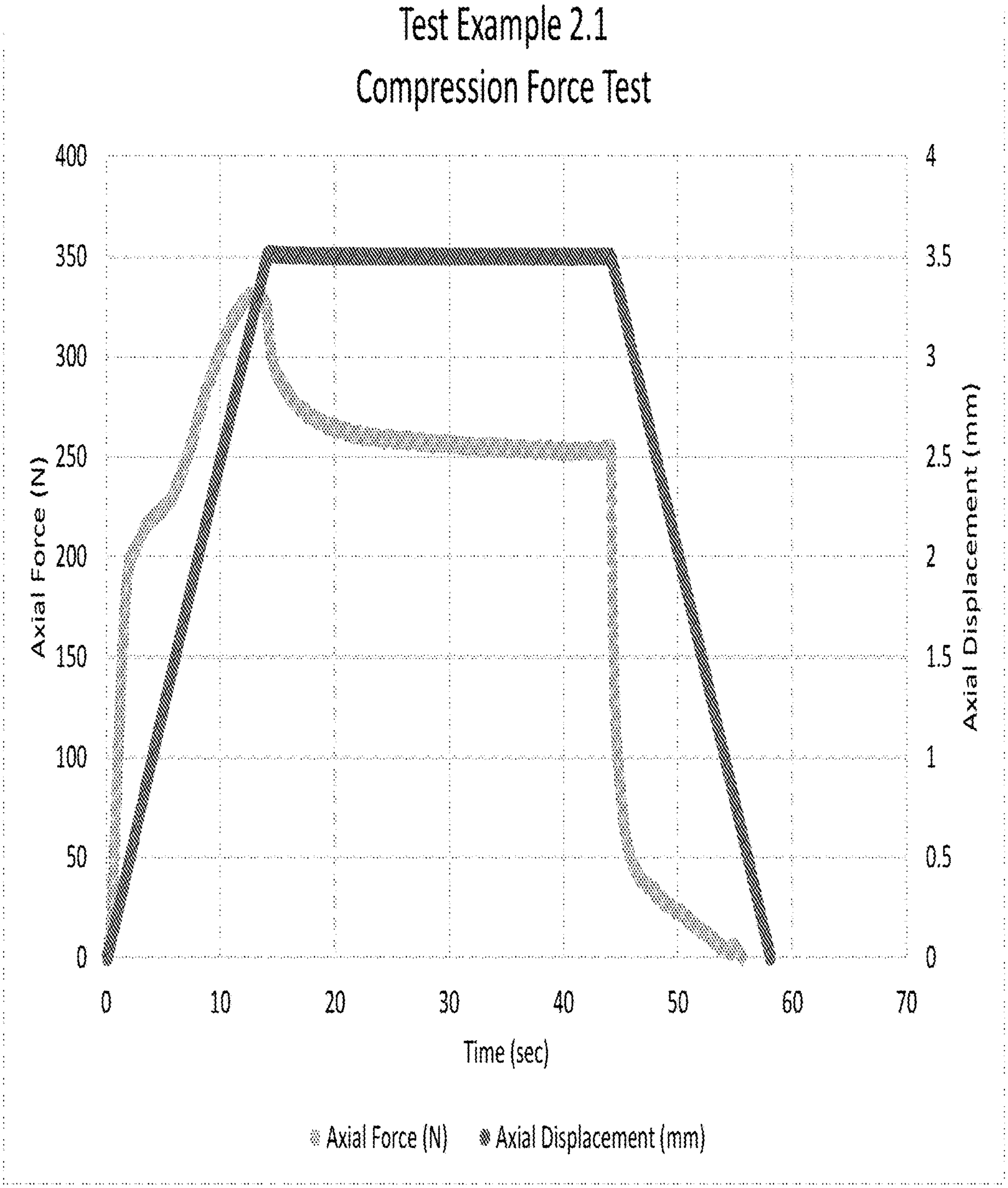
Figure 66:
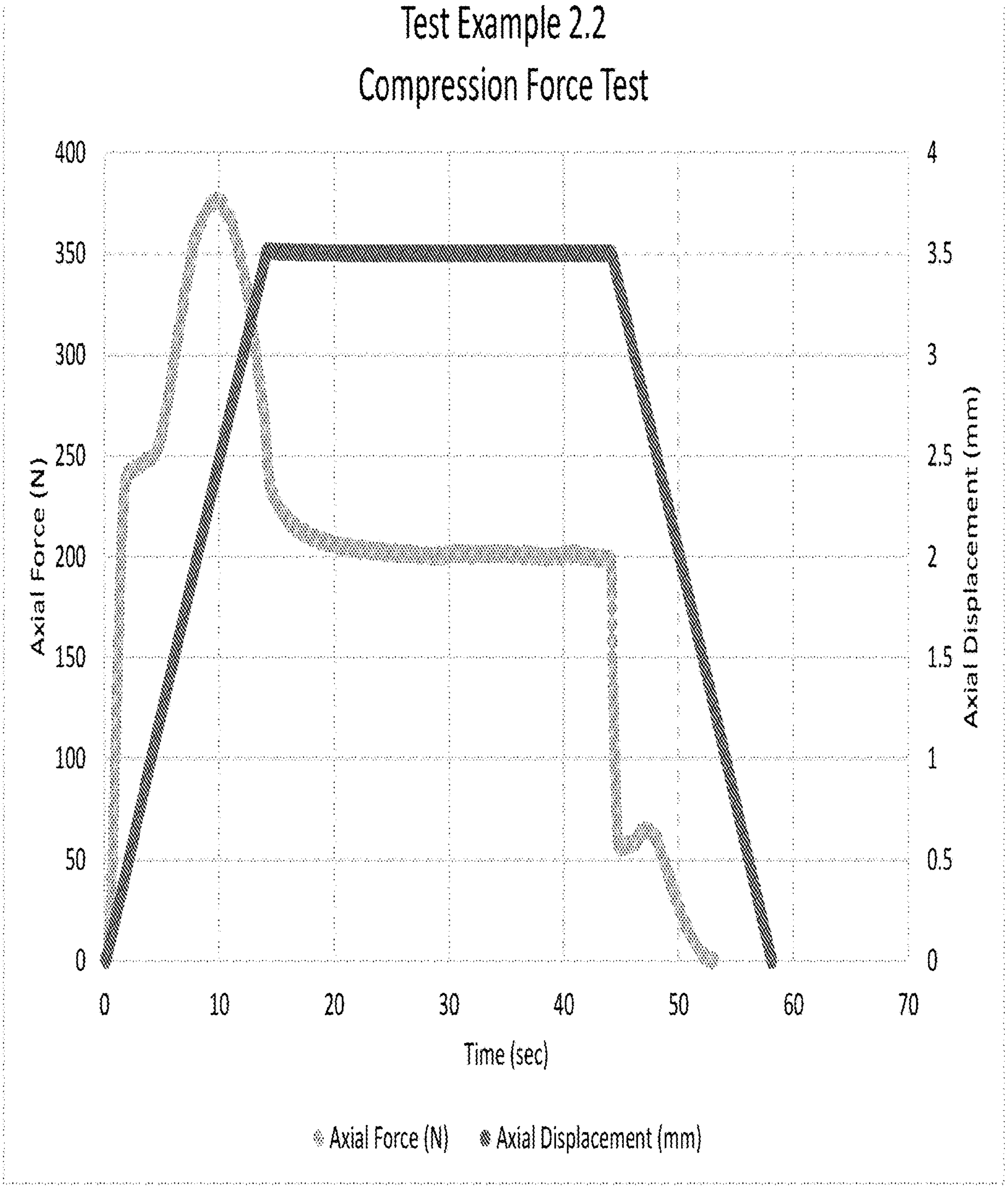
Figure 67:
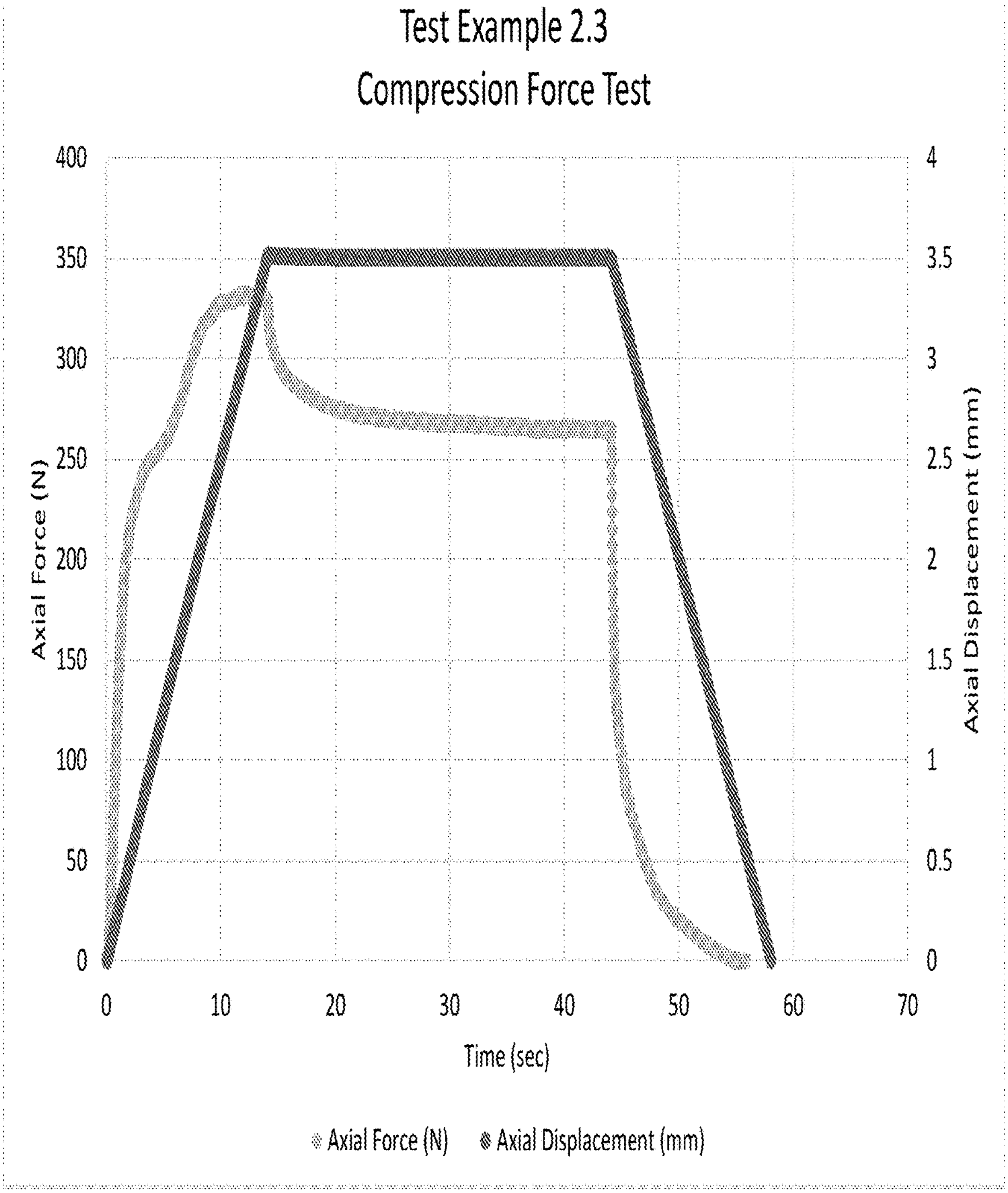
Figure 68:
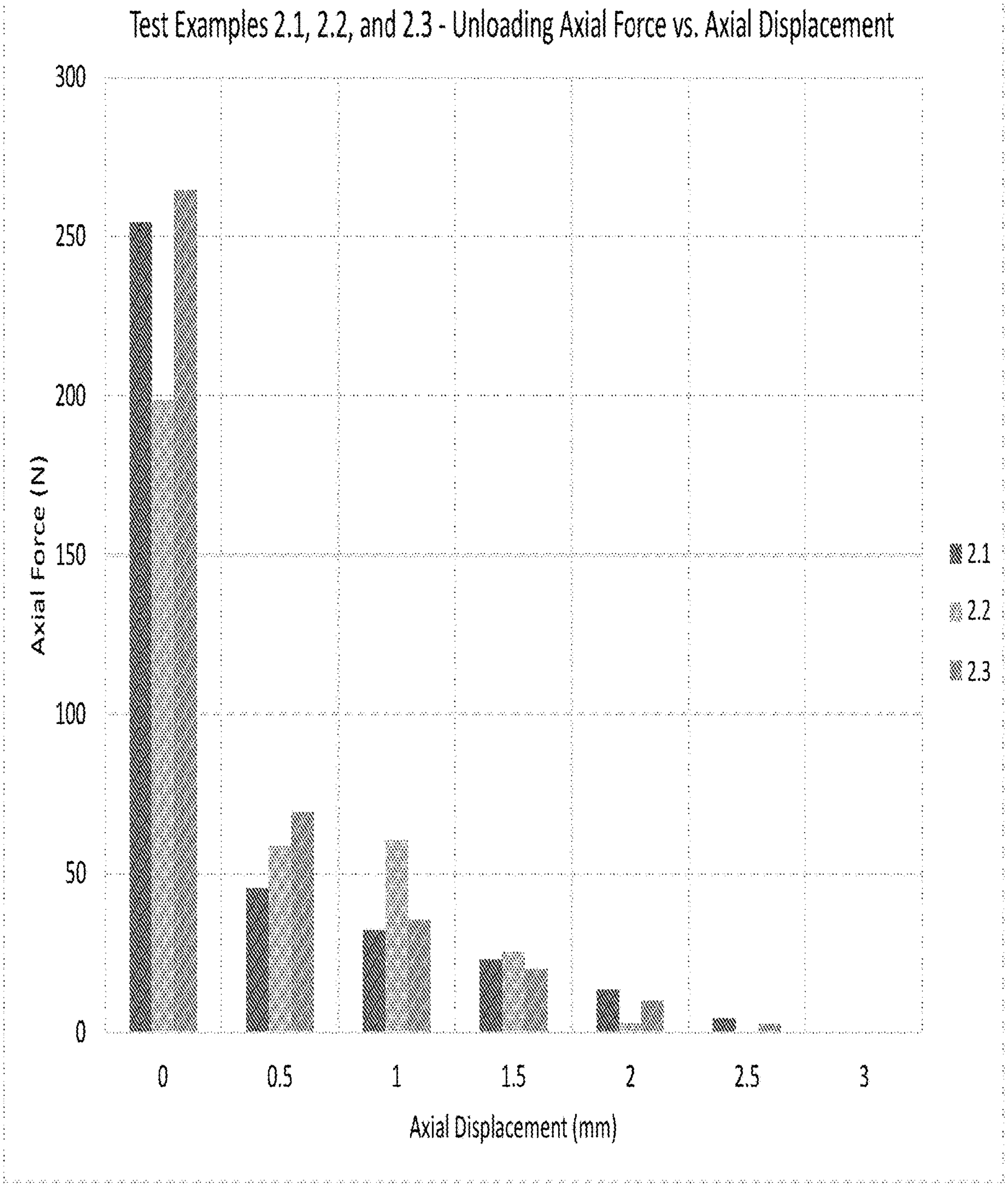

The graphs of FIGS. 65-67 show, for test examples 2.1, 2.2, and 2.3 respectfully, axial displacement between the test jigs over the test period and axial force exerted between the test jigs and the compression device of over the same period. FIG. 68 shows a bar chart of axial force applied between the compression device and test jigs of test examples 2.1, 2.2, and 2.3, before and during the unloading process. These figures show that the compression devices of test examples 2.1, 2.2, and 2.3 continued to exert axial compressive force as the testing apparatus advanced the foam blocks back together.

For test examples 2.1, 2.2, and 2.3, Table 2 shows the maximum applied displacement, the peak force applied between the test jigs and the compression device, and the force applied between the test jigs and the compression device after maintaining maximum applied displacement for 30 seconds.

TABLE 2

| Test Example | Maximum applied displacement (mm) | Peak force applied (N) | Force applied after 30 Secs (N) |
|---|---|---|---|
| 2.1 | 3.50 | 332 | 254 |
| 2.2 | | 376 | 199 |
| 2.3 | | 333 | 264 |
| Avg. | — | 347 | 239 |
| Std. Dev. | — | 25 | 35 |

Example 3

Test examples 3.1, 3.2, and 3.3 were tested in the same manner as in Example 1, except that testing was conducted using bone screws having 5.5 mm thread diameters and compression devices having thicknesses of 0.9 mm, internal diameters of 5.15 mm, and outer diameters of 10.2 mm.

Figure 69:
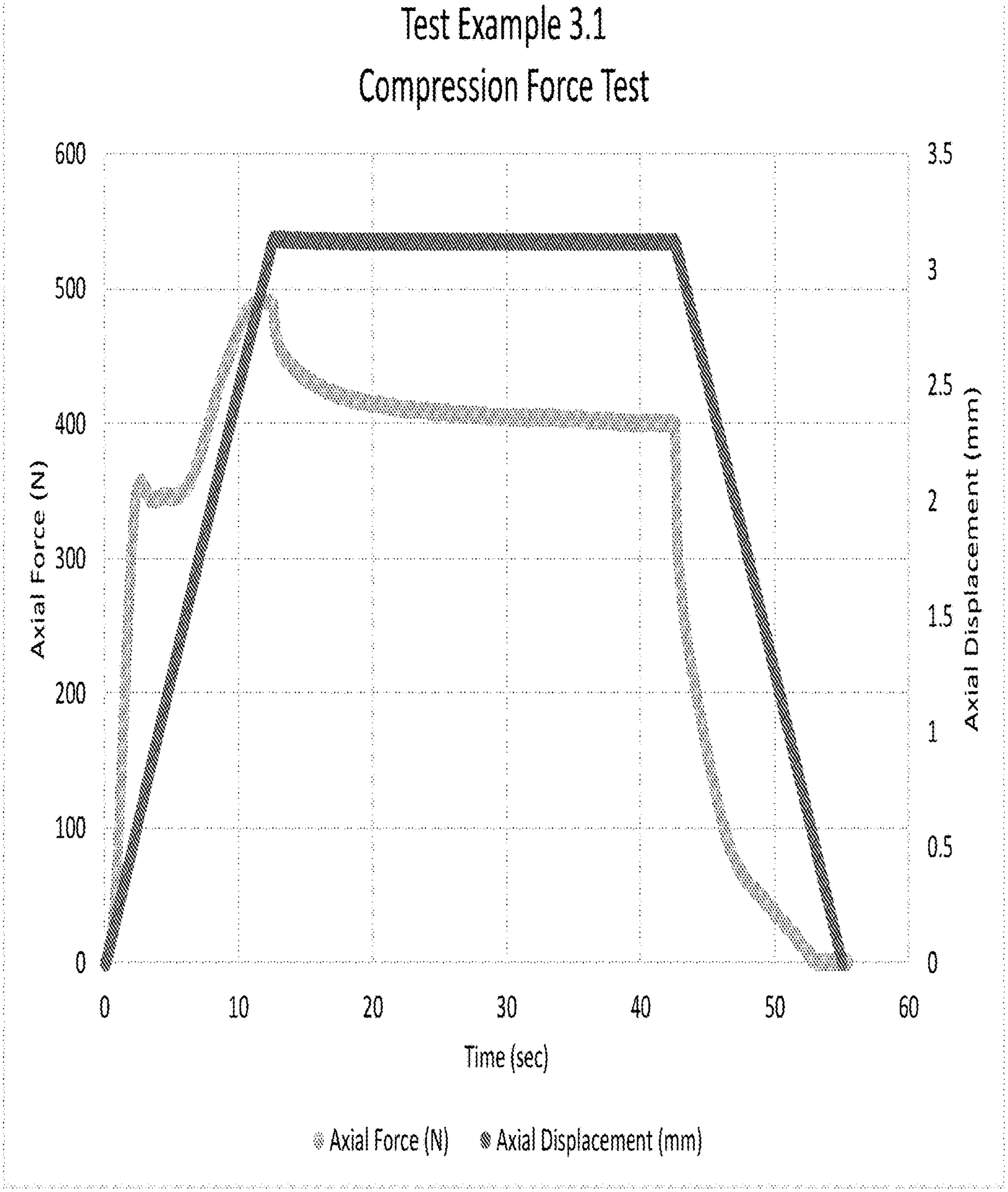
Figure 70:
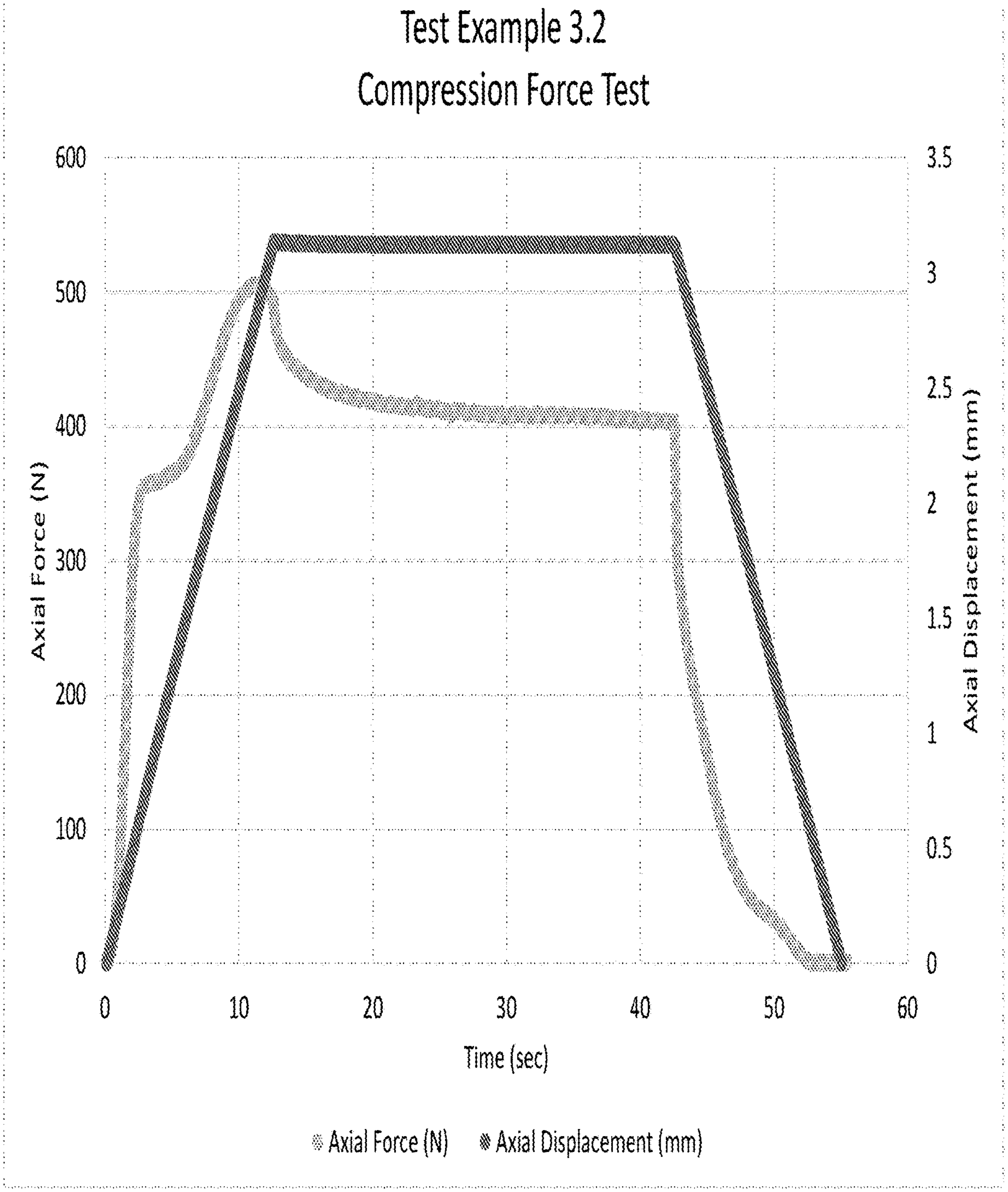
Figure 71:
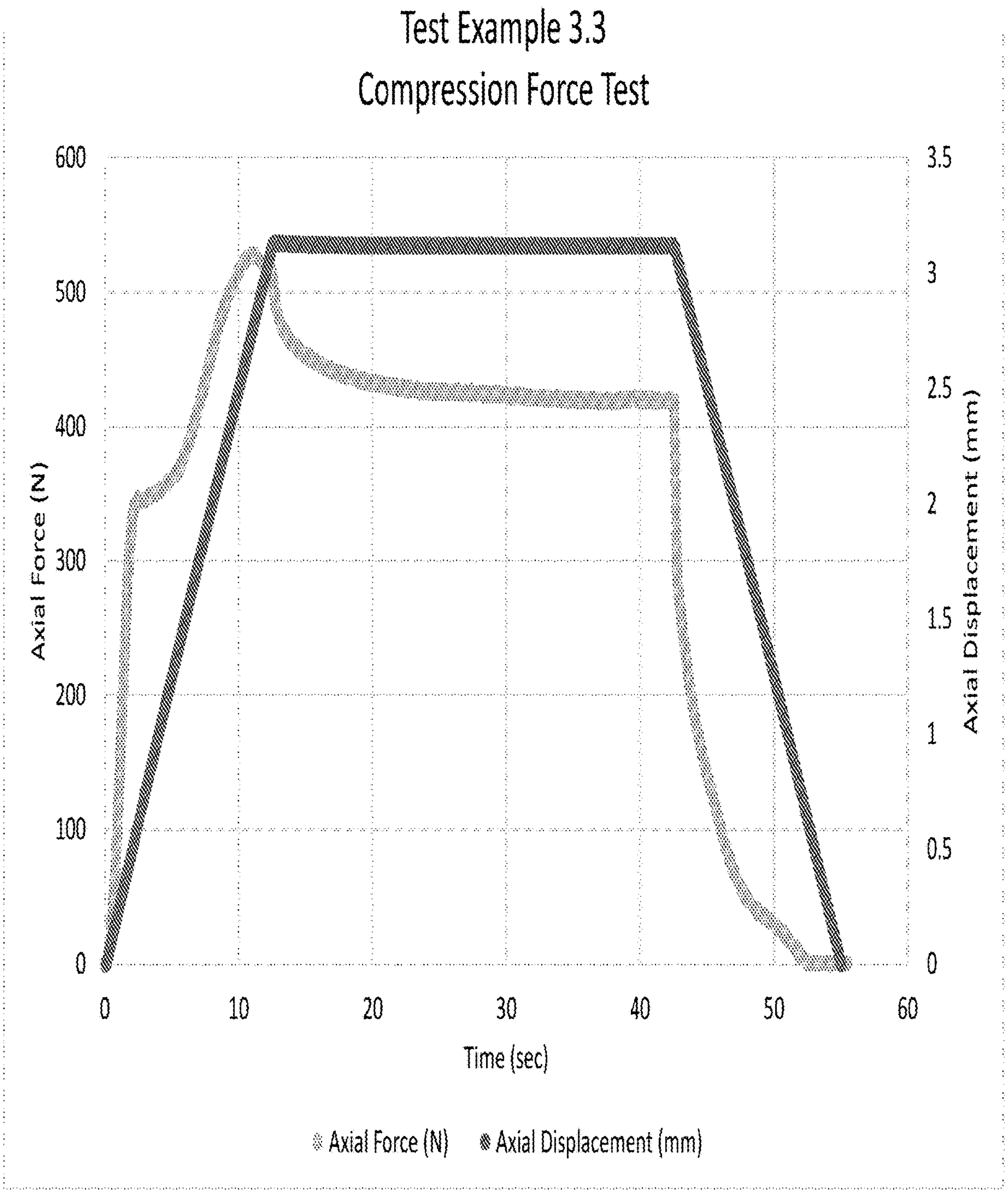
Figure 72:
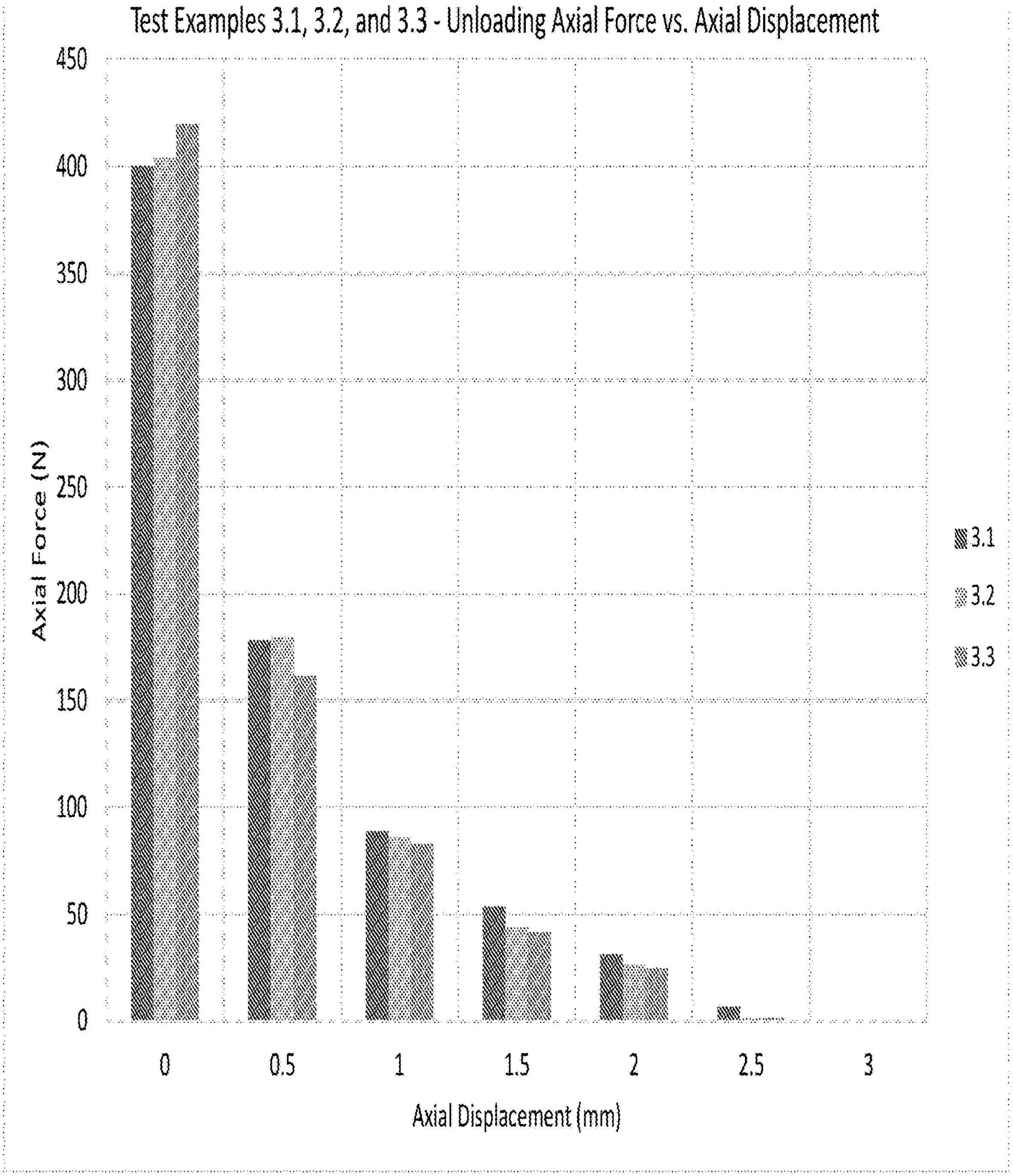

For test examples 3.1, 3.2, and 3.3, the graphs of FIGS. 69-71 respectfully show axial displacement between the test jigs over the test period and axial force exerted between the test jigs and the compression device over the same period. FIG. 72 shows a bar chart of axial force applied between the compression device and test jigs of test examples 3.1, 3.2, and 3.3, before and during the unloading process. These figures show that the compression devices of test examples 3.1, 3.2, and 3.3 continued to exert axial compressive force as the testing apparatus advanced the foam blocks back together.

Table 3 shows, for test examples 3.1, 3.2, and 3.3, the maximum applied displacement, the peak force applied between the test jigs and the compression device, and the force applied between the test jigs and the compression device after maintaining maximum applied displacement for 30 seconds.

TABLE 3

| Test Example | Maximum applied displacement (mm) | Peak force applied (N) | Force applied after 30 Secs (N) |
|---|---|---|---|
| 3.1 | 3.12 | 491 | 400 |
| 3.2 | | 506 | 404 |
| 3.3 | | 528 | 420 |
| Avg. | — | 509 | 408 |
| Std. Dev. | — | 19 | 10 |

Example 4

Test examples 4.1, 4.2, and 4.3 were tested in the same manner as in Example 1, except that testing was conducted using bone screws having 7.0 mm thread diameters and compression devices having thicknesses of 1 mm, internal diameters of 6.47 mm, and outer diameters of 12.75 mm.

Figure 73:
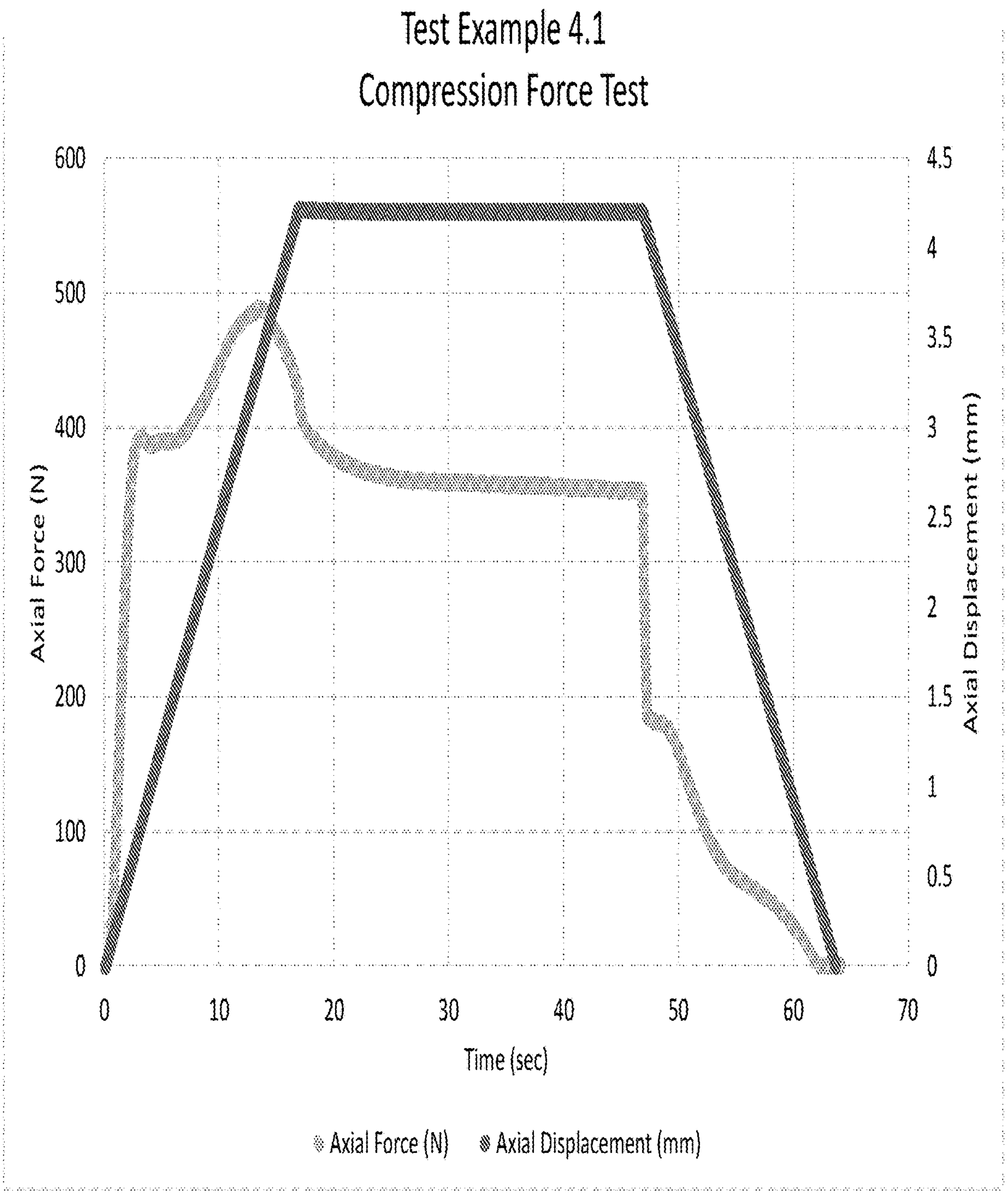
Figure 74:
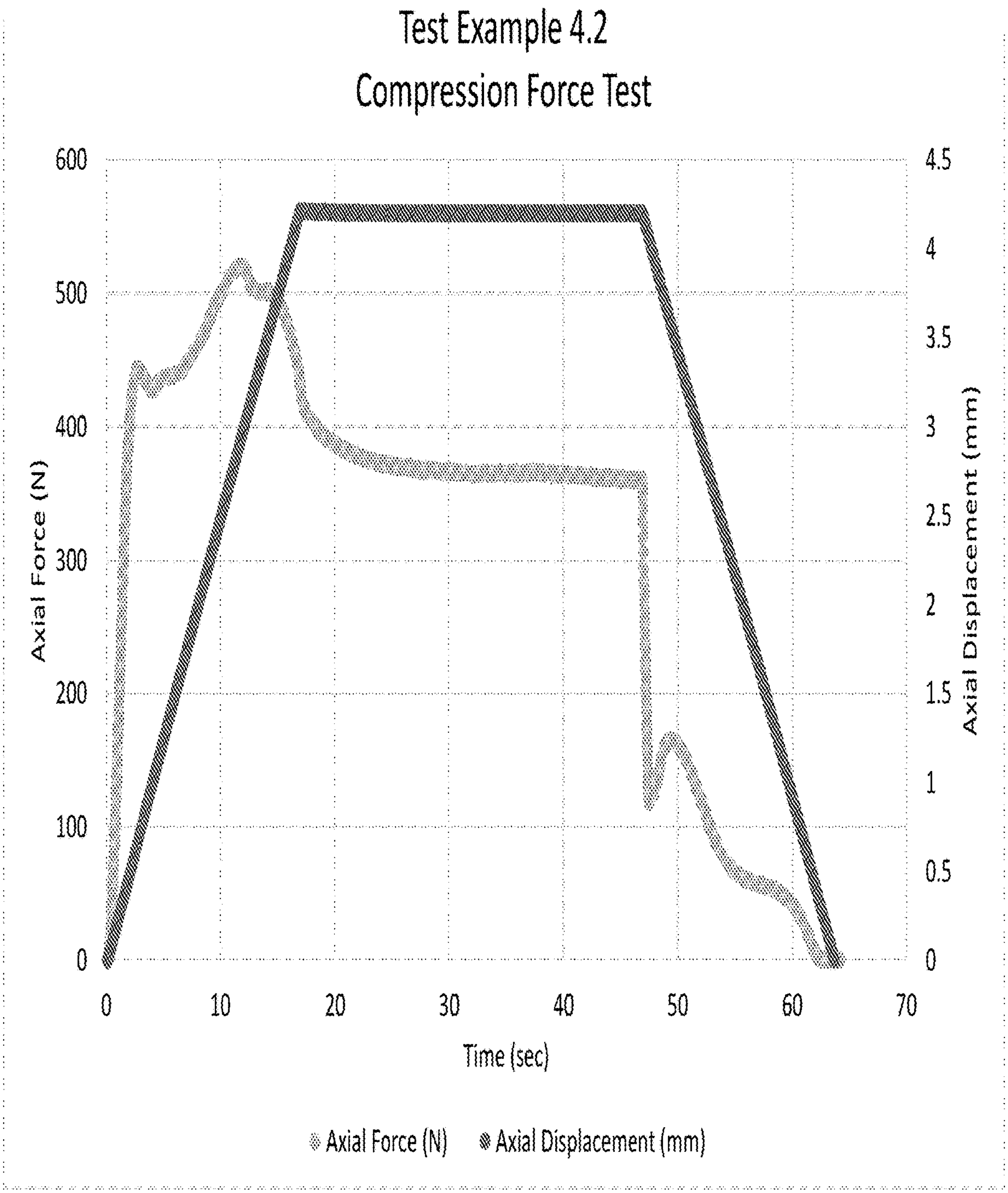
Figure 75:
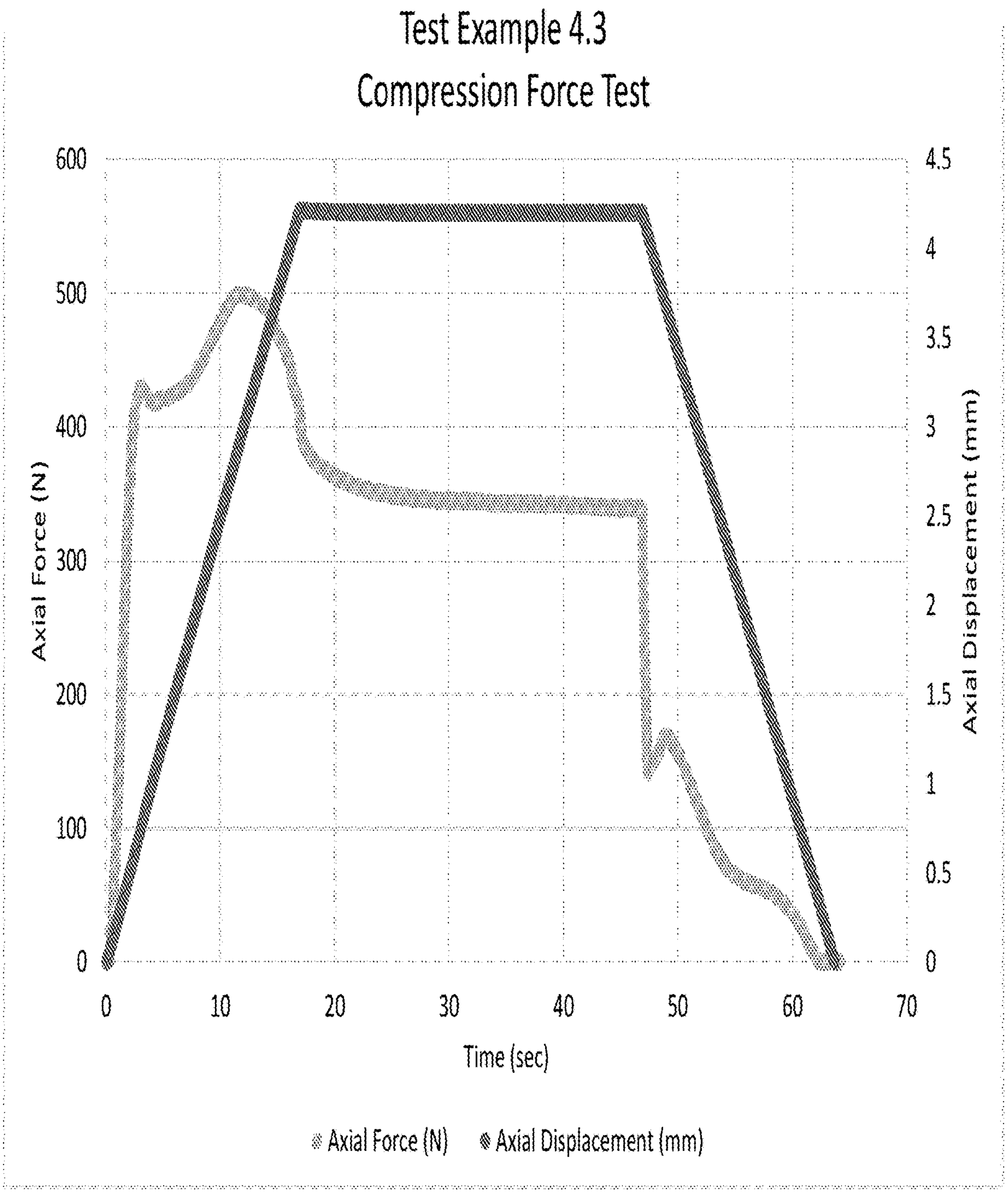
Figure 76:
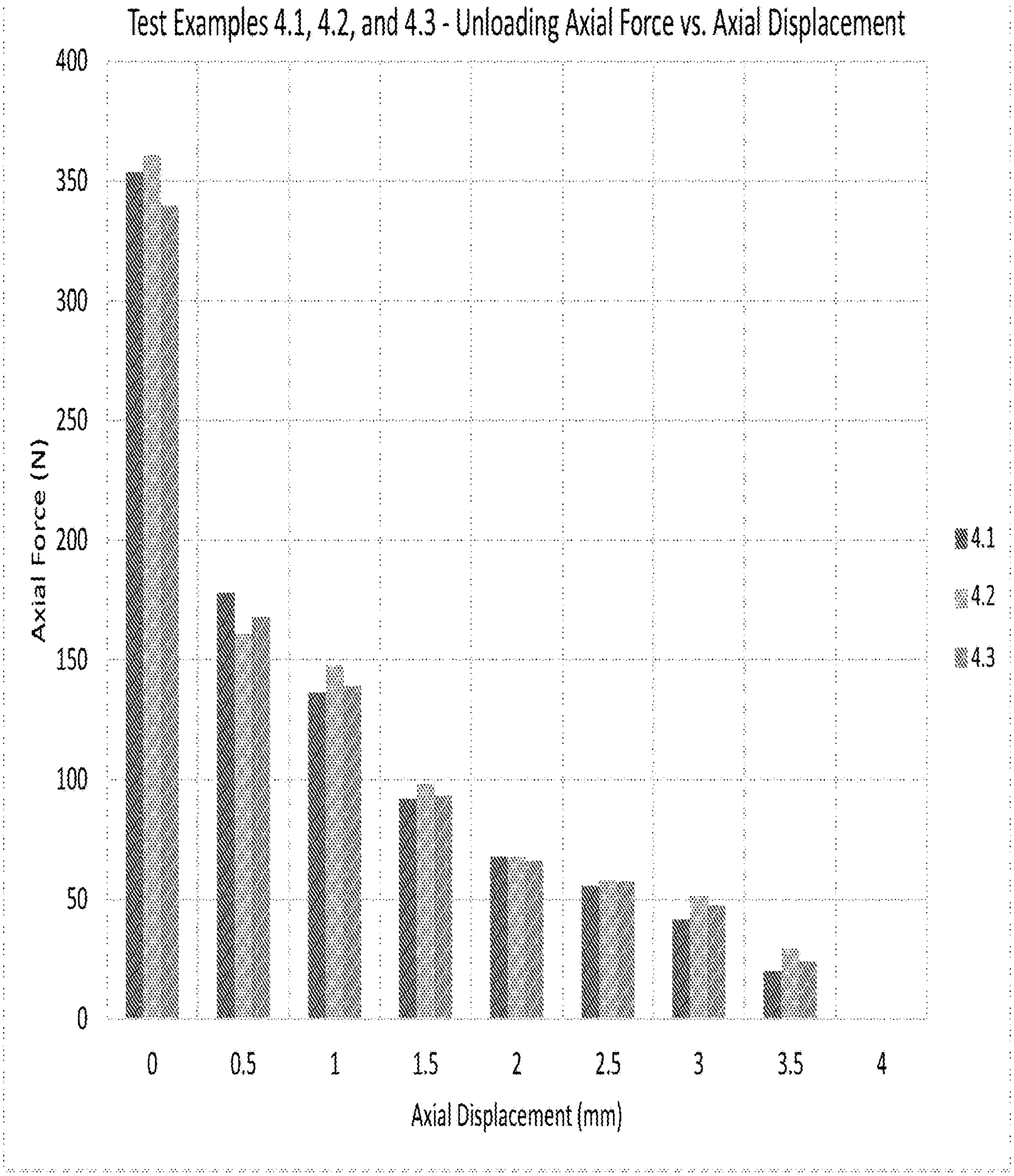

The graphs of FIGS. 73-75 show axial displacement of the test jigs over the test period and axial force exerted between the test jigs and the compression device of test examples 4.1, 4.2, and 4.3 over the same period. FIG. 76 shows a bar chart of axial force applied between the compression device and test jigs of test examples 4.1, 4.2, and 4.3, before and during the unloading process. These figures show that the compression devices of test examples 4.1, 4.2, and 4.3 continued to exert axial compressive force as the testing apparatus advanced the foam blocks back together.

Table 4 shows, for test examples 4.1, 4.2, and 4.3, the maximum applied displacement, the peak force applied for the maximum applied displacement; and the force applied to maintain the maximum applied displacement after 30 seconds.

TABLE 4

| Test Example | Maximum applied displacement (mm) | Peak force applied (N) | Force applied after 30 Secs (N) |
|---|---|---|---|
| 4.1 | 4.20 | 489 | 353 |
| 4.2 | | 521 | 361 |
| 4.3 | | 500 | 340 |
| Avg. | — | 503 | 351 |
| Std. Dev. | — | 16 | 11 |

Comparative Example A

Comparative test examples A.1, A.2, and A.3 were tested in the same manner as in Example 1, except that testing was conducted using bone screws having 7.0 mm thread diameters and no compression devices were used. For each of comparative test examples A.1, A.2, and A.3, the screw and blocks were assembled as follows. A countersink was provided in the first foam block. The threaded portion of the screw was advanced through the countersink of the first block and then through the second block. The head of the screw was positioned against a surface of the first foam block within the countersink. Spacing was maintained between the two blocks after insertion of the screw.

Figure 77:
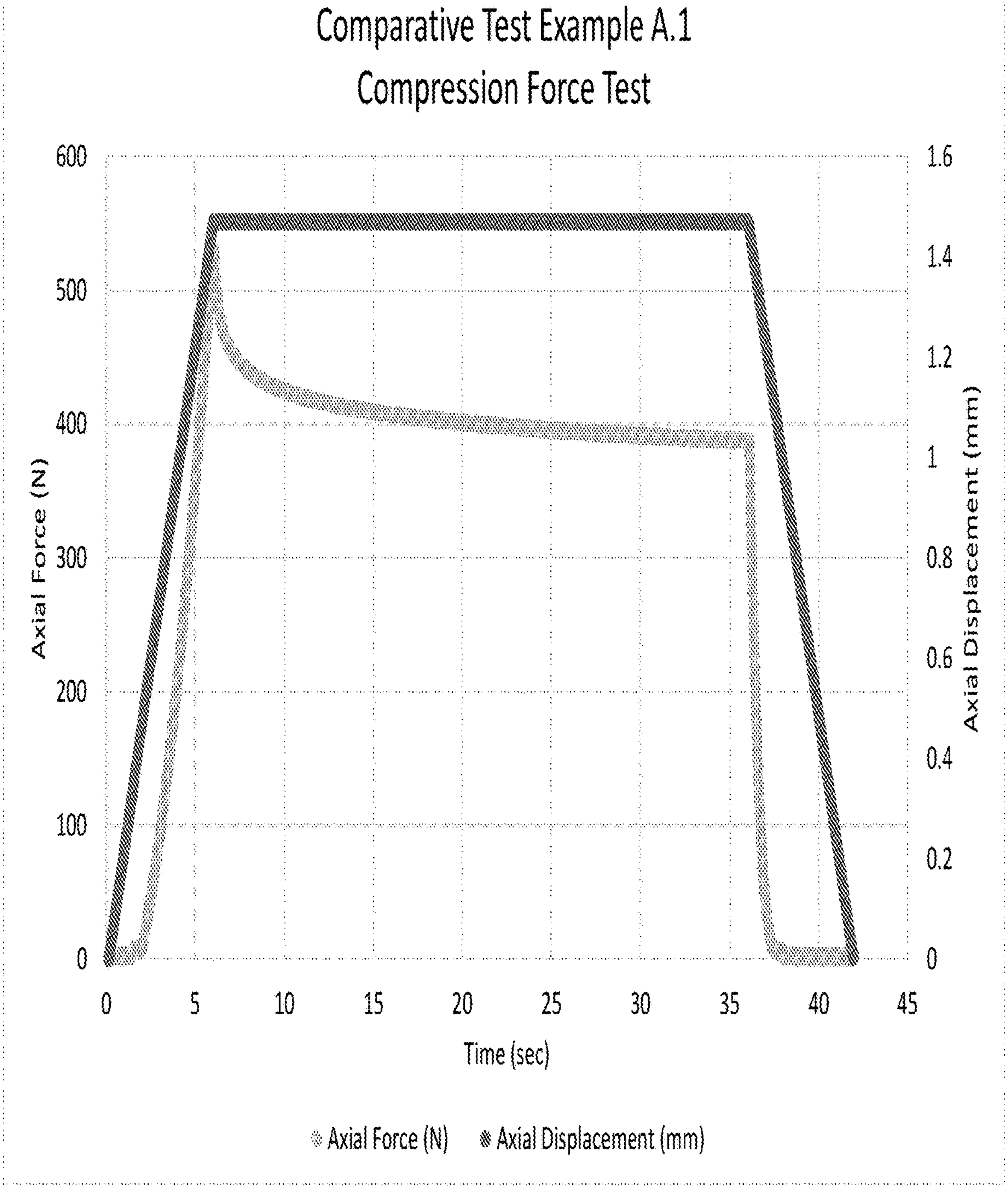
Figure 78:
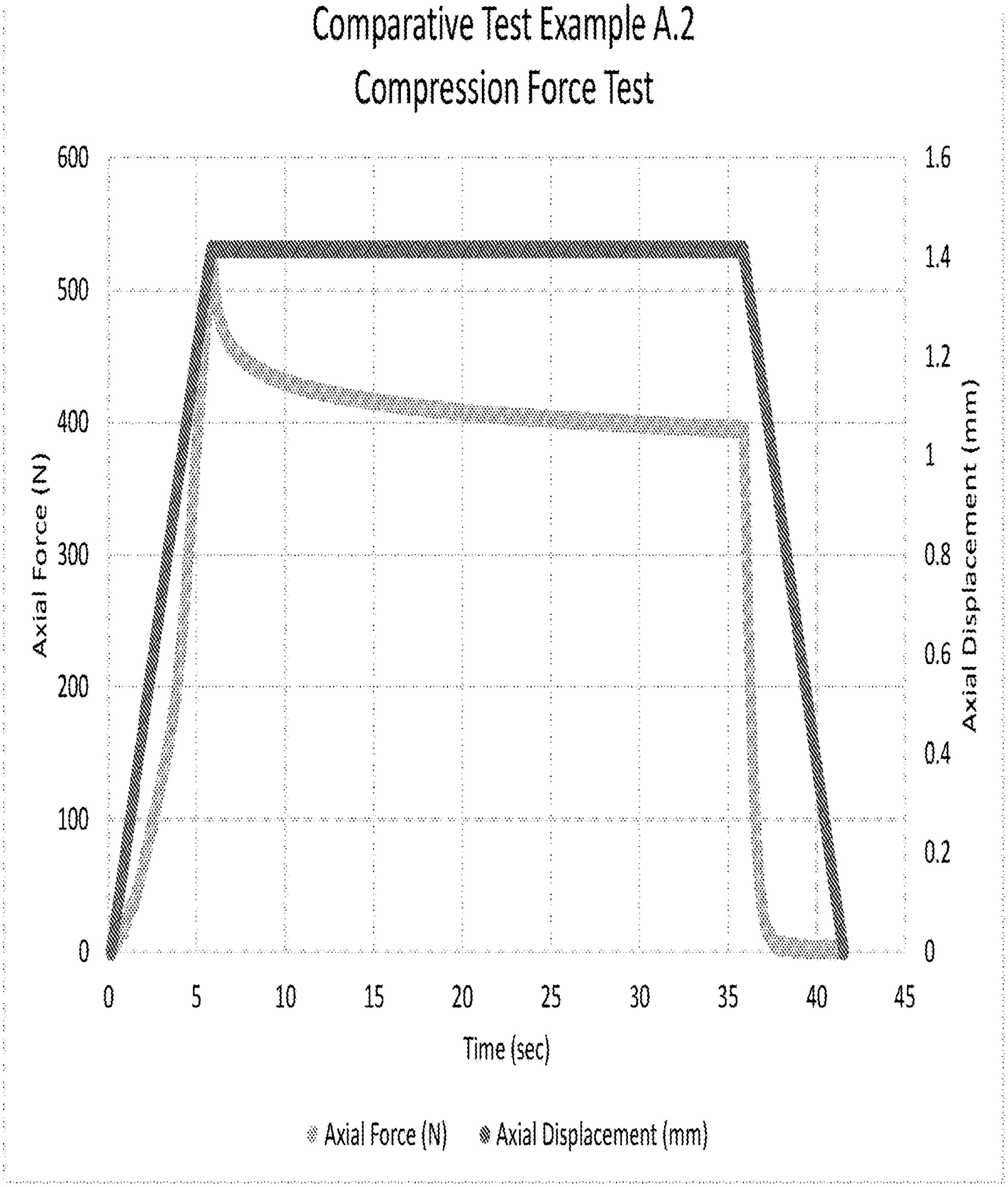
Figure 79:
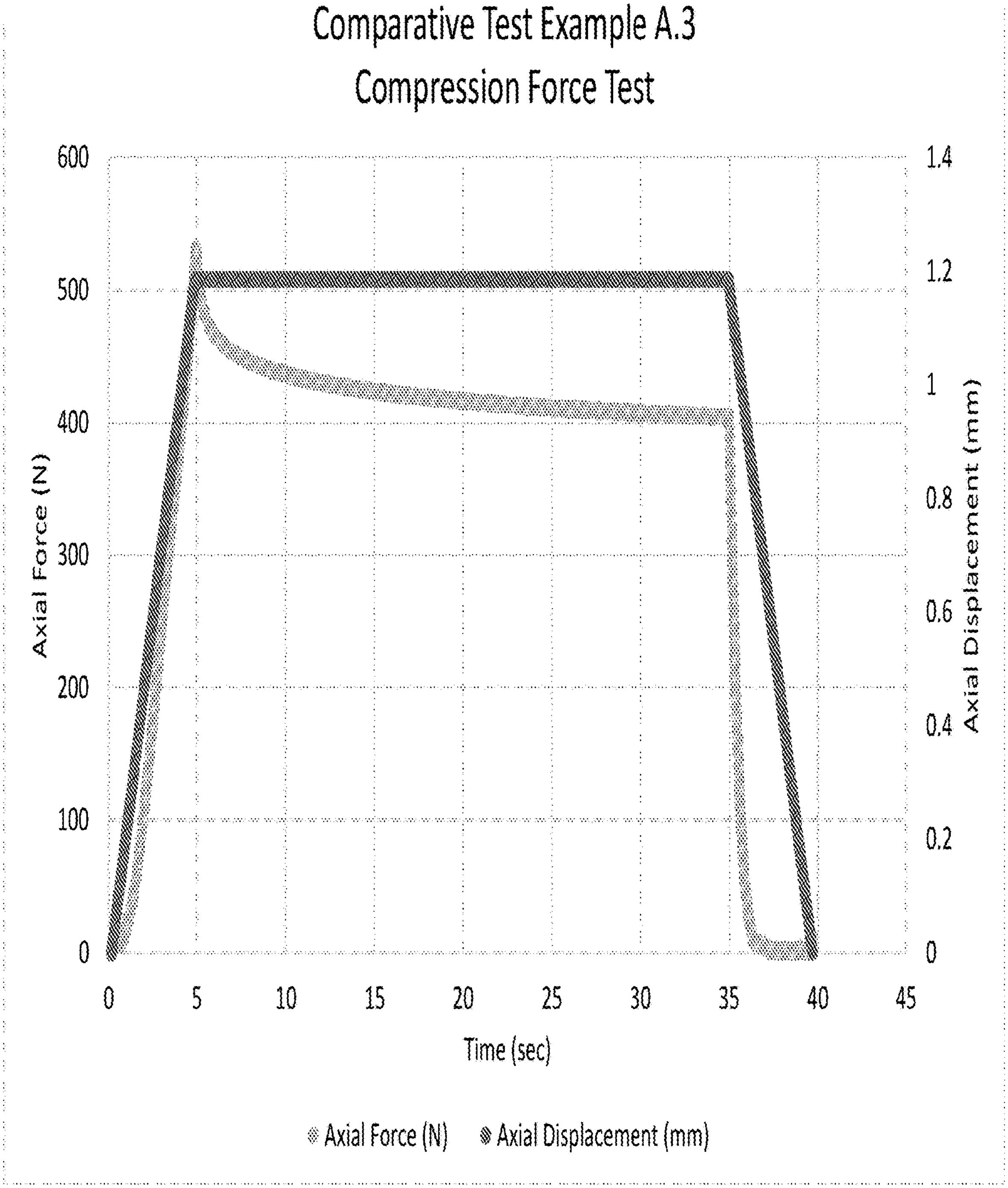
Figure 80:
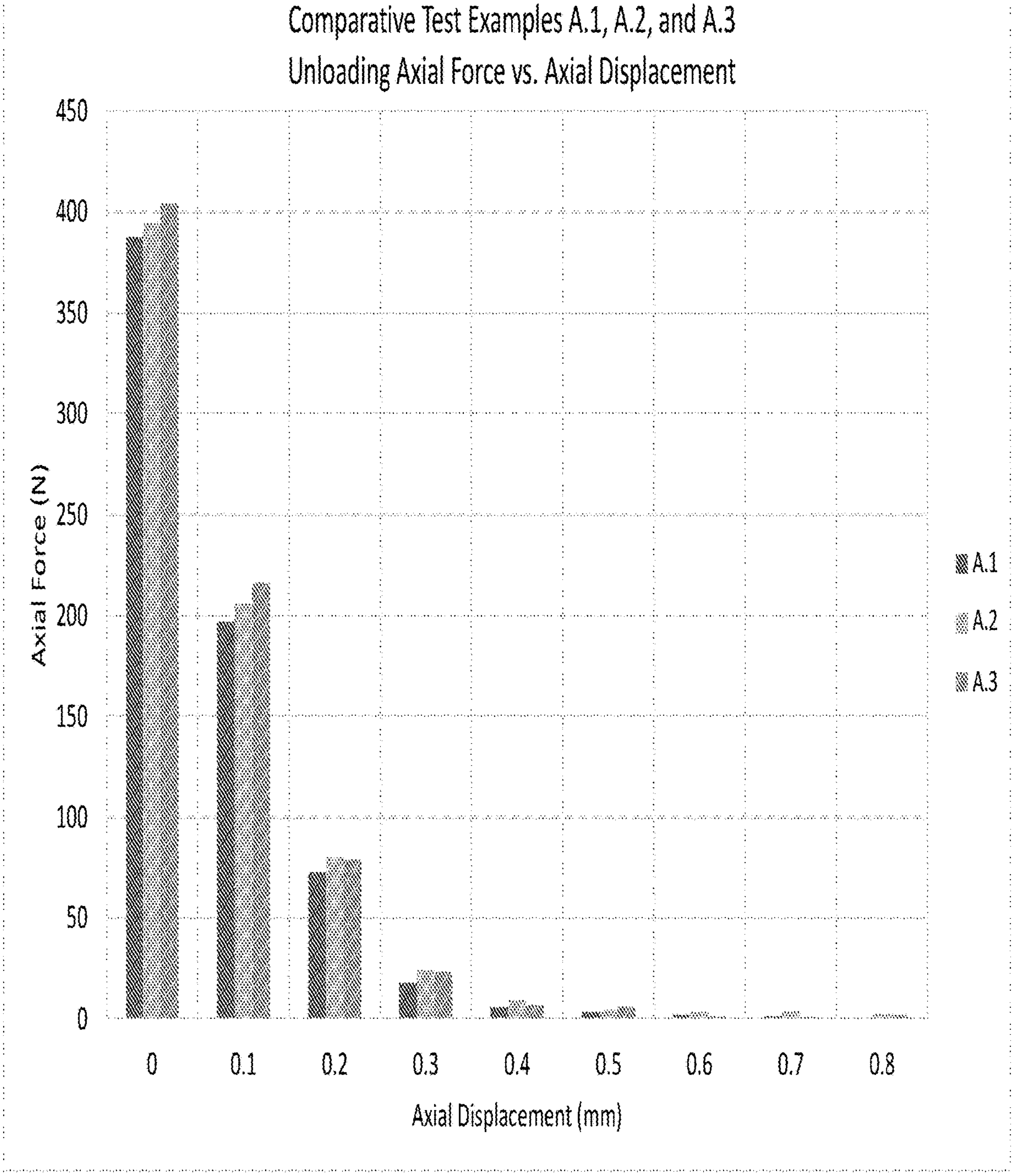

FIGS. 77-79 show graphs of axial displacement between the test jigs over the test period and axial force exerted between the screw head (positioned against the first foam block) and the test jigs during the same period. FIG. 80 shows a bar chart of axial force exerted between the screw head and test jigs of comparative test examples A.1, A.2, and A.3, before and during the unloading process. These figures show a rapid reduction of force between the screw head and test jigs during the unloading process.

Table 5 shows, for comparative test examples A.1, A.2, and A.3, the maximum applied displacement (maximum separation) between the test jigs during the test, the peak force applied between the test jigs and screw head at the maximum applied displacement, and the force applied between the test jigs and the compression device after maintaining maximum applied displacement for 30 seconds.

TABLE 5

| Comparative Test Example | Maximum applied displacement (mm) | Peak force applied (N) | Force applied after 30 Secs (N) |
|---|---|---|---|
| A.1 | 1.47 | 530 | 388 |
| A.2 | 1.42 | 532 | 395 |
| A.3 | 1.19 | 530 | 404 |
| Avg. | — | 531 | 395 |
| Std. Dev. | — | 1 | 8 |

A comparison of FIGS. 76 and 80 shows that the compression devices of test examples 4.1, 4.2, and 4.3 (utilizing screws having 7 mm thread diameters) exerted at least 50 N of compressive force at up to 2.5 mm of displacement during the unloading process, whereas the screw heads of comparative test examples A.1, A.2, and A.3 (also utilizing screws having 7 mm thread diameters) exhibited compressive for forces of less than 50 N upon 0.3 mm of displacement during the unloading process. Therefore, the compression devices of test examples 4.1, 4.2, and 4.3 provided superior compressive forces (gap recovery forces) during unloading of tension between the foam blocks when compared with comparative test examples A.1, A.2, and A.3.

Comparative Example B

Comparative test examples B.1, B.2, and B.3 were tested in the same manner as in Example 1, except that testing was conducted using bone screws having 7.0 mm thread diameters and washers. The washers were flat, composed of Ti-6Al-4V alloy, had a 15 mm outer diameter, an 8.07 mm inner diameter, and thickness of 1.5 mm. A countersink was provided in the first foam block. The screw was advanced through opening of the washer, into the countersink bore, similar to a clinical application where a washer is used to gain additional cortical purchase, through the first block, and then through the second block.

Figure 81:
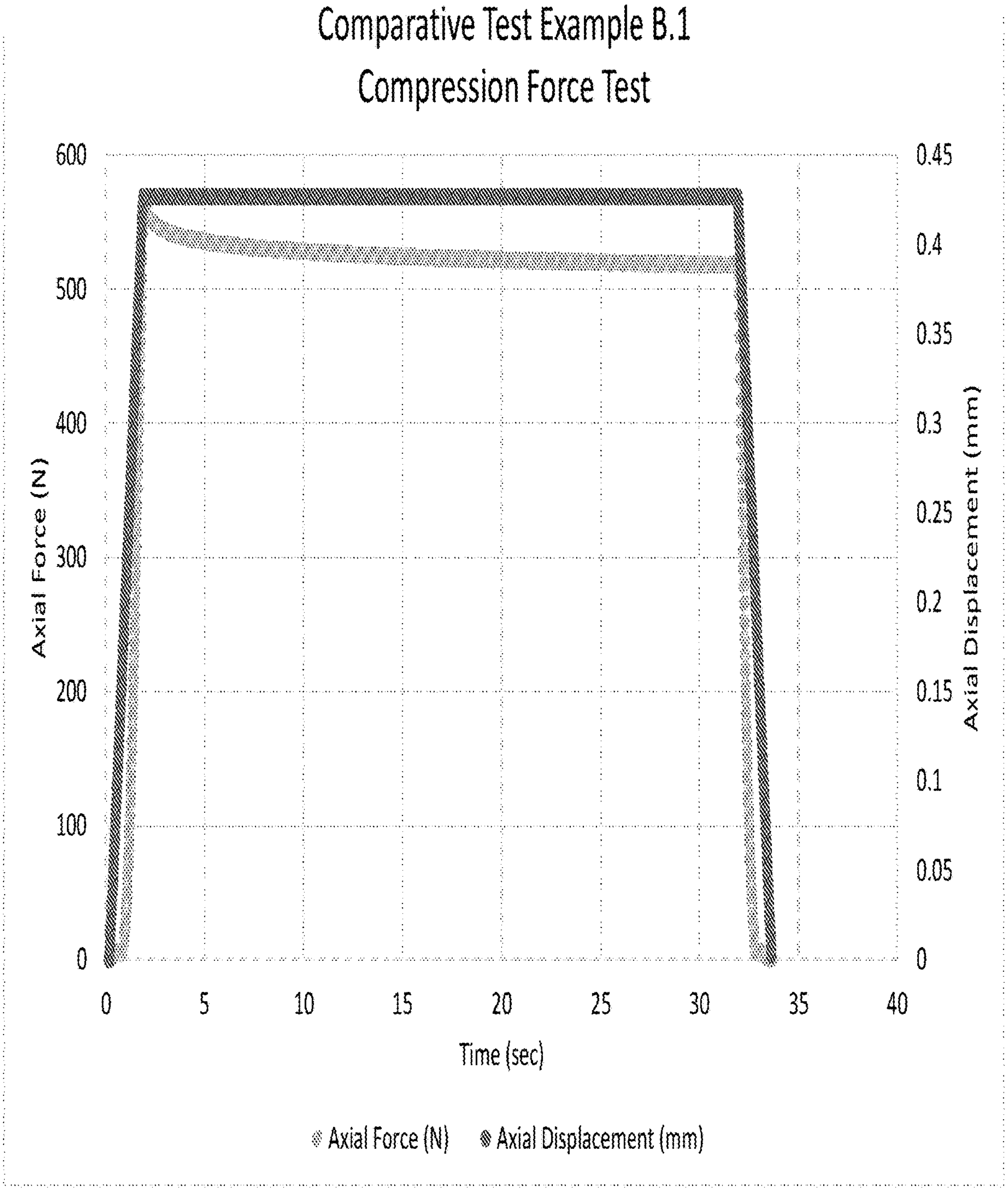
Figure 82:
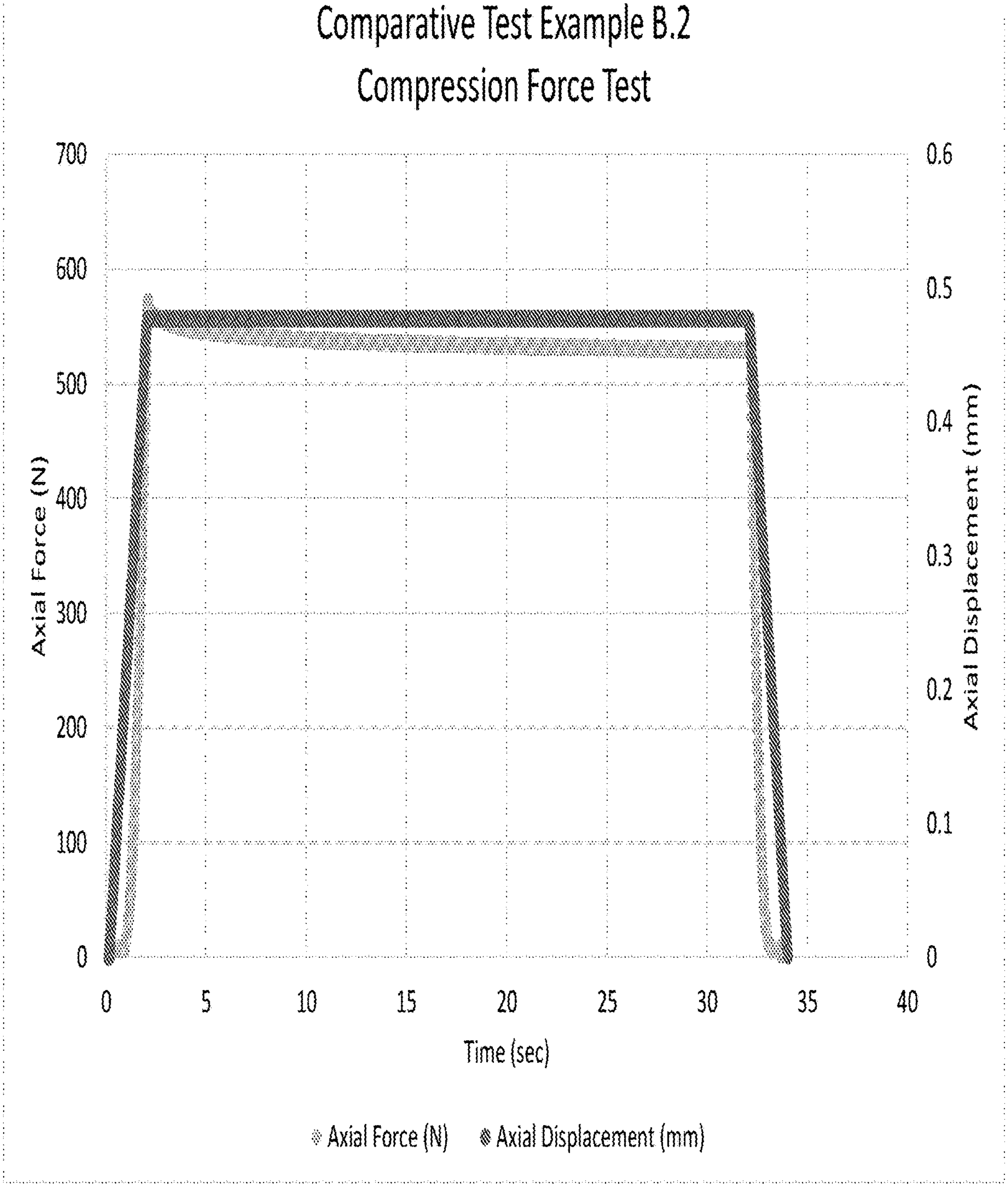
Figure 83:
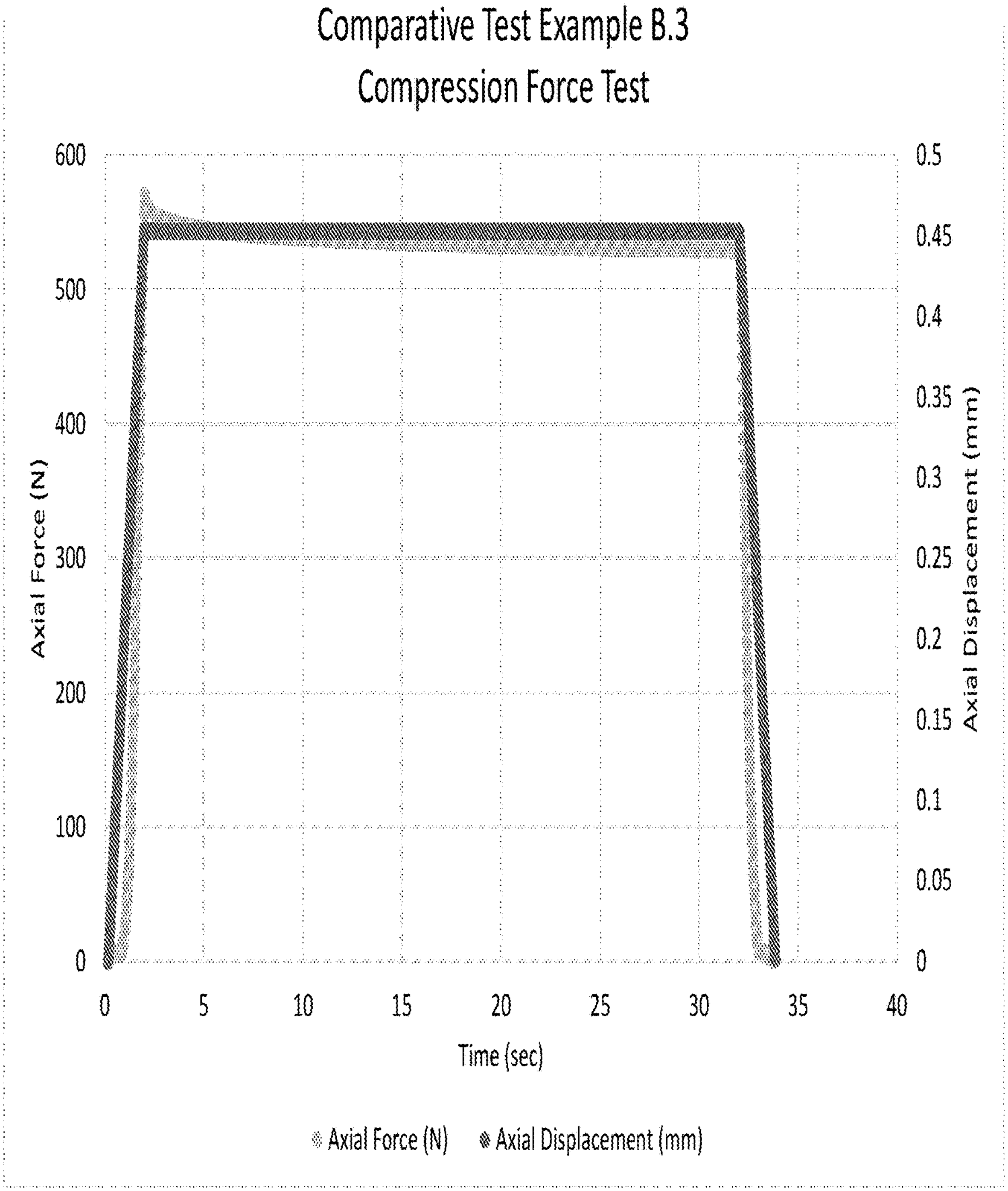
Figure 84:
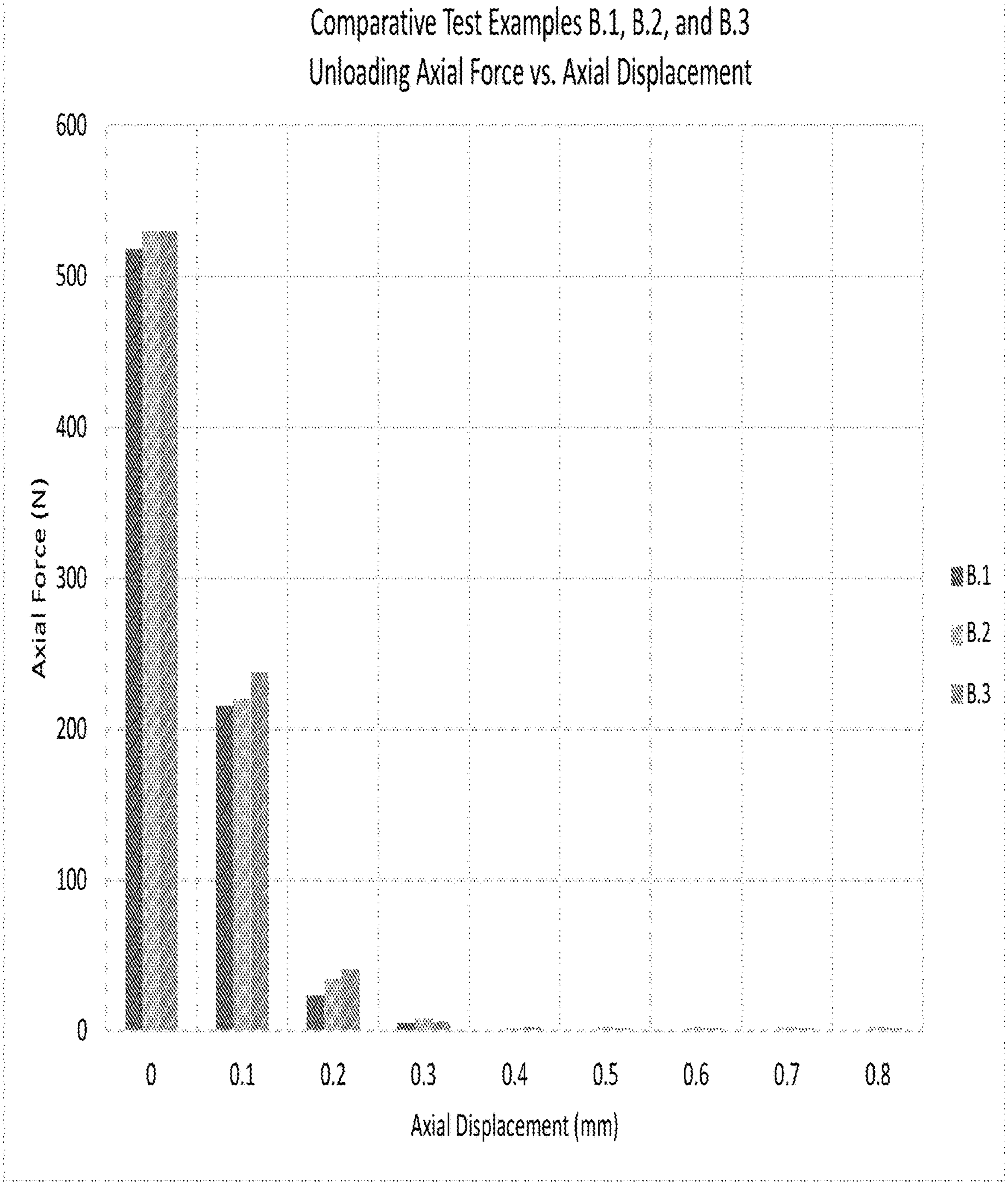

For comparative test examples B.1, B.2, and B.3, the graphs in FIGS. 81-83 show axial displacement between the test jigs over the test period and axial force exerted between the washer (against the first foam block) and the test jigs during the same period. FIG. 84 shows a bar chart of axial force exerted between the washer and test jigs of comparative test examples B.1, B.2, and B.3, before and during the unloading process. These figures show a rapid reduction of force between the screw head and test jigs during the unloading process (i.e., when moving the test jigs back together).

Table 6 shows, for comparative test examples B.1, B.2, and B.3, the maximum applied displacement (maximum separation) between the test jigs during the test; the peak force applied between the test jigs and washer at the maximum applied displacement; and the force applied to maintain the maximum applied displacement between the test jigs and washer after 30 seconds.

TABLE 6

| Comparative Test Example | Maximum applied displacement (mm) | Peak force applied (N) | Force applied after 30 Secs (N) |
|---|---|---|---|
| B.1 | 0.43 | 566 | 518 |
| B.2 | 0.48 | 572 | 530 |
| B.3 | 0.45 | 571 | 530 |
| Avg. | — | 570 | 526 |
| Std. Dev. | — | 3 | 7 |

A comparison of FIGS. 76 and 84 shows that the compression devices of test examples 4.1, 4.2, and 4.3 (utilizing screws having 7 mm thread diameters) exerted at least 50 N of compressive force at up to 2.5 mm of displacement during the unloading process, whereas the washers comparative test examples B.1, B.2, and B.3 (also utilizing screws having 7 mm thread diameters) exhibited compressive forces of less than 50 N upon 0.2 mm of displacement during the unloading process. Therefore, the compression devices of test examples 4.1, 4.2, and 4.3 provided superior compressive forces during unloading of tension between the foam blocks when compared with comparative test examples B.1, B.2, and B.3.

It is thus seen that any of a compression device, a bone plate assembly, and a bone plate comprising at least an inwardly projecting resilient structure integral with the plate body, as configured as described herein, can assist in maintaining compression between bone segments or in a bone fracture, as can the disclosed kit and methods.

Uses of singular terms such as “a,” “an,” are intended to cover both the singular and the plural, unless otherwise indicated herein or clearly contradicted by context. The terms “comprising,” “having,” “including,” and “containing” are to be construed as open-ended terms. Any description of certain embodiments as “preferred” embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., “such as”) provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A bone plate comprising:

a plate body including an upper plate surface, a lower plate surface, and an aperture through the plate body, an inwardly projecting resilient tooth integral with the plate body and extending toward an axis of the aperture;

wherein the plate body and the resilient tooth comprise a material that is superelastic at human body temperatures, and wherein the resilient tooth includes a tip portion extending distally beyond a lower surface of a peripheral portion of the tooth toward the lower plate surface in an unbiased state;

further comprising a countersunk region open to the upper plate surface and formed about the aperture, the tooth extending from an inner intermediate surface of the countersunk region.

2. The bone plate of claim 1, comprising a plurality of inwardly projecting resilient teeth integral with the plate body, the teeth configured to exert a biasing force in a direction when deformed in an opposing direction.

3. The bone plate of claim 2, the plate body and teeth comprising polyether ether ketone.

4. The bone plate of claim 2, the plate body and teeth comprising a titanium alloy.

5. The bone plate of claim 1, including a countersunk region open to the lower plate surface.

6. The bone plate of claim 1, including plural teeth each having a cuboid projecting portion with a first side edge, a second side edge, and a terminal side edge.

7. The bone plate of claim 1, including plural teeth each having a triangular projecting portion.

* * * * *